United States Patent
Caron et al.

(10) Patent No.: US 10,722,175 B2
(45) Date of Patent: Jul. 28, 2020

(54) SYSTEM AND APPARATUS COMPRISING A MULTISENSOR GUIDEWIRE FOR USE IN INTERVENTIONAL CARDIOLOGY

(71) Applicant: Three Rivers Cardiovascular Systems Inc., Toronto (CA)

(72) Inventors: Eric Caron, Toronto (CA); Luc Bilodeau

(73) Assignee: HemoCath Ltd., Toronto (CA)

( * ) Notice: Subject to any disclaimer, the term of this patent is extended or adjusted under 35 U.S.C. 154(b) by 598 days.

(21) Appl. No.: 15/326,134

(22) PCT Filed: Jul. 10, 2015

(86) PCT No.: PCT/IB2015/055240
§ 371 (c)(1),
(2) Date: Jan. 13, 2017

(87) PCT Pub. No.: WO2016/009317
PCT Pub. Date: Jan. 21, 2016

(65) Prior Publication Data
US 2017/0209099 A1      Jul. 27, 2017

Related U.S. Application Data

(60) Provisional application No. 62/023,891, filed on Jul. 13, 2014, provisional application No. 62/039,952, filed on Aug. 21, 2014.

(51) Int. Cl.
*A61B 5/00* (2006.01)
*A61B 5/042* (2006.01)
(Continued)

(52) U.S. Cl.
CPC ........ *A61B 5/6851* (2013.01); *A61B 5/02154* (2013.01); *A61B 5/02158* (2013.01);
(Continued)

(58) Field of Classification Search
CPC ...... G05B 2219/32287; A61B 1/00009; A61B 1/00039; A61B 2576/00; A61B 34/20;
(Continued)

(56) References Cited

U.S. PATENT DOCUMENTS 4,543,961 A   10/1985 Brown
4,621,929 A   11/1986 Phillips
(Continued)

FOREIGN PATENT DOCUMENTS

CA         2849717 A1    5/2013
CN       102202562 A     9/2011
(Continued)

OTHER PUBLICATIONS

JPO Machine translation of JP2005-291945 listed above.
(Continued)

*Primary Examiner* — Deborah L Malamud
(74) *Attorney, Agent, or Firm* — Miltons IP/p.i.

(57) ABSTRACT

A system (1) and apparatus comprising a multisensor guidewire (100/200/300) for use in interventional cardiology, e.g., Transcatheter Valve Therapies (TVT), comprises a plurality of optical sensors (10/20) for direct measurement of cardiovascular parameters, e.g. transvalvular blood pressure gradients and flow. A conventional outer coil wire (35) contains a shaped core wire (31) having a cross-section defining a channel surface (132), e.g. grooves (32), extending along its length, to position optical fibers (11) and optical sensors (10/20) in a channel (33). Advantageously, the core wire has a diameter that provides sufficient stiffness to the guidewire for use as a support guidewire for TVT, e.g. Transcatheter Aortic Valve Implantation (TAVI), while accommodating multiple sensors and fibers within a guidewire of outside diameter ≤0.89 mm. An optical connector (112) couples the guidewire to a control system (150). Optionally, the guide-
(Continued)

wire includes a contact force sensor (60), a pre-formed tip (400-1/400-2) and a separable micro-connector (140).

13 Claims, 38 Drawing Sheets

(51) Int. Cl.
   *A61B 5/0215* (2006.01)
   *A61F 2/24* (2006.01)
(52) U.S. Cl.
   CPC ............ *A61B 5/042* (2013.01); *A61F 2/2427* (2013.01); *A61B 2560/0462* (2013.01); *A61B 2560/066* (2013.01); *A61B 2562/228* (2013.01); *A61F 2/24* (2013.01); *A61F 2/2418* (2013.01)
(58) Field of Classification Search
   CPC ... A61B 5/0077; A61B 1/05; A61B 2034/301; A61B 34/30; A61B 2018/00982; A61B 2034/2055; A61B 2560/0462; A61B 2562/0247; A61B 2562/228; A61B 5/00; A61B 5/0024; A61B 5/021; A61B 5/02154; A61B 5/02158; A61B 5/6851; A61B 5/064; A61B 5/065; A61B 5/066; A61B 5/486; Y10S 901/46
   See application file for complete search history.

(56) References Cited

U.S. PATENT DOCUMENTS

| | | | |
|---|---|---|---|
| 4,730,622 A | 3/1988 | Cohen | |
| 4,735,212 A | 4/1988 | Cohen | |
| 4,850,358 A | 7/1989 | Millar | |
| 4,873,989 A | 10/1989 | Einzig | |
| 4,953,553 A | 9/1990 | Tremulis | |
| 4,966,148 A | 10/1990 | Millar | |
| 5,018,529 A | 5/1991 | Tenerz et al. | |
| 5,115,127 A | 5/1992 | Bobb et al. | |
| 5,125,058 A | 6/1992 | Tenerz et al. | |
| 5,152,291 A | 10/1992 | Dias | |
| 5,178,153 A | 1/1993 | Einzig | |
| 5,208,650 A | 5/1993 | Giallorenzi | |
| 5,226,423 A | 7/1993 | Tenerz et al. | |
| 5,392,117 A | 2/1995 | Belleville et al. | |
| 5,514,128 A | 5/1996 | Hillsman et al. | |
| 5,520,190 A | 5/1996 | Benedict et al. | |
| 5,574,699 A | 11/1996 | Cuomo | |
| 5,873,835 A | 2/1999 | Hastings et al. | |
| 6,107,004 A | 8/2000 | Donadio, III | |
| 6,112,598 A | 9/2000 | Tenerz et al. | |
| 6,167,763 B1 | 1/2001 | Tenerz et al. | |
| 6,254,550 B1 | 7/2001 | McNamara et al. | |
| 6,336,906 B1 | 1/2002 | Hammarstrom et al. | |
| 6,343,514 B1 | 2/2002 | Smith | |
| 6,431,010 B1 | 8/2002 | Joffe | |
| 6,585,660 B2 | 7/2003 | Dorando et al. | |
| 6,615,667 B2 | 9/2003 | Smith | |
| 6,976,965 B2 | 12/2005 | Corl et al. | |
| 6,986,739 B2 | 1/2006 | Warren et al. | |
| 7,097,620 B2 | 8/2006 | Corl et al. | |
| 7,134,994 B2 | 11/2006 | Alpert et al. | |
| 7,274,956 B2 | 9/2007 | Mott et al. | |
| 7,329,223 B1 | 2/2008 | Ainsworth et al. | |
| 7,450,989 B2 | 11/2008 | Svanerudh | |
| 7,532,920 B1 | 5/2009 | Ainsworth et al. | |
| 7,684,657 B2 | 3/2010 | Donlagic et al. | |
| 7,689,071 B2 | 3/2010 | Belleville et al. | |
| 7,731,664 B1 | 6/2010 | Millar | |
| 7,783,338 B2 | 8/2010 | Ainsworth et al. | |
| 7,931,603 B2 | 4/2011 | Von Malmborg et al. | |
| 7,967,761 B2 | 6/2011 | Smith | |
| 7,967,762 B2 | 6/2011 | Corl et al. | |
| 8,317,715 B2 | 11/2012 | Belleville et al. | |
| 8,758,333 B2 | 6/2014 | Harlan | |
| 8,936,401 B2 | 1/2015 | Belleville | |
| 9,052,466 B2 | 6/2015 | Belleville et al. | |
| 9,149,230 B2 | 10/2015 | Caron et al. | |
| 9,504,392 B2 | 11/2016 | Caron et al. | |
| 2003/0095263 A1 | 5/2003 | Varshneya et al. | |
| 2003/0100824 A1 | 5/2003 | Warren et al. | |
| 2004/0075841 A1 | 4/2004 | Van Neste et al. | |
| 2004/0253365 A1 | 12/2004 | Warren et al. | |
| 2006/0133715 A1 | 6/2006 | Belleville et al. | |
| 2007/0038173 A1 | 2/2007 | Simpson | |
| 2008/0249388 A1 | 10/2008 | Kumhyr | |
| 2008/0312597 A1 | 12/2008 | Uihlein | |
| 2010/0228112 A1 | 9/2010 | Von Malmborg | |
| 2010/0234698 A1 | 9/2010 | Manstrom et al. | |
| 2010/0241008 A1 | 9/2010 | Belleville et al. | |
| 2011/0004198 A1 | 1/2011 | Hoch | |
| 2011/0023617 A1 | 2/2011 | Yu et al. | |
| 2011/0066047 A1 | 3/2011 | Belleville et al. | |
| 2011/0092784 A1 | 4/2011 | Butler et al. | |
| 2011/0234698 A1 | 9/2011 | Sakata et al. | |
| 2012/0016342 A1 | 1/2012 | Brecker | |
| 2012/0197097 A1 | 8/2012 | Chan et al. | |
| 2012/0227505 A1 | 9/2012 | Belleville et al. | |
| 2013/0051731 A1 | 2/2013 | Belleville et al. | |
| 2013/0218032 A1 | 8/2013 | Belleville | |
| 2013/0274618 A1 | 10/2013 | Hou et al. | |
| 2013/0317372 A1 | 11/2013 | Eberle et al. | |
| 2014/0039325 A1 | 2/2014 | Belleville | |
| 2014/0107624 A1 | 4/2014 | Belleville | |
| 2014/0180030 A1 | 6/2014 | Dorando | |
| 2014/0180141 A1 | 6/2014 | Millett | |
| 2014/0241669 A1 | 8/2014 | Belleville et al. | |
| 2014/0243688 A1 | 8/2014 | Caron et al. | |
| 2014/0248021 A1 | 9/2014 | Belleville et al. | |
| 2014/0249386 A1 | 9/2014 | Caron et al. | |
| 2015/0057532 A1 | 2/2015 | Belleville | |
| 2015/0141843 A1 | 5/2015 | Eberle et al. | |
| 2015/0196392 A1 | 7/2015 | Sigmon, Jr. et al. | |
| 2015/0265167 A1 | 9/2015 | McGowan et al. | |
| 2016/0022159 A1 | 1/2016 | Caron et al. | |

FOREIGN PATENT DOCUMENTS

| | | | |
|---|---|---|---|
| CN | 103153162 A | 6/2013 | |
| EP | 1105181 A1 | 6/2001 | |
| EP | 1849409 A1 | 10/2007 | |
| JP | H05-329119 A | 12/1993 | |
| JP | 2003507111 A | 2/2003 | |
| JP | 2005291945 A | 10/2005 | |
| JP | 2007296354 A | 11/2007 | |
| WO | 9214515 A1 | 9/1992 | |
| WO | 0113789 A1 | 3/2001 | |
| WO | 2004018031 A2 | 3/2004 | |
| WO | 2009054802 A1 | 4/2009 | |
| WO | 2010092347 A1 | 8/2010 | |
| WO | 2011048509 A1 | 4/2011 | |
| WO | 2011101813 A1 | 8/2011 | |
| WO | 2012029013 A1 | 3/2012 | |
| WO | 2012061935 A1 | 5/2012 | |
| WO | 2012164481 A1 | 12/2012 | |
| WO | 2013028737 A1 | 2/2013 | |
| WO | 2013061280 A1 | 5/2013 | |
| WO | 2013061281 A1 | 5/2013 | |
| WO | 2013061281A1 A1 | 5/2013 | |
| WO | 2013177577 A2 | 11/2013 | |
| WO | 2014081942 | 5/2014 | |
| WO | 2015142623 A1 | 9/2015 | |

OTHER PUBLICATIONS

JPO Machine translation of JPH05-329119 listed above.
Pinet et al.; "Ultra-miniature all-glass Fabry-Perot pressure sensor manufactured at the tip of a multimode optical fiber"; FISO Technologies Inc. ; Proceedings of SPIE, vol. 6770 (2007).
Hamel et al. ; "Temperature and pressure Fiber-Optic sensors applied to minimally invasive diagnostics and therapies"; FISO

(56) References Cited

OTHER PUBLICATIONS

Technologies Inc.; Whitepaper/Publication; (2006).
Pinet, Eric; "Pressure measurement with fiber-optic sensors: Commerical technologies and applications"; FISO Technologies Inc.; 21st International Conference on Optical Fiber Sensors, edited by Wojtek J. Bock et al.; Proc. of SPIE vol. 7753 (May 17, 2011).
Pinet, Eric; "Disposable fiber-optic sensors for clinical environments"; SPIE 2007.
Tenerz, L; "A Fiberoptic Silicon Pressure Microsensor for Measurements in Coronary Arteries"; Radi Medical Systems; IEEE 1991.
Hamel et al."Pressure Fiber-Optic Sensors in Intra-aortic Balloon Pumping Therapy"; European Medical Device Manufacturer Editorial: Sensors and Transducers integrated in medical equipment or used in manufacturing process; FISO Technologies Inc.; Whitepaper/Publication 2006.
FOP-F125 Pressure Sensor; FISO Technologies Inc.; Preliminary Datasheet dated 2008.
PressureWire Certus FFR Measurement System; Product information dated 2011 and 2009.
PressureWire Certus FFR Measurement System; Product Information; 2011.
Vaguine et al.; "Multiple Sensor Optical Thermometry System for Application in Clinical Hyperthermia"; IEEE Transactions on Biomedical Engineering vol. BME-31, No. 1, pp. 168-172; Jan. 1984.
Silvestri et al.; Optical fiber measurement systems for medical applications; p. 205-225; Oct. 5, 2011.
Boston Scientific—Comet(Tm)FR Guidewire—Product literature—Oct. 2015; 2 pages.
Volcano Prime Wire Prestige—Product literature—Nov. 2012; 1 page.
Javier Escaned, "Boston Scientific: Designing the pressure guiedwire for contemporary PCI scenarios"; European Heart House, Coronary Physiology in the Catheterization Laboratory (9th Edition) Thursday Apr. 23-Saturday, Apr. 25, 2015.
Fort Wayne Wire Die, Inc., Product Brochure; "Single Crystal Natural Diamond Dies-More Wire Production for Your Die Investment"; fwwd.com (c) 2006.
Opsens Medical, Product Brochure "One Wire. Many Possibilities" OptoWire One, www.opsensmedical.com, 2014 Brochure; 5 pages.
Webb, et al., "Current Status of Transcatheter Aortic Valve Replacement", Journal of the American College of Cardiology, vol. 60, No. 6, 2012; pp. 483-492.
Roy, D. A., et al., "First-in-man assessment of a dedicated guidewire for transcatheter aortic valve implantation", EuroIntervention 2013; 8, pp. 1019-1025.
Harrison, G. J., et al., Experimental Investigation; "Guidewire Stiffness: What's in a Name?" J. Endovasc. Ther. 2011:18, pp. 797-801.
Volcano Prime Wire Prestige—Product literature: Jan. 2015 and Feb. 2015; 3 pages.
St. Jude Medical—Pressure Wire Aerius; Agile Tip Technology; "Wireless FFR Measurement with Outstanding Handling Performance" Product Literature; 2013; 2 pages.
M. Kern, "Comparing FFR Tools New wires Pressure Microcatheter", Cath Lab Digest, vol. 24, Issue 5, May 2016 (http://www.cathlabdigest.com/article/Comparing-FFR-Tools-New-Wires-Pressure-Microcatheter); 4 pages.
De Vecchi et al., "Catheter induced Errors in Pressure Measurements in Vessels: An in-vitro and numerical study" IEEE Transaction on Biomedical Engineering, vol. 61, No. 6, Jun. 2014; pp. 1844-1850.
Robert G. Grey et al., "Feasibility of In Vivo Pressure Measurement using a pressure tip catheter via transventricular puncture", ASAIO J. 2010 56(3) 194-199; May 1, 2011; pp. 1-14.
Eric Pinet, et al., FISO Technologies, "Temperature fiber-optic point sensors: Commercial technologies and industrial applications", MIDEM Conference Proceedings, Sep. 29-Oct. 1. (2010), Radenci, Slovenia, D. Đonlagić, I. Šorli, & P. Šorli (Eds), MIDEM (Pub.) ISBN 978-961-92933-0-0; pp. 31-43.
Jan M. Headley, RN, BS, CCRN; "Invasive Hemodynamic Monitoring: Physiological Principles and Clinical Applications"; Edwards Life Sciences; Irvine, California, © 2002 (http://ht.edwards.com/resourcegallery/products/swanganz/pdfs/invasivehdmphysprincbook.pdf ); 40 pages.
International Search Report issued on Corresponding International Patent Application No. PCT/IB2015/055240 dated Nov. 26, 2015.
Extended European Search Report issued on European Patent Application No. 15821600.2 dated Jan. 11, 2018; 8 pages.
Harrison, Gareth et al.; "Guidewire Stiffness: what's in a name?"; J. Endovasc Ther, 2011; Jan. 11, 2011; pp. 797-801 (XP002774731).
Office Action issued on corresponding Chinese Patent Application No. 201580044024.X; dated May 30, 2019.

A-A CUT-THROUGH VIEW OF FIG. 2

B-B CUT-THROUGH VIEW OF FIG. 2

C-C CUT-THROUGH VIEW OF FIG. 2

D-D CUT-THROUGH VIEW OF FIG. 2

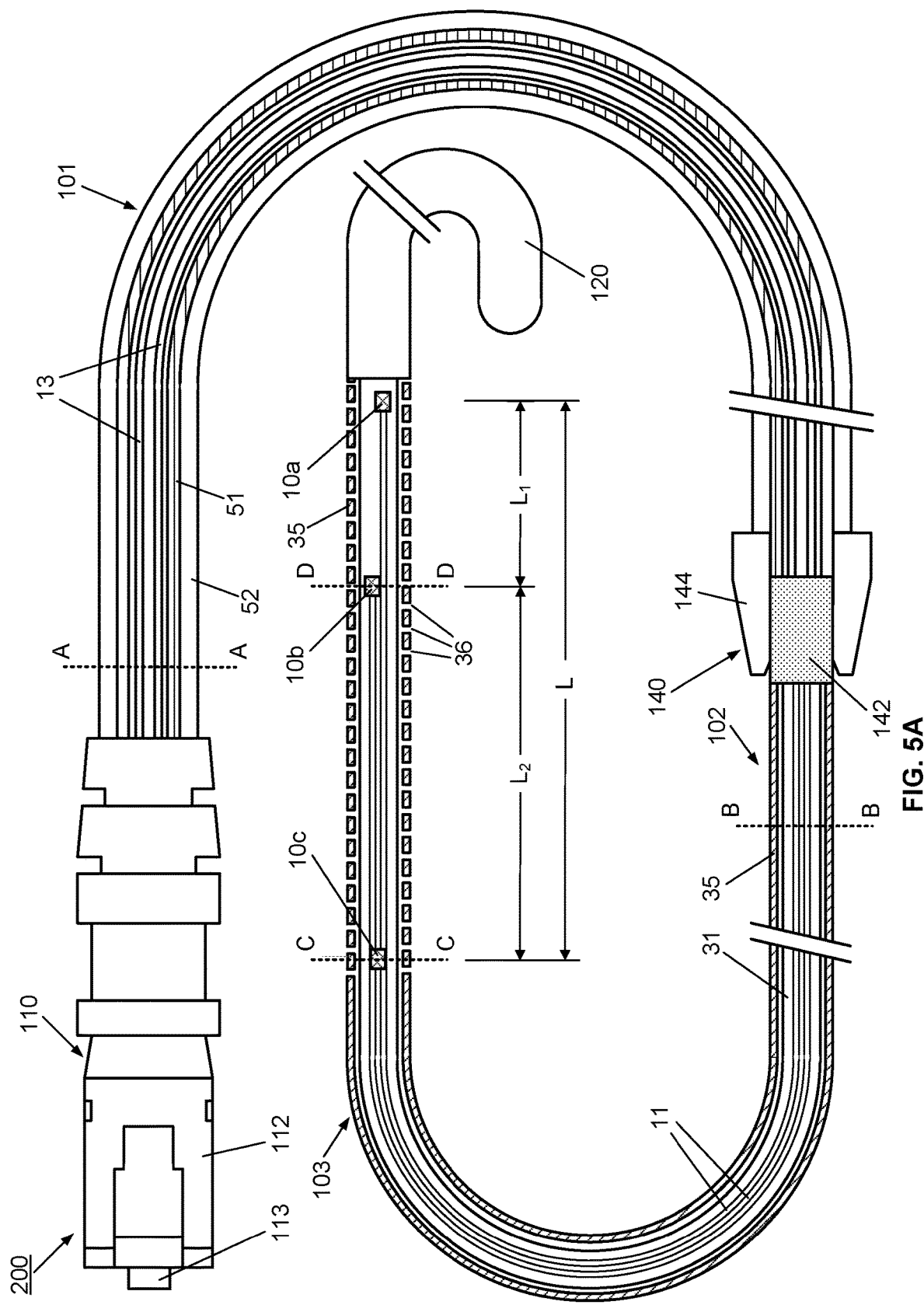

A-A CUT-THROUGH VIEW OF FIG. 5A

B-B CUT-THROUGH VIEW OF FIG. 5A

C-C CUT-THROUGH VIEW OF FIG. 5A

D-D CUT-THROUGH VIEW OF FIG. 5A

B-B CUT-THROUGH VIEW OF FIG. 5A

A-A CUT-THROUGH VIEW OF FIG. 5B

B-B CUT-THROUGH VIEW OF FIG. 5B

C-C CUT-THROUGH VIEW OF FIG. 5B

D-D CUT-THROUGH VIEW OF FIG. 5B

A-A CUT-THROUGH VIEW OF FIG. 20

B-B CUT-THROUGH VIEW OF FIG. 20

C-C CUT-THROUGH VIEW OF FIG. 20

D-D CUT-THROUGH VIEW OF FIG. 20

A-A CUT-THROUGH VIEW OF FIG. 24

B-B CUT-THROUGH VIEW OF FIG. 24

SYSTEM AND APPARATUS COMPRISING A MULTISENSOR GUIDEWIRE FOR USE IN INTERVENTIONAL CARDIOLOGY

CROSS-REFERENCE TO RELATED APPLICATIONS

This application claims priority from U.S. provisional patent application No. 62/023,891, entitled "System And Apparatus Comprising a Multisensor Support Guidewire for Use in Trans-Catheter Heart Valve Therapies", filed Jul. 13, 2014 and from U.S. provisional patent application No. 62/039,952, entitled "System And Apparatus Comprising a Multisensor Support Guidewire for Use in Trans-Catheter Heart Valve Therapies", filed Aug. 21, 2014; both applications are incorporated herein by reference in their entirety.

This application is related to PCT International Application no. PCT/IB2012/055893, entitled "Apparatus, system and methods for measuring a blood pressure gradient", filed Oct. 26, 2012, which claims priority from U.S. provisional patent application No. 61/552,778 entitled "Apparatus, system and methods for measuring a blood pressure gradient", filed Oct. 28, 2011 and from U.S. provisional patent application No. 61/552,787 entitled "Fluid temperature and flow sensor apparatus and system for cardiovascular and other medical applications", filed Oct. 28, 2011, all of which are incorporated herein by reference, in their entirety.

TECHNICAL FIELD

The present invention relates to a system and apparatus comprising a guidewire for use in interventional cardiology, e.g. for Transcatheter heart Valve Therapies (TVT), such as, for Trans-catheter Aortic Valve Implantation (TAVI) and for related diagnostic measurements.

BACKGROUND

If a heart valve is found to be malfunctioning because it is defective or diseased, minimally invasive methods are known for repair and replacement of the heart valve. Transcatheter Valve Therapies (TVT) include procedures referred to as Transcatheter Aortic Valve Implantation (TAVI) and Transcatheter Mitral Valve Implantation (TMVI).

TVT provides methods for replacing diseased valves which avoid the need for open heart surgery. Procedures such as TAVI have been developed over the last decade and have become more common procedures in recent years. While there have been many recent advances in systems and apparatus for TVT and for related diagnostic procedures, interventional cardiologists who perform these procedures have identified the need for improved apparatus for use in TVT, such as, heart valve replacement. They are also seeking improved diagnostic equipment that provides direct measurements of important hemodynamic cardiovascular parameters before, during and after TVT.

The above referenced related PCT application no. PCT/IB2012/055893 (Publication no. WO/2013/061281), having common inventorship and ownership with the present application, discloses a multisensor micro-catheter or guidewire which comprises a distal end portion containing multiple optical sensors arranged for measuring blood pressure at several sensor locations simultaneously in real-time, and optionally also blood flow. In particular, the multisensor micro-catheter or guidewire is designed for use in minimally invasive surgical procedures for measurement of intra-vascular pressure gradients, and in particular, for direct measurement of a transvalvular pressure gradient within the heart.

To obtain accurate measurements of hemodynamic parameters such as blood pressure, blood flow, a blood pressure gradient, or other parameters within the heart, it is desirable that the sensor guidewire does not interfere with normal operation of the heart and the heart valves. Thus, beneficially, a fine diameter guidewire, e.g. ≤0.89 mm diameter, with a flexible tip, facilitates insertion through a heart valve without trauma, and reduces interference with valve operation. That is, when the sensor guidewire is inserted through the valve, it preferably causes minimal interference with the movement of the valve and/or does not significantly perturb the transvalvular pressure gradient or other parameters. For example, in use, a multisensor guidewire may be introduced via the aorta, through the aortic valve, and positioned so that the optical pressure sensors are located both upstream and downstream of the aortic valve, for direct measurement of the transvalvular blood pressure gradient, and optionally also blood flow, with minimal disruption of the normal operation of the aortic valve. Accordingly, a fine gauge guidewire minimizes disruption of the heart valve activity during measurement, to obtain accurate measurements of the transvalvular pressure gradient or other parameters.

A reliable measurement of a transvalvular pressure gradient through several cardiac cycles is an important parameter to assess whether the heart valve is functioning well or malfunctioning. An optical multisensor pressure sensing guidewire of this structure provides a valuable tool that an interventional cardiologist can use to facilitate direct measurements of cardiovascular parameters, including a transvalvular pressure gradient. Such measurements provide information relating to parameters, such as, an aortic regurgitation index, stenotic valve orifice area and cardiac output.

As described in the above referenced related patent applications, typically, a support guidewire used for TVT comprises an outer layer in the form of a flexible metal coil, and a central metal core wire or mandrel. The outer metal coil and inner core wire act together to provide a suitable combination of flexibility and stiffness, which, together with a suitably shaped tip, allow the guidewire to be directed or guided through the blood vessels into the heart. In the multisensor guidewire disclosed in the above referenced PCT International Application no. PCT/IB2012/055893, the optical sensors, e.g. 3 or 4 optical pressure sensors are located in a distal end portion of the sensor guidewire, and coupled by respective individual optical fibers to an optical input/output at the proximal end of the guidewire. It will be appreciated that to fit a plurality of optical sensors and optical fibers within a guidewire comprising a small gauge (≤0.89 mm) outer coil, the diameter of core wire is made as small as possible, i.e. to allow sufficient space around the core wire to accommodate the optical fibers and sensors. However, use of a smaller diameter core wire significantly reduces the stiffness of the multisensor guidewire. That is, the optical fibers and sensors take up space within the micro-catheter or guidewire coil but do not contribute significantly to the stiffness.

In testing of prototype multisensor guidewires, it has been found that the strong blood flow and turbulence within the heart can be sufficient to displace a small-gauge flexible guidewire, and tends to push the guidewire back into the aorta. Thus, during measurement of a transvalvular pressure gradient, movement of the guidewire may create difficulty in positioning the sensors and the cardiologist may need to readjust the positioning of the guidewire to maintain the pressure sensors each side of the heart valve. On the other hand, in a multisensor guidewire of this structure, to accommodate a plurality of optical sensors and respective optical fibers around a larger diameter stiffer core wire would require a larger outside diameter outer coil, i.e. larger than 0.89 mm. While a larger gauge, stiffer guidewire would be less easily displaced during measurements, for measurement of transvalvular pressure gradients, it would tend to interfere more with normal heart valve operation, and may increase the risk of tissue damage. Accordingly, a need for further improvements has been identified.

If diagnostic measurements of hemodynamic/cardiac parameters indicate the need for valve replacement, minimally invasive TVT procedures, such as TAVI, can be performed to insert a replacement or prosthetic valve, e.g. comprising leaflets made of biologic tissue supported within an expandable metal frame.

Examples of current prosthetic valves and valve delivery systems are illustrated and described and illustrated in an article entitled "Current Status of Transcatheter Aortic Valve Replacement", by John G. Webb, MD, David A. Wood, M, Vancouver, British Columbia, Canada; *Journal of the American College of Cardiology*, Vol. 60, No. 6, 2012.

Very briefly, the procedure requires that a support guidewire, which is relatively stiff guidewire (TAVI guidewire) with a flexible tip, is introduced into the heart and through the aortic valve. For example, the interventional cardiologist introduces the support guidewire through a catheter inserted into the femoral artery, i.e. in the groin, and moves it up through the aorta into the heart. The tip of the TAVI guidewire is introduced into the aorta, through the malfunctioning aortic valve, and into the left ventricle of the heart. Once the support guidewire is anchored within the ventricle, a delivery device holding the replacement valve is passed over the support guidewire. The cardiologist guides the delivery device carrying the replacement valve over the support guidewire and manoeuvres the valve into position within the aortic valve. The replacement valve is expanded, so that the patient's malfunctioning aortic valve is pushed out of the way. The valve frame may be self-expandable or balloon-expandable, depending on the valve type and the delivery system. Once expanded, the metal frame engages the wall of the aorta and holds the replacement valve in position. When the delivery system is withdrawn, the leaflets on the replacement valve are able to unfold and then function in a manner similar to the leaflets of the natural aortic valve.

Commercial availability of an optical multisensor guidewire as described in the above referenced co-pending patent application would provide the interventional cardiologist with a useful tool for directly measuring a pressure gradient before and after such a procedure for valve repair or replacement, e.g. for TAVI. For example, it is envisaged that the interventional cardiologist would introduce the fine gauge multisensor guidewire to measure a transvalvular pressure gradient, and optionally blood flow, to assess pre-implantation functioning of the heart and the damaged or malfunctioning aortic valve. After withdrawing the multisensor guidewire, the cardiologist would perform a transcatheter heart aortic valve implantation procedure using a specialized, more robust and stiffer, support guidewire (TAVI guidewire) to deliver the valve implant into the heart and perform the implantation. Subsequently after completing the TAVI procedure the TAVI guidewire would be withdrawn. The multisensor guidewire would then be reintroduced to measure a transvalvular pressure gradient and flow, to assess post-implant functioning of the replacement valve.

For TAVI, a relatively stiff support guidewire, typically 0.035 inch or 0.89 mm in diameter, is required. For example, guidewire manufacturers may use a descriptive term, such as, "stiff" or "super stiff" to provide an indication of the guidewire stiffness. Based on experience, an interventional cardiologist will select a guidewire with an appropriate stiffness and/or other mechanical characteristics to suit a particular TVT procedure. Such a description of stiffness or flexibility can be related in mechanics to a measurement of a flexural modulus, which is a ratio of stress to strain in flexural deformation, or, what may be described as the tendency for a material to bend.

During a TAVI procedure, the support guidewire must be firmly anchored within the left ventricle so that the replacement valve can be accurately positioned and held firmly in place while it is expanded. When such a guidewire is introduced into the left ventricle of the heart through the aortic valve, if too much force is applied to the guidewire or it is pushed too far, there is some risk that the guidewire could cause damage or trauma to the heart tissues, e.g. damage to the aortic wall or ventricular perforation and pericardial effusion resulting in pericardial tamponade. Moreover, there is increased risk of trauma or damage to the heart wall in a diseased, weakened or calcified heart. To reduce risk of trauma or ventricular perforation, typically the tip of the support guidewire is relative soft and flexible. It may be pre-formed as a J-tip or it may be resiliently deformable so that it can be manually shaped as required by the cardiologist. Recently, specialized TAVI guidewires have become commercially available with pre-formed curved tips of other forms. For example, the Boston Scientific Safari™ pre-shaped TAVI guidewire has a double curve tip, and the Medtronic Confida™ Brecker Curve™ guidewire has a spiral tip. Reference is also made, by way of example, to structures described in US patent publication no. US2012/0016342 and PCT Publication no. WO2010/092347, each to Brecker, entitled "Percutaneous Guidewire"; PCT Publication no. WO2014/081942, to Mathews et al., entitled "Preformed Guidewire"; and PCT Publication no. 2004/018031 to Cook, entitled "Guidewire". See also, an article by D. A. Roy et al., entitled "First-in-man assessment of a dedicated guidewire for transcatheter aortic valve implantation", EuroIntervention 2013; 8, pp. 1019-1025.

While significant advances have recently been made, interventional cardiologists have identified a need for further improvements or alternatives to available guidewires and diagnostic tools for use in minimally invasive cardiac procedures, such as TAVI, or other TVT. In particular, it is desirable to have improved apparatus to simplify or facilitate TVT procedures, including apparatus that will assist in reducing the risk of tissue trauma, e.g. damage to the aorta, the valve or the ventricular wall when much force is exerted on the support guidewire. Additionally, improved systems and apparatus that would provide for direct (in situ) diagnostic measurements before and after TVT procedures would potentially assist in understanding factors that contribute to successful outcomes and/or issues that may contribute to mortality or need for re-intervention.

Thus, an object of the present invention is to provide for improvements or alternatives to known cardiovascular support guidewires for TVT and/or to multisensor guidewires for that enable direct measurements of cardiovascular parameters, such as a transvalvular pressure gradient.

SUMMARY OF INVENTION

The present invention seeks to mitigate one or more disadvantages of known systems and apparatus for measuring cardiovascular parameters, and/or for performing interventional cardiac procedures, including transcatheter valve therapies (TVT), such as transcatheter aortic valve implantation (TAVI).

A first aspect of the invention provides multisensor guidewire for diagnostic measurements in interventional cardiology comprising:

an outer flexible coil wire (coil) having a length extending between a proximal end and a distal end, an outside diameter of ≤1 mm, and a core wire extending within the coil from the proximal end to the distal end, the distal end comprising a flexible distal tip;

a sensor arrangement comprising a plurality of optical sensors and a plurality of optical fibers; a sensor end of each optical fiber being attached (i.e. integral with or bonded to) and optically coupled to an individual one of the plurality of optical sensors; the plurality of optical fibers extending within the coil from the proximal end to sensor locations within a distal end portion of the coil, proximal to the distal tip;

the core wire having a cross-sectional profile defining a channel means along a length of the core wire, the channel means comprising part of a surface of the core wire providing at least one channel, between a channel surface of the core wire and the coil, accommodating therein the plurality of optical sensors and their respective optical fibers;

a proximal end of each of the plurality of optical fibers being coupled to an optical input/output connector at the proximal end of the guidewire for connection to an optical control system; and the plurality of optical sensors of the sensor arrangement including two or more optical pressure sensors at respective sensor locations spaced apart along a length of the distal end portion of the core wire.

Thus a specially shaped core wire is provided which is grooved or otherwise surface channeled to position the optical fibers and their respective sensors. The plurality of optical fibers and optical sensors sit within the channel or recess formed by the channel surface of the core wire, preferably within a diameter $D_{core}$ of the core wire. For example, the channel surface comprises one groove or a plurality of grooves defined in the surface of the core wire along its length. Each groove may accommodate a single fiber and sensor, or, alternatively each groove may accommodate a plurality of fibers and sensors, within a diameter $D_{core}$ of the core wire.

The core wire may have a simpler cross-sectional profile in which the channel surface is defined by removal of a minor segment of a generally circular cross-sectional profile of the core wire, e.g. formed by grinding or wire rolling or wire drawing, to provide a cross-section having a generally D-shape or lune-shape. The optical fibers and optical sensors thus sit against, and may be bonded adhesively to the channel surface, and within the diameter $D_{core}$ of the core wire along its length.

If required, e.g. if the sensors are of larger diameter than the optical fibers, at sensor positions in the distal end portion, recesses or cavities may be formed in the core wire at sensor locations to accommodate the optical sensors. The cavities may also accommodate radiopaque markers for locating the sensors in use, e.g., by conventional radio-imaging techniques.

In an embodiment, the channel surface comprises a single contoured groove, e.g. with a shape and dimensions large enough to be formed by conventional wire-drawing or wire-rolling processes, which positions and accommodates several fibers within the diameter $D_{core}$ of the core wire.

The optical fibers are preferably adhesively bonded or otherwise fixed to the channel surface of the core wire at one or more points along the length of the core wire. Preferably, the plurality of optical sensors including two or more optical pressure sensors at sensor locations spaced apart along a length of the distal end portion of the core wire, for placement upstream and downstream of a heart valve for measuring a transvalvular pressure gradient. Optionally, the plurality of optical sensors further comprises an optical flow sensor, for measurement of blood flow.

Preferably, the material and diameter $D_{core}$ of the core wire, in at least the distal end portion, provides a flexural modulus of a predetermined stiffness to the guidewire. Typically, this stiffness may be described by guidewire manufactures using descriptors such as "stiff" or "super stiff". The stiffness may be quantified by a flexural modulus, e.g. as described in an article by G. J. Harrison et al., entitled "Guidewire Stiffness: What's in a Name?" J. Endovasc. Ther. 2011, pp. 797-801. As an example, for, a stainless steel coil and core wire providing a guidewire having an outside diameter of 0.89 mm (0.035 inch), a TAVI guidewire desirably provides a flexural modulus of at least 60 GPa or 65 GPa. That would be similar to that of an Amplatz Super Stiff™ or Ultra Stiff™ guidewires (0.89 mm or 0.035 inch) which were reported in the above referenced article to have a flexural modulus of 60 GPa and 65 GPa, respectively. For some procedures, the operator may require or prefer a guidewire in the range 60 GPa±10%, or alternatively may require a significantly stiffer guidewire. For some procedures, a more flexible guidewire may be preferred.

Where the channel surface comprises one or more grooves along the length of the core wire, the optical fibers and optical sensors preferably sit within the one or more grooves of the core wire without protruding beyond the diameter $D_{core}$ of the core wire. If required, at sensor positions in the distal end portion, the grooves may be enlarged to accommodate the optical sensors. In an embodiment, the channel means comprises a plurality of grooves spaced apart and extending along the length of the core wire. The grooves may be substantially straight along the length of the core wire. In an embodiment, the grooves comprise helical grooves, for example, helical grooves having a pitch of at least 25 mm (1 inch). Accordingly, a multisensor guidewire is provided with a grooved core wire that can accommodate multiple fibers and optical sensors while optimizing the stiffness for a guidewire of a particular diameter $D_{core}$ of the core wire and overall outside diameter of the multisensor guidewire.

For measurement of transvalvular pressure gradients, the guidewire comprises two or more optical pressure sensors. For example, it may comprise three sensors. In one embodiment, the first and second optical pressure sensors are located at more distal sensor positions spaced apart by a first distance $L_1$ and the third optical pressure sensors being at a more proximal sensor position spaced from the second optical sensor a second distance $L_2$, where $L_2>L_1$. For example $L_1$ may be about 20 mm and $L_2$ may be about 50 mm or 60 mm for placement upstream and downstream of the aortic valve, with the two more closely spaced sensors placed in the left ventricle and the other sensor placed in the aorta.

Optionally, the plurality of optical sensors further comprises an optical flow sensor for monitoring blood flow in addition to measurement of blood pressure and blood pressure gradients, e.g. to enable computation of the valve area. In one embodiment, the optical flow sensor is positioned proximally of the pressure sensors, i.e. to measure blood flow in the ascending aorta downstream of the aortic valve and before the branches from the aorta, e.g. about 50 mm to 80 mm from the aortic valve or a distance $L_{FS}$ of about 20 mm upstream from the most proximal optical pressure sensor. Multisensor guidewires of alternative embodiments, comprising other spacings of two or more pressure sensors and a flow sensor, are also disclosed.

Beneficially, the plurality of optical sensors further comprises a contact force sensor for monitoring a contact force applied to a length of the distal end portion of the guidewire, e.g. to provide feedback to the interventional cardiologist when a threshold contact force is reached and to assist in avoiding tissue trauma or perforation.

In some embodiments, to accommodate a plurality of optical sensors within a guidewire of diameter ≤0.89 mm (≤0.035 inch) and with a core wire providing a required stiffness, the number sensors may be limited to a maximum of two, three or four sensors. For example, for some applications, if only three sensors can be accommodated, it may be preferred to provide two optical pressure sensors and one flow sensor to enable measurements of a transvalvular pressure gradient and blood flow. If a fourth sensor can be accommodated, while still providing sufficient stiffness, it may be another pressure sensor, or a contact force sensor.

Where the multisensor guidewire is to be used as a support guidewire for TVT and similar procedures, to enable over-the-wire delivery of components, the multisensor guidewire comprises separable distal and proximal parts connected by a micro-optical coupler. The multisensor guidewire forms the distal part and the proximal part comprises a flexible optical coupling to the control system. Thus, distal part comprises a male connector of the optical coupler and the proximal part comprises a female connector of the optical coupler, the male connector having an outside diameter no greater than the outside diameter of the coil of the guidewire. For example, a proximal end of the core wire comprises a tapered portion that extends to form a core of the male connector and the plurality of optical fibers emerge from the grooves and extend around the tapered portion, around the core, and through a surrounding body or ferrule of the male connector which has an outside diameter of no greater than 0.89 mm. The optical coupler may further comprise alignment means and/or fastening means.

Beneficially, to assist in anchoring of the guidewire during TVT, e.g. anchoring the guidewire within the left ventricle for TAVI, the flexible distal tip comprises an atraumatic tip such as a J-tip or other pre-formed curved tip. The tip may be a pre-formed three dimensional curved structure, such as a flexible helical structure (resembling a pigtail or coiled phone cord) or a tapered helix resembling a snail shell.

Another aspect of the invention provides a sensor support guidewire apparatus comprising at least one optical sensor, wherein the guidewire comprises a separable micro-optical coupler coupling proximal and distal parts of the guidewire, to enable on/over the guidewire delivery of components. The micro-optical coupler preferably has an outside diameter no larger than the outside diameter of the guidewire coil, e.g. ≤0.89 mm.

Thus in an embodiment, the multisensor support guidewire apparatus for use in TVT, comprises separable distal and proximal parts connected by an optical coupler, wherein the distal part comprises a multisensor support guidewire; the proximal part comprises a flexible tubular member containing a plurality of optical fibers, and having at its proximal end an optical connector for coupling to the optical controller and having at its distal end the female connector of the optical coupler;

the optical input/output connector at the proximal end of the distal part forming the male part of the optical coupler and having an outside diameter no greater than that of the coil of the guidewire; and the optical coupler providing coupling of the plurality of individual optical fibers of the distal part to respective ones of the plurality of individual optical fibers of the proximal part.

Yet another aspect of the invention provides a sensor guidewire comprising another sensor, e.g. another optical sensor, located within or near a distal end of the guidewire for monitoring a contact force applied to a length of a distal end portion.

Thus, in an embodiment, a sensor support guidewire for use in TVT comprises:

a flexible coil having an outside diameter of ≤0.89 mm and a core wire extending within the coil from a proximal end to a distal end, the distal end comprising a flexible distal tip;

an optical contact force sensor comprising a Fabry-Pérot MOMS optical sensor located within a distal end portion of the guidewire;

the Fabry-Pérot MOMS optical sensor being coupled by a first optical fiber to an optical input/output connector at a proximal end of the guidewire for connection to a control system, and a diaphragm of the Fabry-Pérot MOMS optical sensor being coupled to a second optical fiber which extends through a length of the distal end portion for monitoring a contact force applied to said length of the distal end portion;

the core wire having a groove defined in its surface along a length of the core wire, the groove accommodating therein the Fabry-Pérot MOMS optical sensor and the first and second optical fibers. A system comprising a sensor guidewire with a contact force sensor allows for a control system to monitor the contact force applied to said length of the distal end portion and provides feedback to the user indicative of the contact force. The system may provide an alert when the contact force exceeds a predetermined threshold value, e.g. during insertion of the support guidewire into the left ventricle for TAVI, to assist the cardiologist in avoiding tissue trauma.

Another aspect of the invention provides a support guidewire for use in TVT having a flexible distal tip comprising a pre-formed three dimensional curved structure. The pre-formed three dimensional curved structure assists in placement and anchoring of the support guidewire in the region of interest. It may comprise a pre-formed helix or a tapered helix resembling a snail shell.

Another aspect of the present invention provides core wire for a sensor guidewire comprising an outer flexible coil wire of outside diameter of 1 mm or less, the core wire having a diameter $D_{core}$ to fit within the outer flexible coil wire, and the core wire having a cross-section profiled defining a channel means along a length of the core wire, the channel means comprising part of a surface of the core wire comprising a channel surface recessed within the diameter $D_{core}$ and extending along the length of the core wire for accommodating or more optical fibers within the diameter $D_{core}$ of the core wire. The core wire preferably comprises a suitable medical grade stainless steel having appropriate mechanical properties for a core wire. In axial cross-section, core wire has a generally circular cross section of outer radius $R_1$. The channel surface may be a plurality of straight or helical grooves along the length of the core wire, having dimensions which accommodate one or more optical fibers within the outer radius $R_1$ of the core wire. In other embodiments, the channel surface may comprises a single groove along the wire for accommodating multiple fibers and sensors, e.g. a core wire having a D-shaped profile formed by grinding a round wire, or a cross-sectional profile defined by wire-rolling or wire-drawing. The groove may be contoured to accommodate multiple fibers. For example, the cross-sectional structure of the wire may be generally circular, having a major portion (circle sector) of outer radius $R_1$ and a minor portion (circle sector) of outer radius $R_2$, where $R_2<R_1$ and $R_1-R_2 \geq D_F$ the diameter of the fiber to be accommodated, allowing for a clearance $C_L$ for radii tolerances. The arc or width w of the minor portion is sufficient to accommodate the plurality of fibers side by side circumferentially. In one embodiment, the radius of the boundary or edge between the major and minor portions is defined by a curved surface with an external edge radius $R_{ext}$ which meets a minimum, e.g. 0.005 inch, for formation of the channel surface by known wire rolling and wire drawing processes.

The contoured groove may alternatively be described as comprising ridges and furrows to accommodate the plurality of optical fibers. The ridges and furrows are radiused to position the optical fibers side by side, with centres of the optical fibers at similar radii relative to the centre of the core wire, and with the fibers accommodated within the outer diameter of the core wire. The ridges and furrows are also radiused to meet a minimum requirement for manufacturing by wire rolling or wire drawing. For example, as shown in the cross-sectional view through the guidewire, to accommodate three optical fibers, the groove has two furrows to accommodate two of the fibres and the third fiber rests on ridge in between. Preferably, the center ridge, outer ridges, and furrows are suitably radiused to enable the shape of the channel surface to be manufactured economically using known wire forming processes.

A core wire of this structure can be more readily manufactured using existing wire rolling equipment and thus can be manufactured at a more reasonable cost for use in disposable multisensor guidewires. A core wire of this shape can be used with conventional outer flexible coils. A plurality of small diameter optical fibers can thus be adhesively bonded to the core wire along its length, and accommodated within the inner diameter of the outer flexible coil, while still providing a core wire of a required stiffness. The channel surface may comprise a plurality of grooves along the length of the core wire, each groove accommodating an individual optical fiber. The plurality of grooves may be generally straight, or have some rotation along the length of the core wire, e.g. be helical grooves. Alternatively the channel surface may be a single groove that accommodates the plurality of optical fibers, e.g. side by side. For example, for three optical pressure sensors and three optical fibers, in embodiments of the invention, the core wire has a channel surface having a simple ground groove or a contoured groove, e.g. comprising two furrows and a ridge in between. The channel surface may be generally straight and parallel to the length of the wire, or have some rotation about the axis along the length of the core wire, e.g. depending on manufacturing constraints.

Thus, apparatus, systems and methods are provided that mitigate one or more problems with known systems and apparatus for TVT, and in particular, some embodiments provide a multisensor guidewire which can be used for both TVT procedures and for direct measurement of hemodynamic parameters such as intravascular or transvalvular pressure gradients and flow, before and after TVT procedures.

The foregoing and other objects, features, aspects and advantages of the present invention will become more apparent from the following detailed description, taken in conjunction with the accompanying drawings, of embodiments of the invention, which description is by way of example only.

BRIEF DESCRIPTION OF THE DRAWINGS

In the drawings, identical or corresponding elements in the different Figures have the same reference numeral.

FIG. 5A illustrates schematically a longitudinal cross-sectional view of an apparatus comprising a multisensor guidewire comprising a plurality of optical sensors according to a second embodiment of the present invention;

DETAILED DESCRIPTION OF EMBODIMENTS

A system and apparatus comprising a multisensor guidewire for use in interventional cardiology, which may include diagnostic measurements of cardiovascular parameters and/or TVT, according to an embodiment of the present invention will be illustrated and described, by way of example, with reference to a system for use in a TAVI procedure, for aortic valve replacement.

Figure 1:
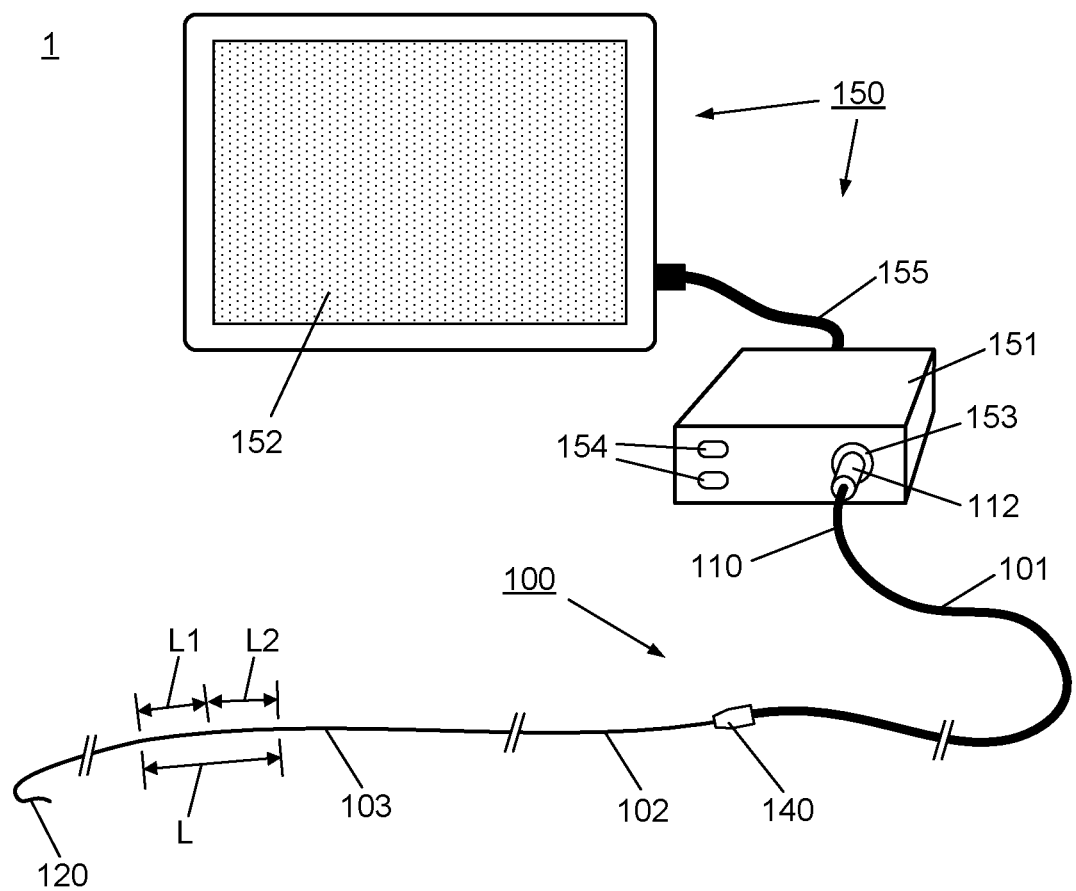
FIG. 1 illustrates schematically a system according to a first embodiment, comprising a multisensor guidewire apparatus optically coupled to a control unit.

Firstly, referring to FIG. 1, this schematic represents a system 1 comprising an apparatus 100 comprising a multisensor guidewire for use in TVT procedures, coupled to a control system 150, which houses a control unit 151 and user interface, such as the illustrated touch screen display 152. The apparatus 100 comprises a proximal part 101 and distal part 102. The distal part 102 takes the form of a multisensor guidewire and comprises components of a conventional guidewire comprising an outer layer in the form of a flexible fine metal coil 35 and an inner mandrel or core wire 31 within the outer coil 35. The outer coil 35 and the core wire 31 each have a diameter and mechanical properties to provide the required stiffness to act as a "support guidewire" for TAVI, i.e. for over-the-wire delivery of a replacement valve. Typically, for TAVI, the coil has an outside diameter of 0.035 inch or 0.89 mm or less, the guidewire has a suitable stiffness for transcatheter or intra-vascular insertion, and extends to distal tip 120, such as a flexible J-tip, or other atraumatic curved tip, to facilitate insertion. To provide the appropriate stiffness and mechanical properties, coil 35 and core wire 31, are typically stainless steel, although other suitable metals or alloys may alternatively be used. The distal part 102 differs from a conventional guidewire in that internally, it also contains a sensor arrangement 130 (not visible in FIG. 1) comprising a plurality of optical sensors 10, i.e. 10a, 10b and 10c, located within a length L of the distal end portion 103, near the distal tip 120. For example, as will be described in detail with reference to FIGS. 2 and 3, three optical sensors may be provided in the distal end portion 103 spaced by distances $L_1$ and $L_2$. Thus, internally, the distal part 102 also provides optical coupling of the optical sensors, through a plurality of optical fibers 11, to an optical coupler 140 at its proximal end, as will also be described in detail with reference to FIGS. 2, 3, 4A, 4B, 4C and 4D.

The proximal part 101 of the apparatus 100 provides for optical coupling of the distal part 102 to the control unit 151. The proximal part 101 has at its proximal end 110 an optical input/output 112, such as a standard type of optical fiber connector which connects to a corresponding optical input/output connector 153 of the control unit 151. Thus the proximal part 101 is effectively an elongate, flexible optical coupler, e.g. a tubular flexible member containing a plurality of optical fibers, with the optical coupler 140 at its distal end for optical coupling of the distal part 102, i.e. the multisensor guidewire. The control unit 151 houses a control system comprising a controller with appropriate functionality, e.g. including an optical source and an optical detector, a processor, data storage, and optical source and optical detector, and provides a user interface, e.g. a keypad 154, and touch screen display 152, suitable for tactile user input, and for graphical display of sensor data. The user interface cable 155 (typically a standard USB cable) is used to transfer data between the control unit 151 to the touch screen display 152.

The internal structure of the multisensor guidewire apparatus 100 will now be described in more detail with reference to FIGS. 2 and 3.

Figure 2:
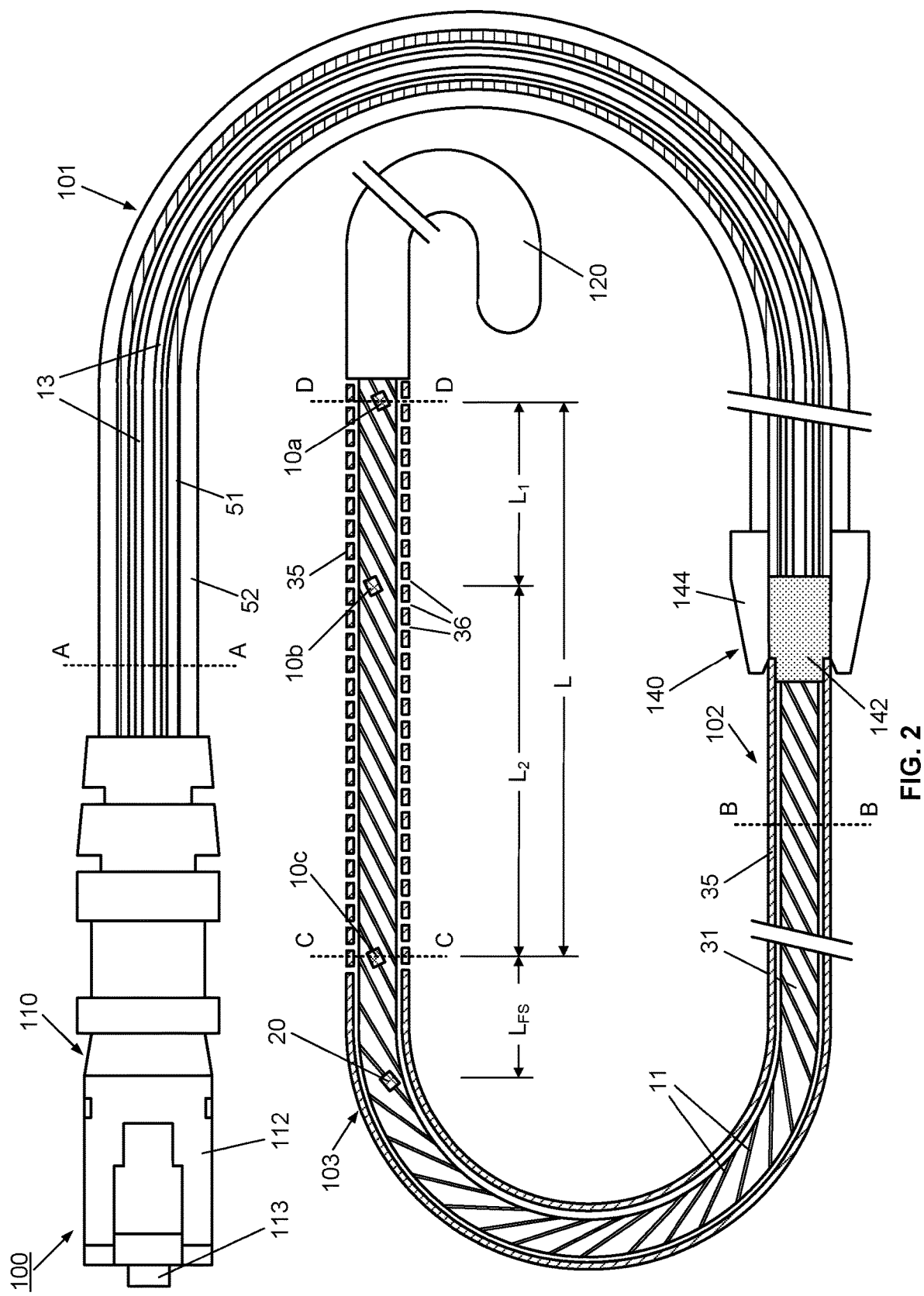
FIG. 2 illustrates schematically a longitudinal cross-sectional view of an apparatus comprising a multisensor guidewire comprising a plurality of optical sensors according to a first embodiment of the present invention.

FIG. 2 illustrates schematically a longitudinal cross-sectional view of the apparatus 100 according to the first embodiment of the invention, comprising a multisensor guidewire. The apparatus 100 extends from the optical input/output connector 112 at the proximal end 110 through the proximal part 101 to the distal part 102 which extends to the distal tip 120. If required, the outer coil of guidewire may have a coating of a suitable biocompatible hydrophobic coating such as PTFE or silicone.

The distal part 102 takes the form of a multisensor guidewire and comprises components of a conventional guidewire comprising an outer layer in the form of a flexible fine metal coil 35 and an inner mandrel or core wire 31 within the outer coil 35. The outer coil 35 and the core wire 31 each have a diameter and mechanical properties to provide the required stiffness to act as a guidewire for TAVI. Typically, for TAVI, the coil has an outside diameter of 0.035 inch or 0.89 mm or less. To provide the appropriate stiffness and mechanical properties, coil 35 and core wire 31, are typically stainless steel, although other suitable metals or alloys may alternatively be used.

In this embodiment, the sensor arrangement 130 (not visible in FIG. 2) comprises a plurality of optical sensors, i.e. three optical pressure sensors 10a, 10b, 10c arranged along a length L of a distal end portion 103 near the distal tip 120. Each of the optical pressure sensors is optically coupled to a respective individual optical fiber 11. Optionally, another type of optical sensor, e.g. an optical flow sensor 20, may be provided in or near the distal end portion 103, and coupled to another respective optical fiber 11.

For example, for measuring a transaortic pressure gradient, the optical pressure sensors 10a, 10b, 10c are arranged spaced apart by distances $L_1$ and $L_2$, e.g. 20 mm and 50 mm to 60 mm respectively, for placement of the sensors upstream and downstream of the aortic valve. Optionally, a flow sensor 20 (see FIGS. 2 and 5B) is positioned to measure flow in the aorta before the main branches from the aorta, e.g. in the ascending aorta, about 50 mm to 80 mm downstream of the aortic valve 511 or a distance $L_{FS}$ of about 20 mm from the nearest pressure sensor 10b or 10c (see FIGS. 2, 5B, 11A and 11B).

To accommodate the plurality of optical sensors 10a, 10b, 10c and 20 and their respective optical fibers 11 while maintaining the required stiffness to the guidewire, the core wire is provided with a corresponding plurality of helical grooves 32. The helical grooves 32 extend along the length of the core wire 31 from the optical coupler 140 to near the distal tip 120. The helical grooves 32 are sized to accommodate the optical fibers along the length of the distal part 102 and accommodate the optical sensors at sensor locations spaced apart along the length L of the distal end portion 103, as shown in more detail in FIG. 3.

Figure 3:
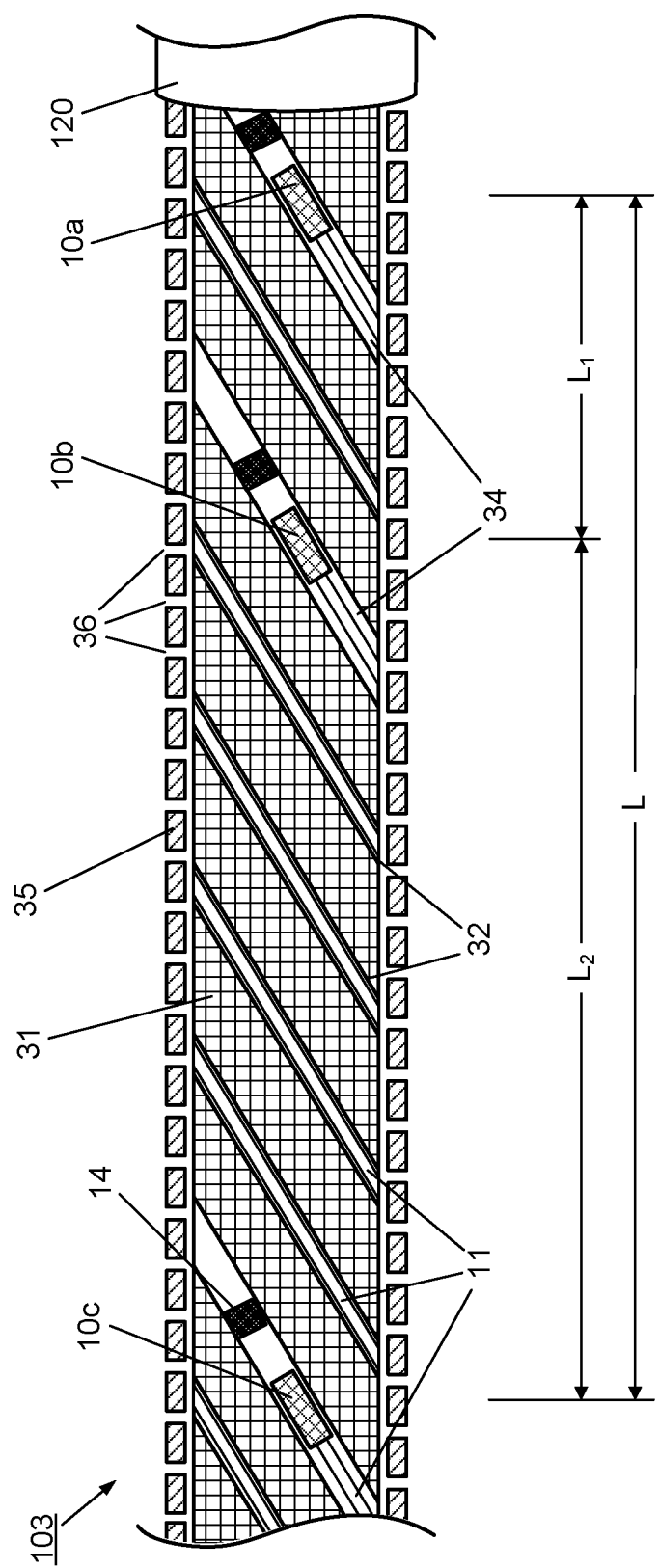
FIG. 3 illustrates schematically an enlarged longitudinal cross-sectional view showing details of the distal end portion of the multisensor guidewire illustrated in FIG. 2.

FIG. 3 shows an enlarged longitudinal cross-sectional view of the distal end portion 103 of the multisensor guidewire 100 illustrated in FIG. 2. As illustrated, the multisensor guidewire 100 is capable of measuring blood pressure simultaneously at several points, in this case three points, using the three optic fiber-based pressure sensors 10a, 10b, 10c arranged along the length L of the distal end portion 103 of the multisensor guidewire. For TAVI, the sensor locations are arranged to allow for the optical pressure sensors to be placed upstream and downstream of the aortic valve during measurements.

Accordingly, in this embodiment, the two more distal sensors 10a and 10b are spaced apart by a distance $L_1$ and sensors 10b and 10c are spaced apart by a distance $L_2$, where $L_2 > L_1$. The dimensions and pitch/angle of the helical grooves 32 in the surface of the core wire 31 are selected to accommodate the fibers 11 in channels between the core wire 31 and coil 35. Preferably, the grooves are sized so that the optical sensors 10a and 10b and the optical fibers 11 do not protrude beyond the external diameter of the core wire 31. Each sensor and optical fiber may be fixed to the core wire, e.g. adhesively fixed to the core wire, at one or more points. For example, during assembly, optical fibers 11 are inserted into the grooves 32 and held in place in the grooves 32 in the core wire 31, e.g. with a suitable biocompatible and hemocompatible adhesive, before the core wire is inserted into the coil wire 35. To accommodate the sensors 10a, 10b, 10c and 20, which may be larger in diameter than the optical fibers 11 themselves, if required, each groove 32 may be enlarged in the region where the sensor is located, i.e. at each sensor location. The guidewire coil 35 may be more loosely coiled, or otherwise structured, in the distal end portion 103 to provide apertures 36 between the coils of the wire of the guidewire coil near each of the optical pressure sensors that allow for fluid contact with the optical pressure sensors 10 (i.e. 10a, 10b, 10c).

Also, a marker, such as a radiopaque marker 14 is provided near each sensor, e.g. placed in the helical groove 32 distally of the sensor, to assist in locating and positioning the sensors in use, i.e. using conventional radio-imaging techniques when introducing the guidewire and positioning the sensors in a region of interest, e.g. upstream and downstream of the aortic valve. The radiopaque markers 14 are preferably of a material that has a greater radiopacity than the material of the core wire. For example, if the core wire 31 and outer coil 35 are stainless steel, a suitable heavy metal is used as a radiopaque marker, e.g. barium or tantalum. If required, the guidewire may have a coating of a suitable biocompatible hydrophobic coating such as PTFE or silicone.

Figure 4A:
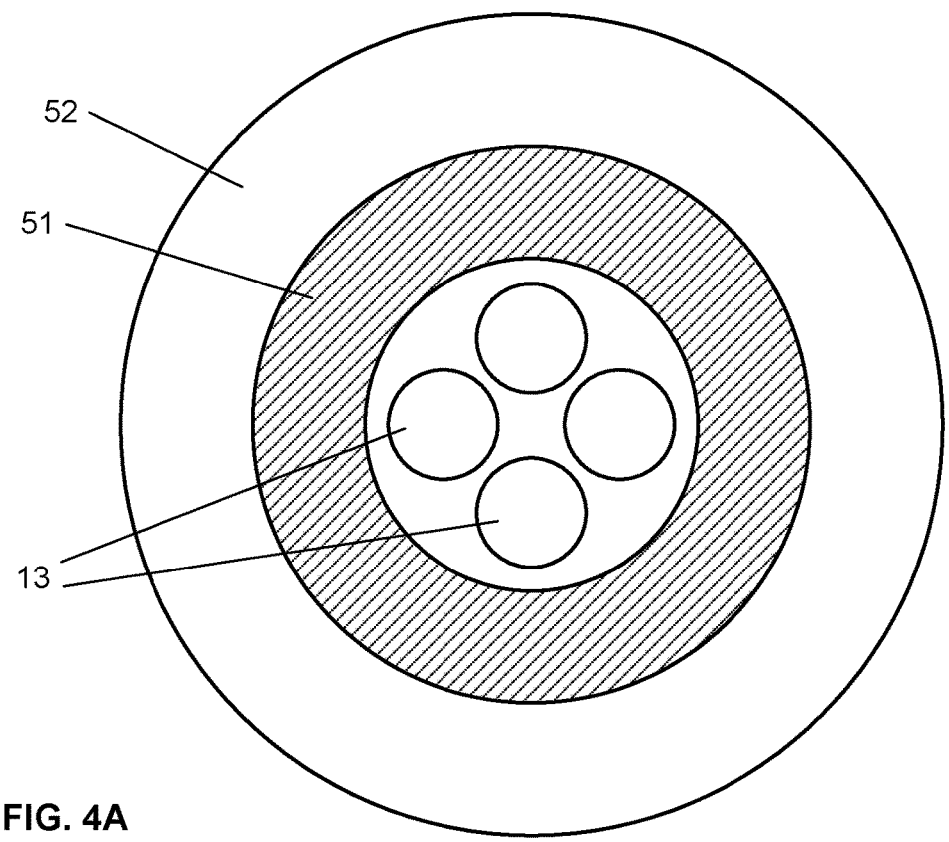
FIGS. 4A, 4B, 4C and 4D show enlarged axial cross-sectional views of the multisensor guidewire illustrated in FIG. 2 taken through planes A-A, B-B, C-C and D-D respectively.
Figure 4B:
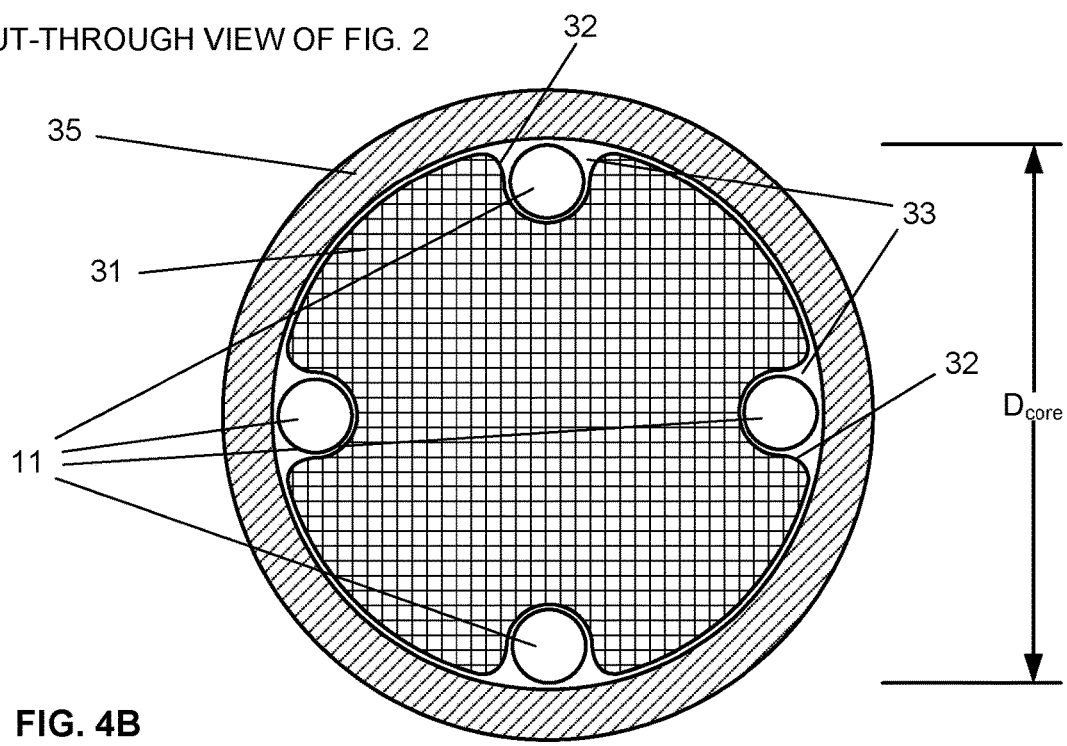
Figure 4C:
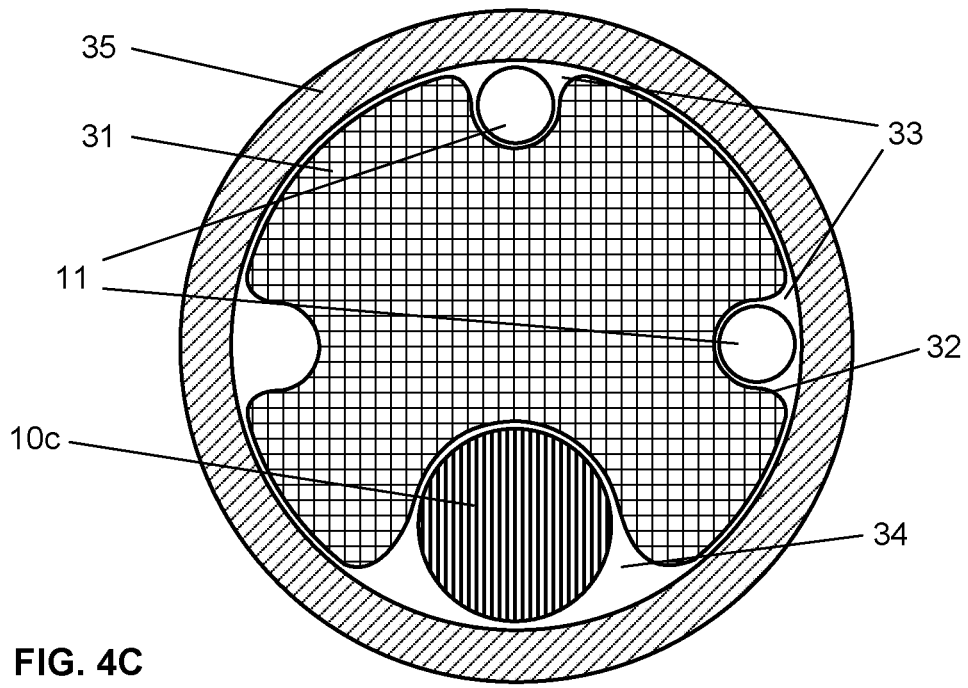
Figure 4D:
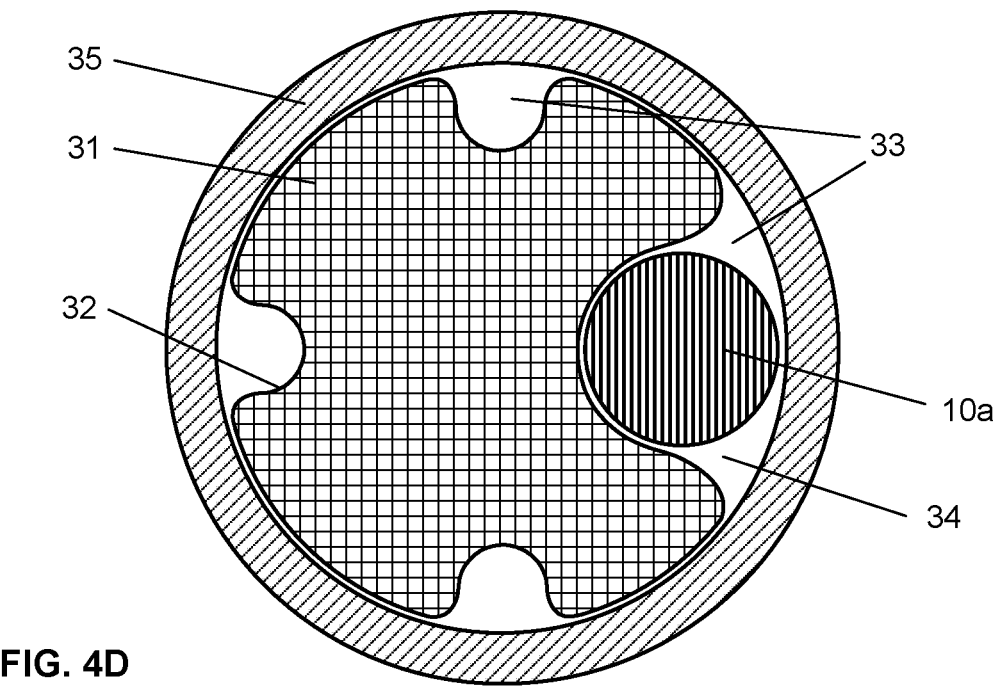

FIGS. 4A, 4B, 4C and 4D show enlarged axial cross-sectional views of the multisensor guidewire 100 taken through planes A-A, B-B, C-C and D-D respectively, of FIG. 2. FIG. 4A shows the optical fibers 13 with tubing 51 and jacket 52 of the proximal part 101. FIGS. 4B, 4C and 4D show the core wire 31 within the outer coil 35 to illustrate the location of the optical fibers 11 in grooves 32, and the location of pressure sensors 10a, 10b, 10c within enlarged groove portion 34 of the grooves 32 in the core wire 31.

Since the optical fibers do not contribute significantly to the stiffness of the guidewire, for superior stiffness required for a support guidewire of a given outside diameter, e.g. 0.89 mm, the outside diameter core wire is preferably as large as can be reasonably be accommodated within the inside diameter of the outer coil of the guidewire, allowing the required clearance between the core wire and the outer flexible coil. Accordingly, the helical grooves 32 in the core wire preferably have a minimal size to accommodate the optical fibers and sensors within the grooves and within the diameter $D_{core}$ of the core wire. In this context, by convention, the wire gauge or diameter D of a wire refers to the diameter D of the circle into which the wire will fit. It will be appreciated that the maximum diameter $D_{core}$ must also fit within the inside diameter of the outer flexible coil of the guidewire, with an appropriate clearance between the core wire and optical fibers and sensors and the coil, which is, for example, at least 1 mil or 25 microns.

The helical form of the grooves 32 reduces longitudinal and point stresses/strains in the individual fibers when the guidewire is flexed. For example, if the grooves were straight along the length of the fiber, when the guidewire is flexed, fibers on the inside curve of the bend would be subject to more compressive forces and fibers on the outside of the curve would be subject to more tensile forces. While the ends of the fibers and the sensors may be adhesively fixed to the core wire within the grooves 32, or at one or more intermediate points, when the guidewire is flexed, the helical structure of the grooves tends to spread compressive and tensile forces over a length of each fiber and reduces localized stresses and strains. Desirably, to optimize the core wire stiffness relative to the outside diameter of the guidewire, i.e. of the outer coil, there is a minimal required spacing between the core wire 31 and the coil 35 and so the helical grooves accommodate the optical fibers and sensors without protruding beyond the diameter $D_{core}$ of the core wire, as illustrated in the schematic cross-sectional view shown in FIG. 4B. As mentioned above, if needed, the grooves are enlarged to form a recess or cavity 34 in the sensor locations, as illustrated schematically in FIGS. 4C and 4. FIG. 4A shows a corresponding cross-sectional view through the proximal portion 101, which comprises the bundle of optical fibers 13 contained within flexible tubing 51 and jacket 52.

Since the proximal part 101 simply provides a flexible optical coupling to the control unit 150, it does not the same stiffness as the distal part 102 comprising the guidewire, and thus does not need to include a core wire. Although in FIG. 2 the structure of the multisensor assembly is shown in cross-section along its length from the connector 112 to the distal tip 120, for simplicity, the internal structure of the connector 112 is not shown. It will be appreciated that the optical fibers 13 of the proximal part 101 extend through the connector 112 to optical inputs/outputs 113 of the connector, as is conventional.

The optical pressure sensors 10a, 10b and 10c are preferably Fabry-Pérot Micro-Opto-Mechanical-Systems (FP MOMS) pressure sensors. As an example, a suitable commercially available FP MOMS pressure sensor is the Fiso FOP-M260. These FP MOMS sensors meet specifications for an appropriate pressure range and sensitivity for blood pressure measurements. They have an outside diameter of 0.260 mm (260 µm). Typically, they would be coupled to an optical fiber with an outside diameter of 0.100 (100 µm) to 0.155 mm (155 µm). Accordingly, the helical grooves would have a depth of 0.155 mm along their length with an enlarged depth of 0.260 mm at each sensor location. The pitch of the helical grooves is 25 mm (1 inch) or more to reduce stress on the optical fibers.

The optional optical flow sensor 20 preferably comprises an optical thermoconvection flow sensor, e.g. as described in U.S. patent application Ser. No. 14/354,588.

As illustrated schematically in FIGS. 4B to 4D, assuming the coil 35 has an outside diameter of 0.89 mm (0.035 inch) including any coating, and is formed from 0.002 inch thick coil wire, to provide an inside diameter of about 0.787 mm (0.031 inch), then a core wire having a maximum outside diameter of about 0.736 mm (0.029 inch) could be accommodated within. Preferably the coil and the core of the guidewire are made from stainless steel having high stiffness, e.g. 304V stainless steel, or other types of stainless steel for medical applications. Other biocompatible metal alloys with suitable mechanical characteristics may alternatively be used.

The helical grooves 32 will somewhat reduce the stiffness of the core wire relative to a conventional cylindrical core wire structure, but the grooved core wire structure accommodates multiple optical fibers and sensors while optimizing the stiffness for a given diameter guidewire.

By comparison, to accommodate a plurality of similarly sized optical fibers and sensors in a cylindrical space between a conventional core wire and the outer coil, the core wire diameter would have to be reduced to about 0.5 mm to accommodate the fibers, and even further reduced in the sensor locations to accommodate the sensors. Since the stiffness of a core wire varies as the fourth power of the diameter, such a reduction in the core wire diameter significantly reduces the stiffness of the guidewire. While the helical grooves in the core will somewhat reduce the stiffness of the core wire, they will do so by a far less significant factor than using a smaller diameter core wire.

When helical grooves are provided to accommodate the fibers and the optical sensors, and the pitch of the helix may be 25 mm (1 inch) or more, for example. In alternative embodiments (not illustrated) the grooves in the guidewire run straight along the length of the guidewire.

The multisensor support guidewire apparatus 100 is preferably also capable of measuring blood flow, since quantification of blood flow restriction is related to the pressure difference/gradient and the blood flow velocity. Thus, optionally, it includes an integral fiber-optic flow sensor 20 (see FIGS. 2 and 5B) at a suitable position in or near the distal end portion 103 to measure the blood flow velocity. The optical flow sensor may for example comprise an optical thermoconvection sensor or other suitable optical flow sensor.

The guidewire coil 35 together with the mandrel or core wire 31 provide the torquable characteristics of the multisensor guidewire 100 so that is capable of being shaped or flexed to traverse vascular regions in the same manner as a conventional guidewire. To facilitate insertion, the distal tip 120 extends beyond the distal end portion 103 containing the pressure sensors 10a, 10b, 10c and optional flow sensor 20, and the tip 120 may be a flexible pre-formed J tip or other appropriate atraumatic tip such as a resiliently deformable or flexible curved tip which is preformed or can be manually shaped. Typically the tip is contiguous with the guidewire. That is, the fine wire coil 35 extends along the length of the tip to a rounded end, and the core wire 31 is thinned within the tip to increase the flexibility of the tip relative to the main part of the support guidewire 102. The tip 120 may comprise a coating that can be pre-formed into a desired curved shape, e.g. a thermoplastic coating that can be thermoformed into a desire shape. The core wire 31 has a maximum possible diameter within the coil 35 within distal end portion 103 that contains the sensors (e.g. see FIGS. 4B, 4C, and 4D) so that the distal part 102 of the guidewire has sufficient stiffness to act as a support guidewire for TVT.

For operation of the optical sensors, the micro-coupler 140 couples the distal part 102 forming the multisensor guidewire to the proximal part 101 which provides optical coupling to the control unit 151 for controlling operation of the optical sensors 10 and 20. The proximal part 101 simply provides a flexible optical coupling of the distal part of the guidewire 102 to the control unit 151. Thus the proximal part 101 can have any suitable diameter and flexibility. It is not required to have guidewire elements, i.e. a coil 35 and core wire 31 to provide specific mechanical properties of a guidewire. Thus the proximal part may be more similar to a lower cost optical fiber cable, e.g. a bundle of plurality of optical fibers 13 enclosed within a tubular covering layer 51, e.g. single layer or multilayer tubing similar to catheter tubing. If required, it is protected by a thicker protective outer jacket or sleeve 52 for mechanical strength/reinforcement and to facilitate handling. The optical fibers 13 in the proximal part are optically coupled to connector 112 at the proximal end 110 and to micro optical coupler 140 at the distal end.

The optical fibers 11 in the distal part 102 reduce the cross-section area of the core wire 31 therefore significantly reducing stiffness of the guidewire 102. It will be appreciated that the use of specialized higher cost optical fibers 11 with a smaller diameter improves the stiffness of the guidewire 102. While, the use of standard lower cost optical fibers 13 with a larger diameter, e.g. optical fibers used for telecommunication, in the proximal part 101 reduces the guidewire 100 total cost without limiting its capabilities and performance for TVT procedures.

A multisensor guidewire 200 of a second embodiment is illustrated in FIG. 5A. Many elements of the multisensor guidewire 200 are similar to those of the multisensor guidewire 100 illustrated in FIGS. 2 and 3 described above, and like parts are numbered with the same reference numeral. However, in this embodiment, the core wire 31 has a cross-sectional profile which comprises a channel surface 132 in the form of a contoured or grooved structure along its length to provide a guidewire having an axial cross-section as illustrated in FIGS. 7B, 7C and 7D. The grooved structure 132 accommodates a plurality of sensors 10a, 10b, 10c coupled to respective optical fibers 11, within the diameter $D_{core}$ of the core wire.

Referring to FIG. 5A, the apparatus 200 comprises a proximal part 101 and distal part 102. The distal part 102 takes the form of a multisensor guidewire and comprises components of a conventional guidewire comprising an outer layer in the form of a flexible fine metal coil 35 and an inner mandrel or core wire 31 within the outer coil 35. The outer diameter and mechanical properties of both the outer coil 35 and the core wire 31 are selected to provide the required stiffness to act as a guidewire for TAVI. Typically, for TAVI, the coil has an outside diameter of 0.035 inch or 0.89 mm or less, the guidewire has a suitable stiffness for transcatheter or intra-vascular insertion, and extends to distal tip 120, such as a flexible J-tip, or other atraumatic curved tip, to facilitate insertion. To provide the appropriate stiffness and mechanical properties, coil 35 and core wire 31, are typically stainless steel, although other suitable metals or alloys may alternatively be used.

The distal part 102 contains a sensor arrangement comprising a plurality of optical sensors 10a, 10b, 10c located within a length L of the distal end portion 103, near the distal tip 120. Internally, the distal part 102 provides optical coupling of the optical sensors, through a plurality of optical fibers 11, to an optical coupler 140 at its proximal end, as will also be described in detail with reference to FIGS. 6, 7A, 7B, 7C and 7D.

The proximal part 101 of the apparatus 200 provides for optical coupling of the distal part 102 to the control unit 151 (e.g. see FIG. 1). The proximal part 101 has at its proximal end 110 an optical input/output 112, such as a standard type of optical fiber connector which connects to a corresponding optical input/output connector port 153 of the control unit 151. Thus the proximal part 101 is effectively an elongate, flexible optical coupler, e.g. a tubular flexible member containing a plurality of optical fibers, with the optical coupler 140 at its distal end for optical coupling of the distal part 102, i.e. the multisensor guidewire.

Figure 6:
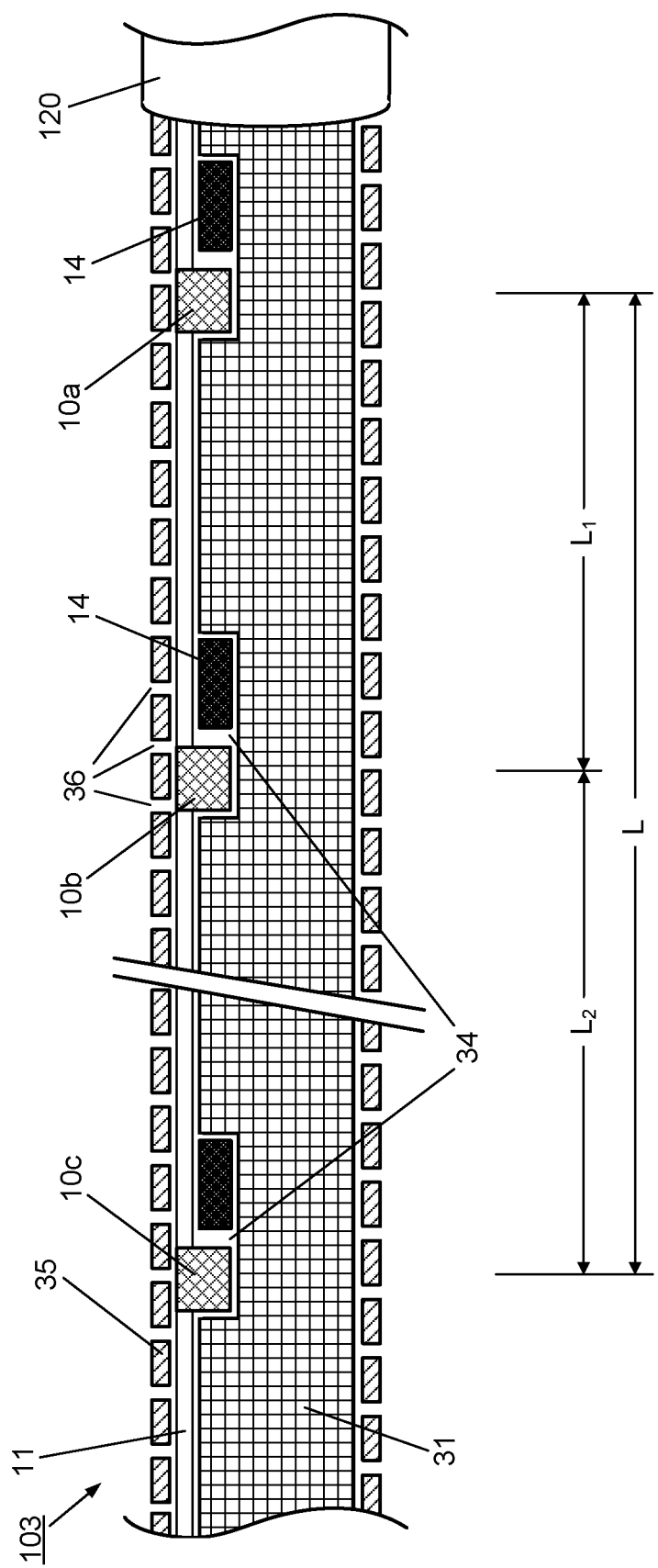
FIG. 6 illustrates schematically an enlarged longitudinal cross-sectional view showing details of the distal end portion of the multisensor guidewire illustrated in FIG. 5A.

As shown in more detail in the enlarged longitudinal cross-sectional view in FIG. 6 the three optical sensors 10a, 10b and 10c, coupled to respective optical fibers, are located in the distal end portion 103, near the distal tip 120. The sensors 10a, 10b and 10c are spaced by distances $L_1$ and $L_2$. Also, a marker, such as a radiopaque marker 14 is provided near each sensor, to assist in locating and positioning the sensors in use, i.e. using conventional radio-imaging techniques when introducing the guidewire and positioning the sensors in a region of interest, e.g. upstream and downstream of the aortic valve. The radiopaque markers 14 are preferably of a material that has a greater radiopacity than the material of the core wire. For example, if the core wire 31 and outer coil 35 are stainless steel, a suitable heavy metal is used as a radiopaque marker, e.g. barium or tantalum. If required, the outer coil of guidewire may have a coating of a suitable biocompatible hydrophobic coating such as PTFE or silicone.

For example, for measuring a transaortic pressure gradient, the optical pressure sensors 10a, 10b, 10c are arranged spaced apart by distances $L_1$ and $L_2$, e.g. 20 mm and 60 mm respectively, for placement of the sensors upstream and downstream of the aortic valve. Optionally, a flow sensor 20 (see FIG. 2) is positioned to measure flow in the aorta before the main branches from the aorta, e.g. in the ascending aorta, about 50 mm to 80 mm downstream of the aortic valve 511 or a distance $L_{FS}$ of about 20 mm from the nearest pressure sensor 10b or 10c (see FIGS. 2, 5B, 11A and 11B).

Figure 5B:
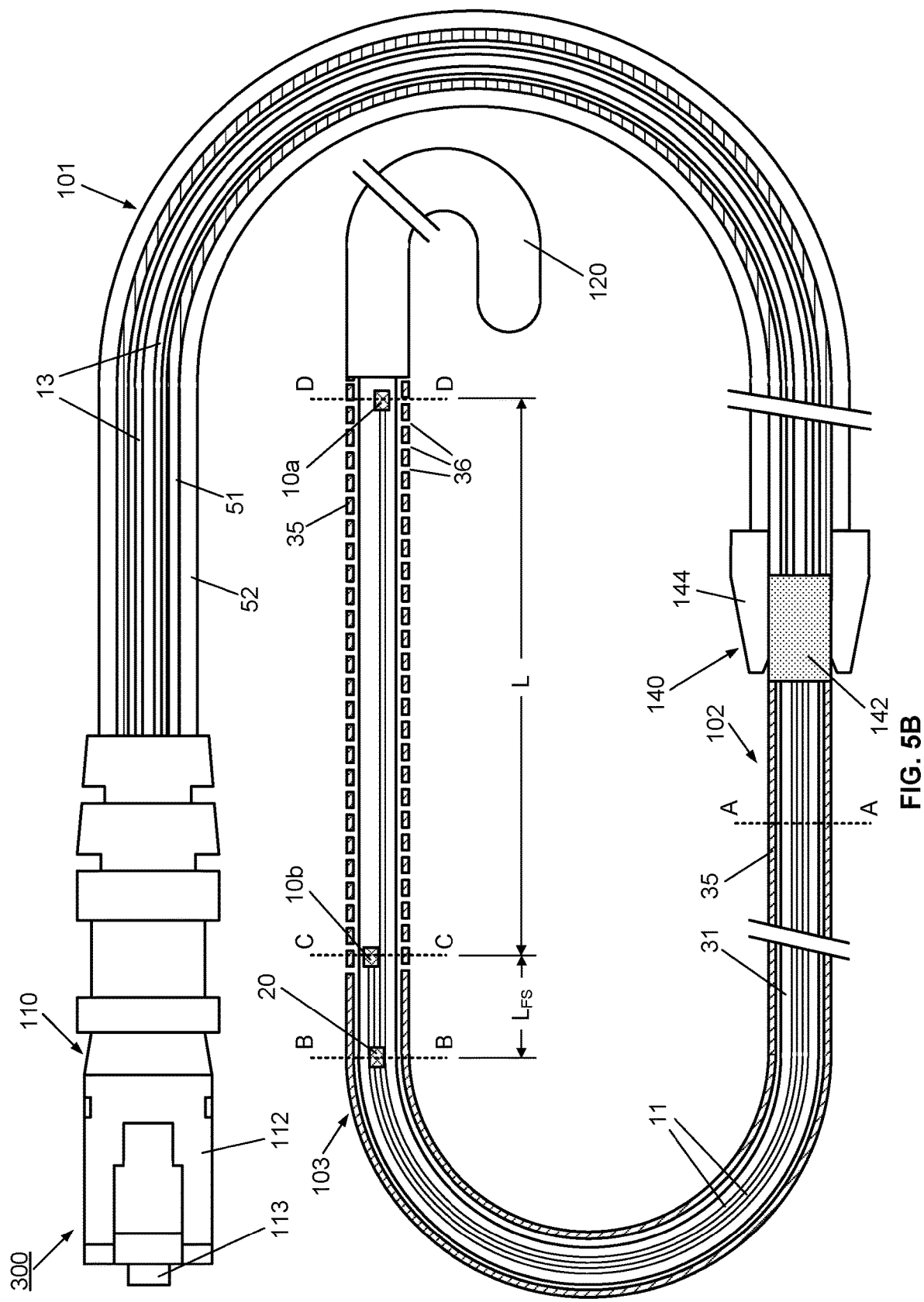
FIG. 5B illustrates schematically a longitudinal cross-sectional view of an apparatus comprising a multisensor guidewire comprising a plurality of optical sensors according to a third embodiment of the present invention.

Alternatively, as illustrated in FIG. 5B, a guidewire 300 of a third embodiment when three optical sensors can be fitted within the required diameter, the sensors comprise two optical pressure sensors 10a and 10b, and a flow sensor 20, proximal to the pressure sensors 10a and 10b. This embodiment will be described in more detail below with reference cross-sectional views shown in FIGS. 9A, 9B, 9C and 9D.

Referring back to the multisensor guidewire 200 of the second embodiment shown in FIG. 5A, the optical pressure sensors 10a, 10b, 10c and their respective optical fibers 11 lie in the grooved structure 132 as illustrated schematically in the cross-sectional views shown in FIGS. 7B, 7C and 7D. To accommodate optical sensors 10a, 10b, 10c and their respective optical fibers 11, while maintaining the required stiffness to the guidewire, the core wire has a grooved structure 132 as shown in the axial cross-sectional views in FIGS. 7B, 7C and 7D. The grooved structure 132 extends along the length of the core wire 31 from the optical coupler 140 to near the distal tip 120.

The dimensions of the grooved structure 132 in the surface of the core wire 31 are selected to accommodate the fibers 11 in between the core wire 31 and coil 35. Preferably, the grooved structure 132 is sized so that the optical pressure sensors 10a, 10b, 10c and the optical fibers 11 do not protrude beyond the external diameter $D_{core}$ of the core wire 31 (see FIGS. 7B, 7C and 7D for example). Each sensor and optical fiber may be fixed to the core wire, e.g. adhesively fixed to the core wire, at one or more points. For example, during assembly, optical fibers 11 are adhesively attached to the core wire 31, e.g. with a suitable biocompatible and hemo-compatible adhesive 39, before the core wire is inserted into the coil wire 35. To accommodate the sensors 10a, 10b, 10c, which may be larger in diameter than the optical fibers 11 themselves, if required, the grooved structure may be enlarged in the region where the sensors 10a, 10b, 10c are located, i.e. at each sensor location. For example a cavity or recess 34 is ground in the core wire, as shown schematically in FIGS. 6, 7C and 7D, to provide space for the sensors 10a, 10b, 10c and a radiopaque marker 14. The guidewire coil 35 may be more loosely coiled, or otherwise structured, in the distal end portion 103 to provide apertures 36 between the coils of the wire of the guidewire coil near each of the optical pressure sensors that allow for fluid contact with the optical pressure sensors 10a, 10b, 10c.

Figure 7A:
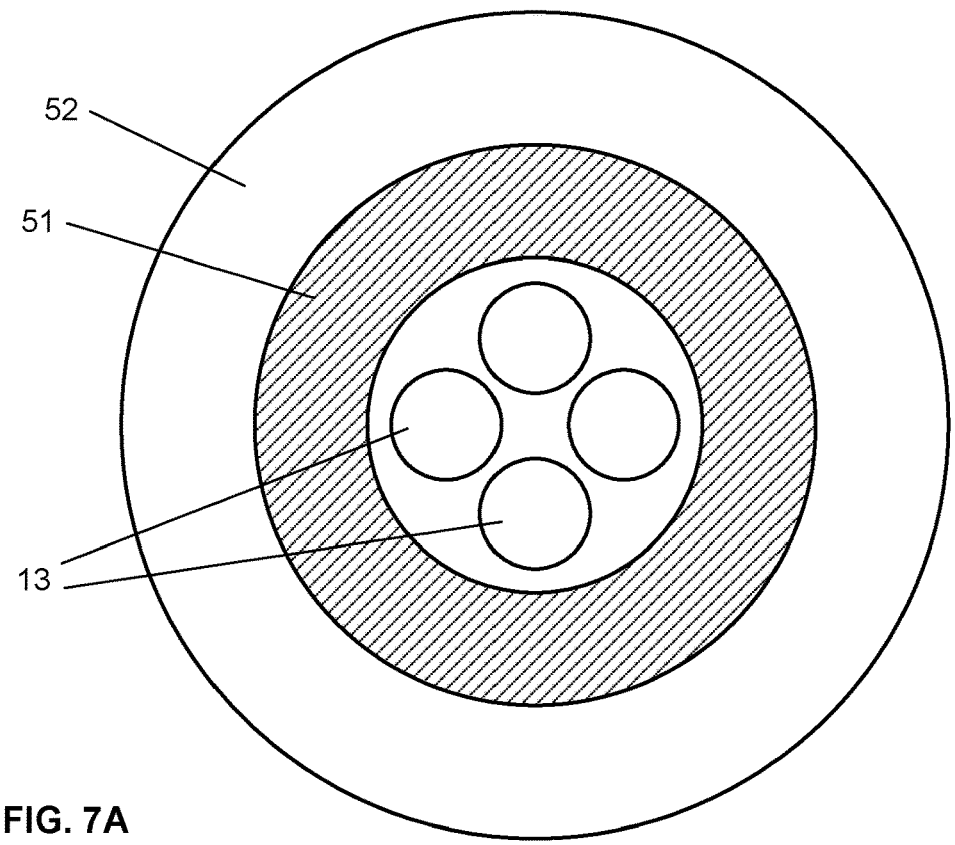
FIGS. 7A, 7B, 7C and 7D show enlarged axial cross-sectional views of the multisensor guidewire illustrated in 5A and 6 taken through planes A-A, B-B, C-C and D-D respectively for a core wire of another embodiment.
Figure 7B:
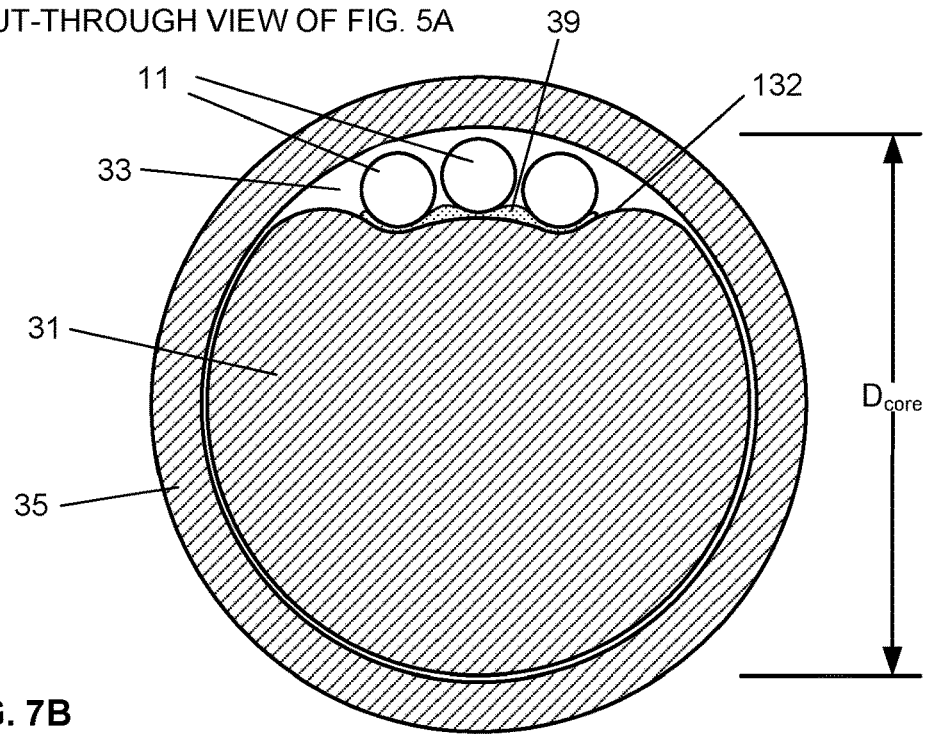
Figure 7C:
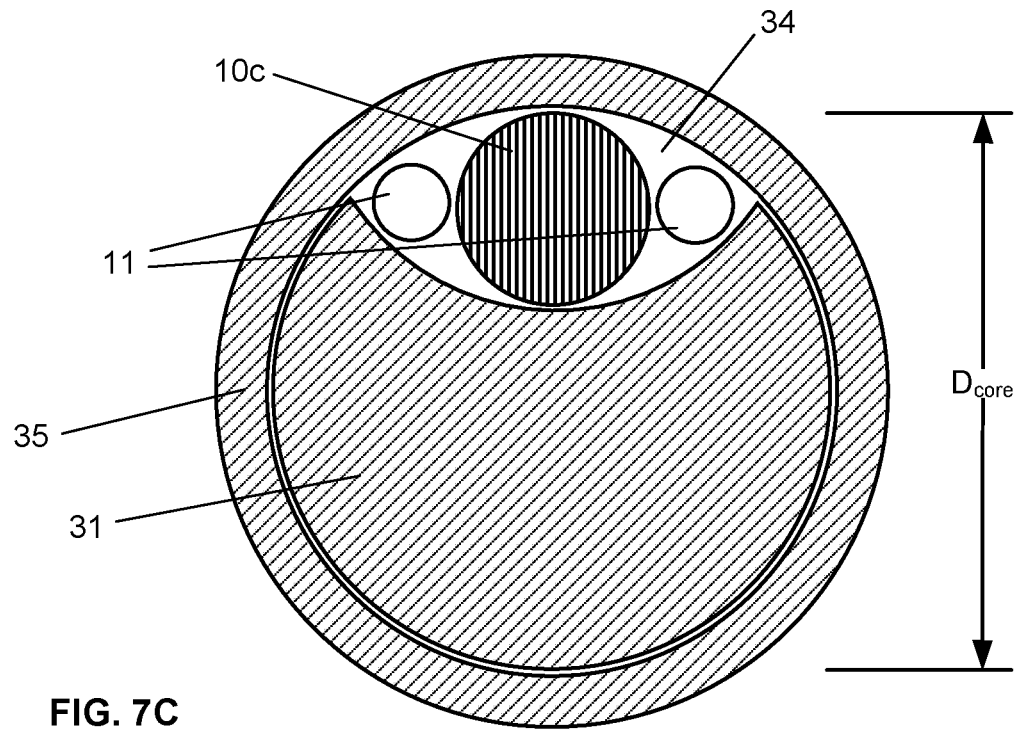
Figure 7D:
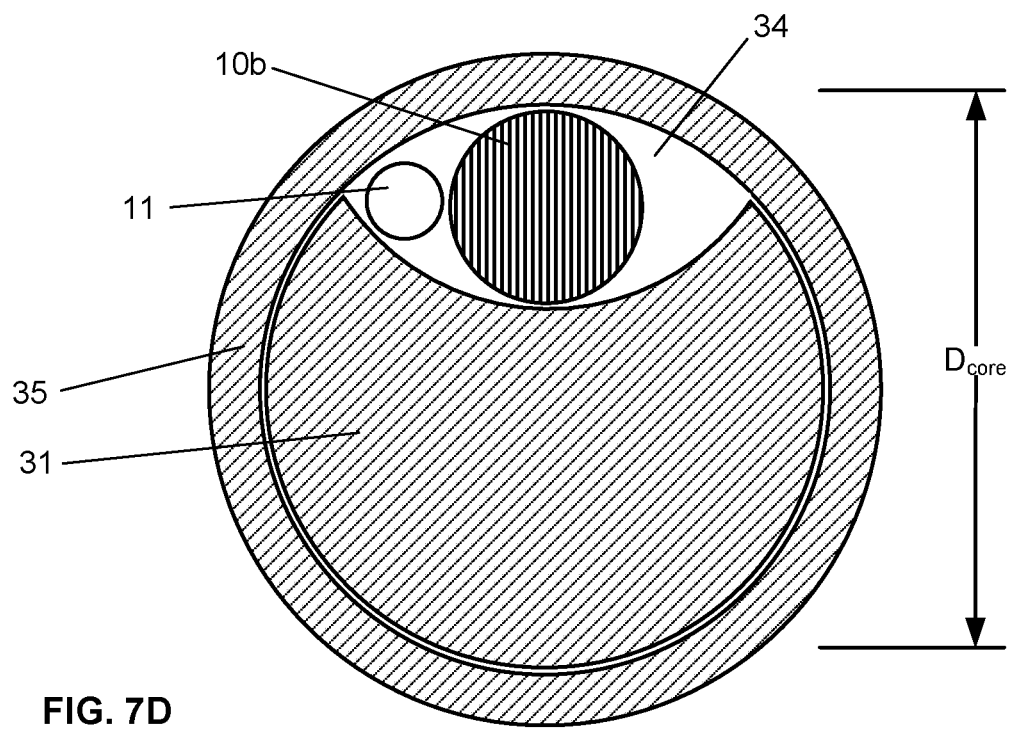

FIGS. 7A, 7B, 7C and 7D show enlarged axial cross-sectional views of the multisensor guidewire 200 taken through planes A-A, B-B, C-C and D-D respectively, of FIG. 5A. FIG. 7A shows the optical fibers 13 with tubing 51 and jacket 52 of the proximal part 101. FIGS. 7B, 7C and 7D show the core wire 31 within the outer coil 35 to illustrate the location of the optical fibers 11 in grooved structure 132, and the location of pressure sensors 10b, 10c within enlarged groove portion or cavity (recess) 34 in the core wire 31. As shown in FIGS. 7C and 7D, where the groove portion is enlarged to accommodate the sensors, the core wire has a lune-shaped cross-section.

Figure 8:
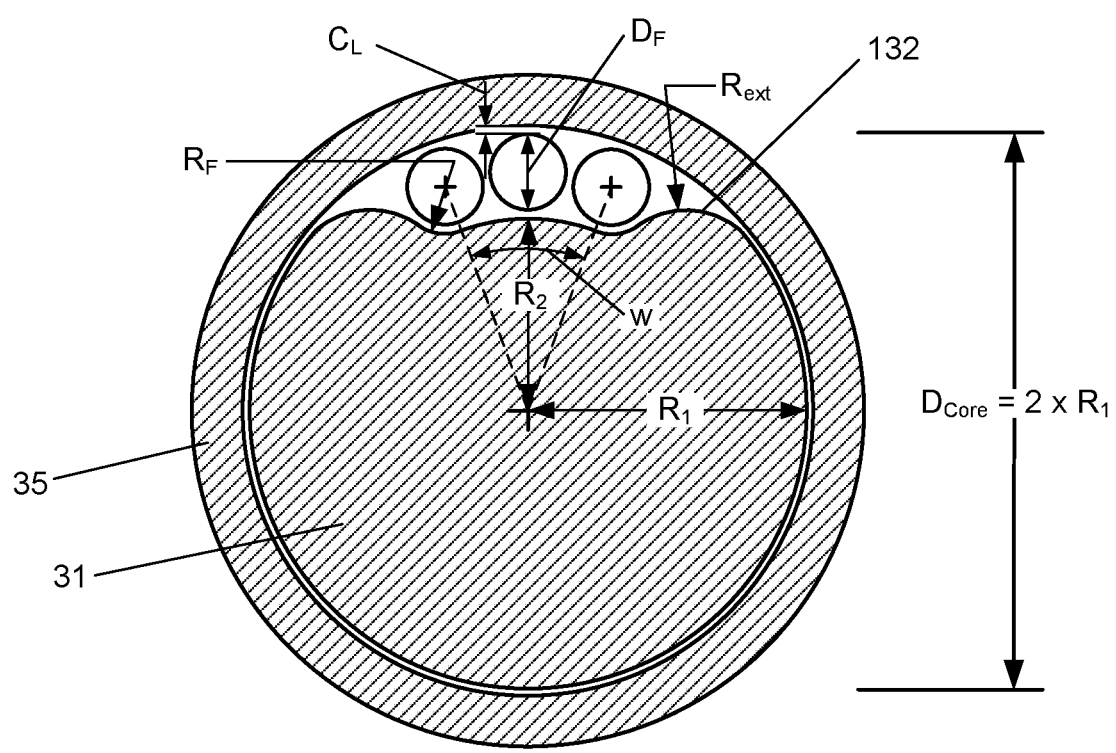
FIG. 8 shows the same cross-section as FIG. 7B with some relative dimensions marked.

Referring to FIG. 8, since the optical fibers do not contribute significantly to the stiffness of the guidewire, for superior stiffness required for a guidewire of a given outside diameter, e.g. ≤0.89 mm (0.035 inch), the diameter core wire is preferably as large as can be reasonably be accommodated within the outer coil of the guidewire (e.g. 0.029 inch) for a coil wire of 0.002 inch×0.012 inch. As illustrated schematically, if, for example, the optical fibers are of 0.100 mm (0.0039 inch) diameter, the grooved structure 132 in the core wire is sized accordingly to accommodate the three optical fibers 11 side by side, in the space or channel left between the core wire 31 and outer coil 35. For example, for a 0.029 inch diameter core wire $R_1$=0.0145 inch, the inner radius $R_2$ of the grooved part of the guidewire be 0.009 inch, so as to accommodate optical fibers 11 of 0.100 mm (0.0039 inch) diameter, and adhesive 39 for bonding the fibers to the core wire, without protruding beyond the diameter $D_{core}$ of the core wire, as illustrated in FIG. 7C. The width w of the groove structure allows for the three fibers to lie side by side. The depth and contouring of the grooved structure is sufficient to accommodate the diameter of the fibers $D_F$ within the diameter $D_{core}$ of the core wire. A core wire of this embodiment is more readily manufactured using known wire rolling or wire drawing processes. A single grooved structure for multiple optical fibers and sensors also facilitates assembly of the optical sensors, optical fibers and the core wire, e.g. by adhesive bonding to the core wire. The assembly of the core wire and optical sensors and their respective optical fibers may then be inserted into the outer flexible coil of the guidewire.

Figure 9A:
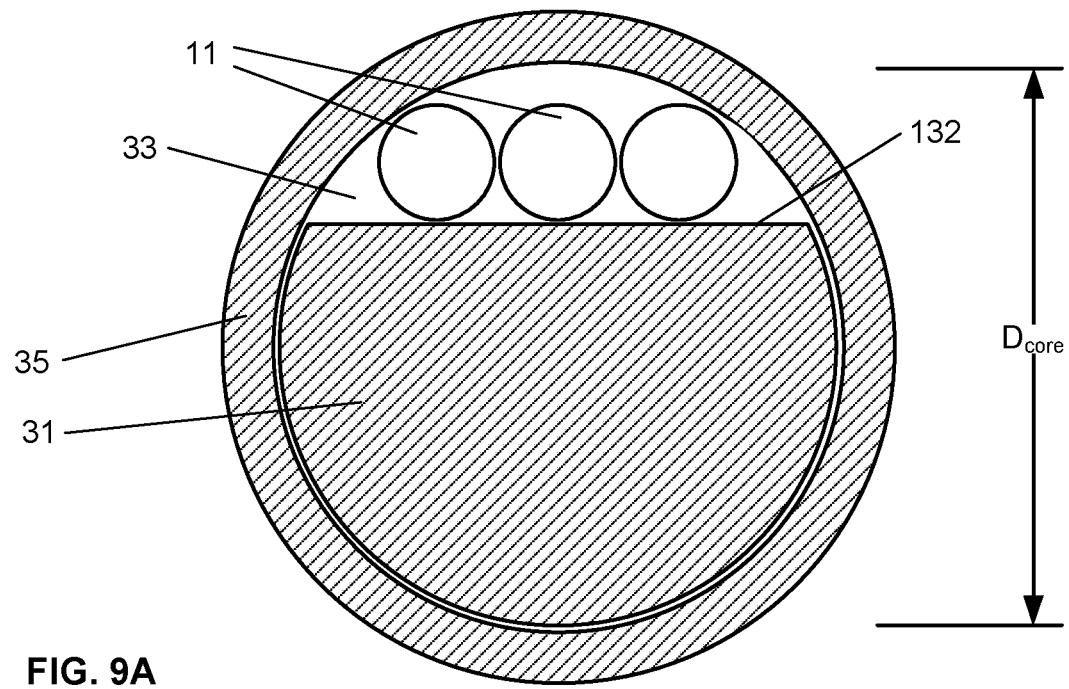
FIGS. 9A, 9B, 9C and 9D show enlarged axial cross-sectional views of the multisensor guidewire illustrated in FIG. 5B for a core wire of the third embodiment, the view being taken through planes A-A, B-B, C-C and D-D respectively.
Figure 9B:
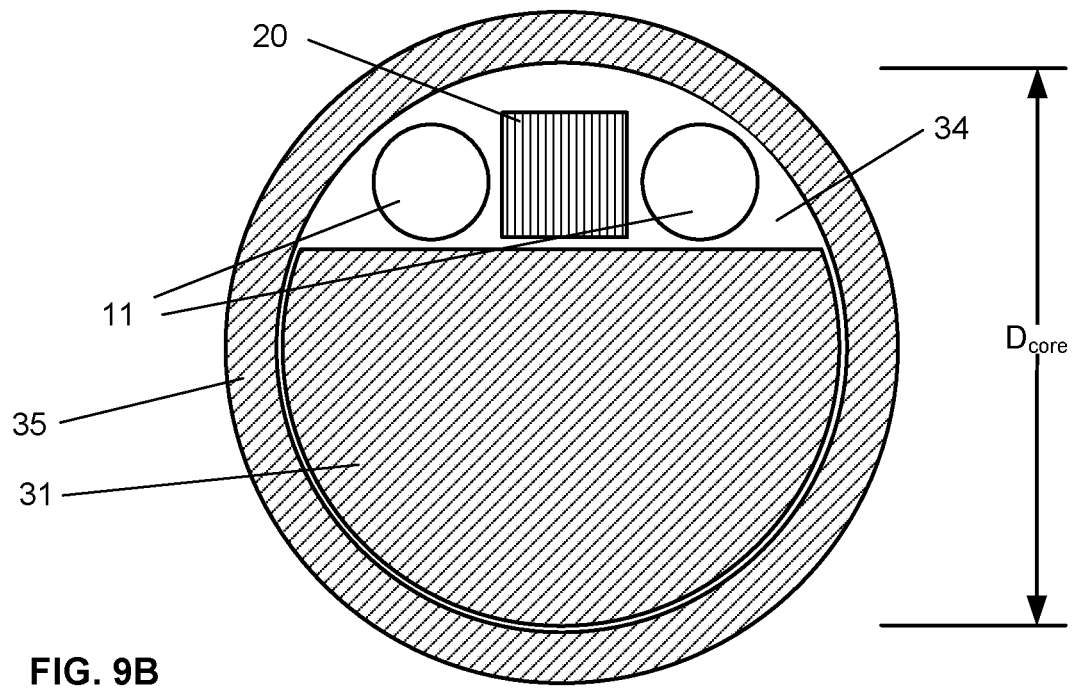
Figure 9C:
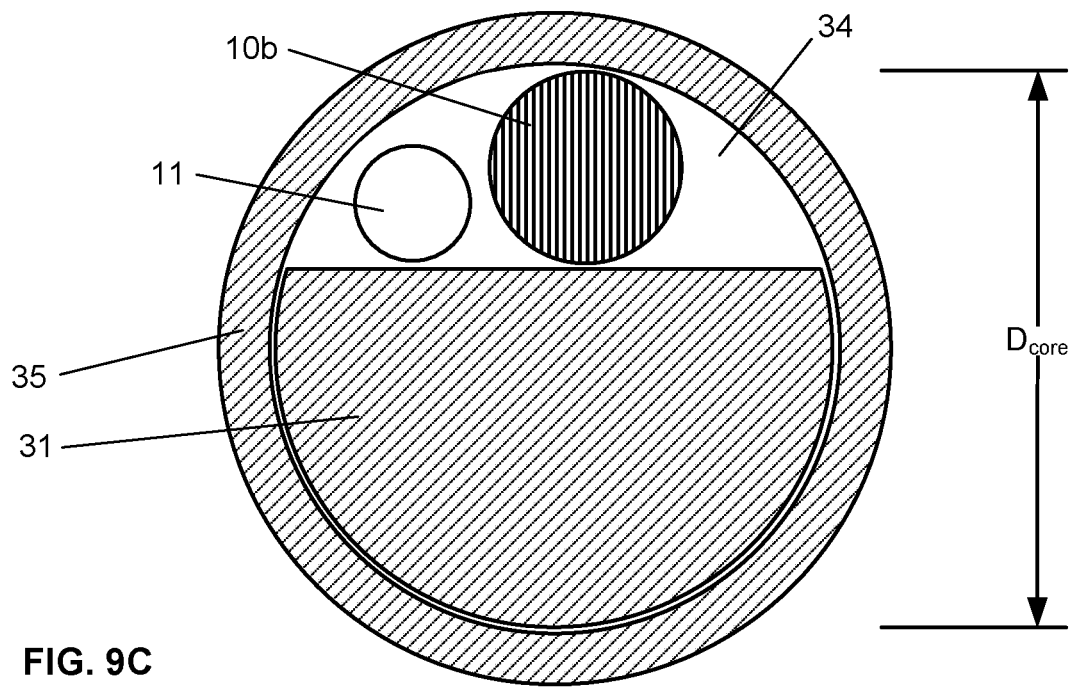
Figure 9D:
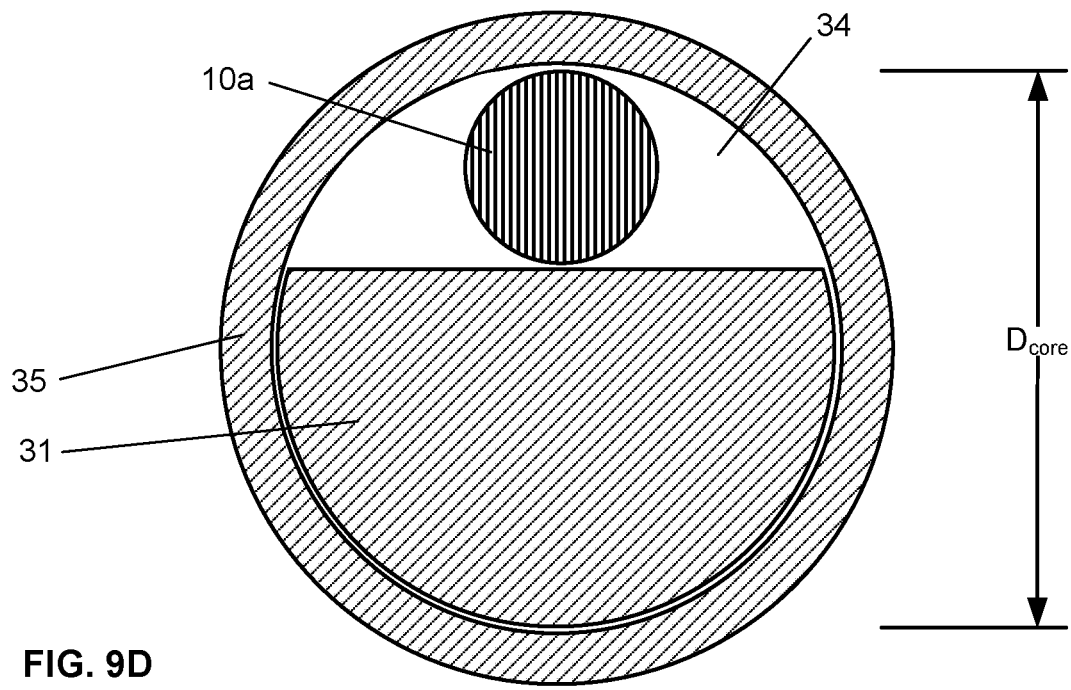
Figure 10A:
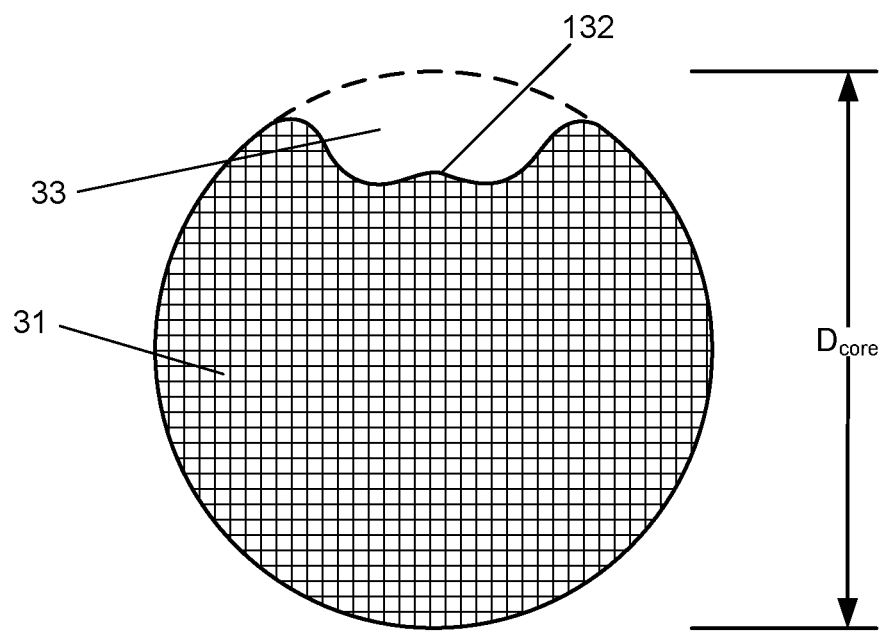
FIGS. 10A, 10B, 10C and 10D show enlarged axial cross-sectional views of core wires of other alternative embodiments, having different cross-sectional profiles.
Figure 10B:
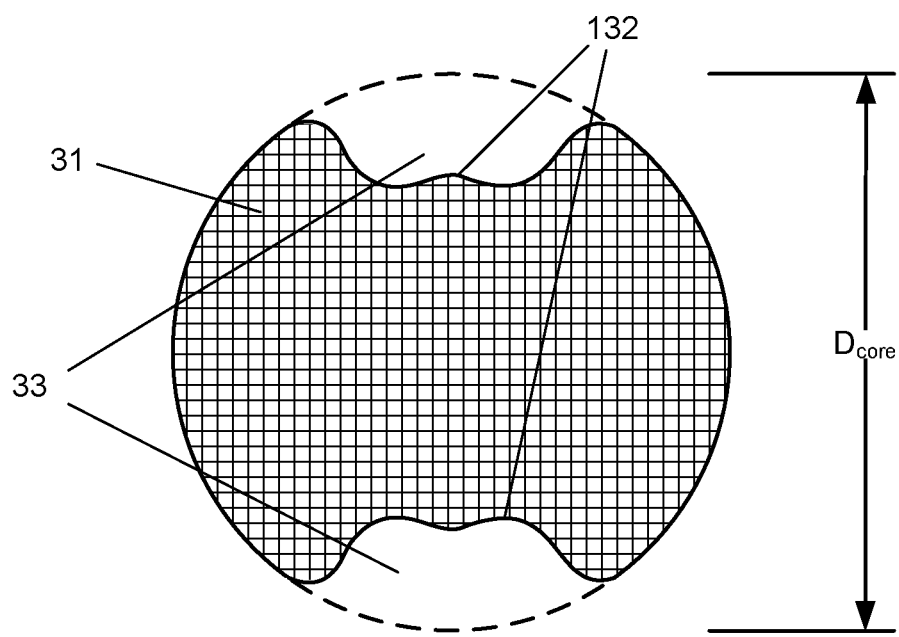
Figure 10C:
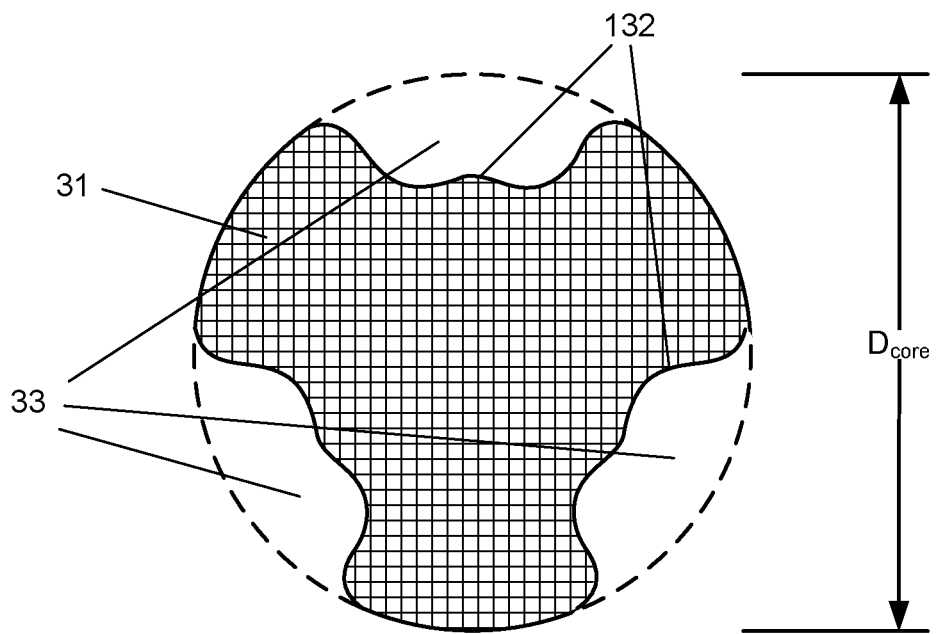
Figure 10D:
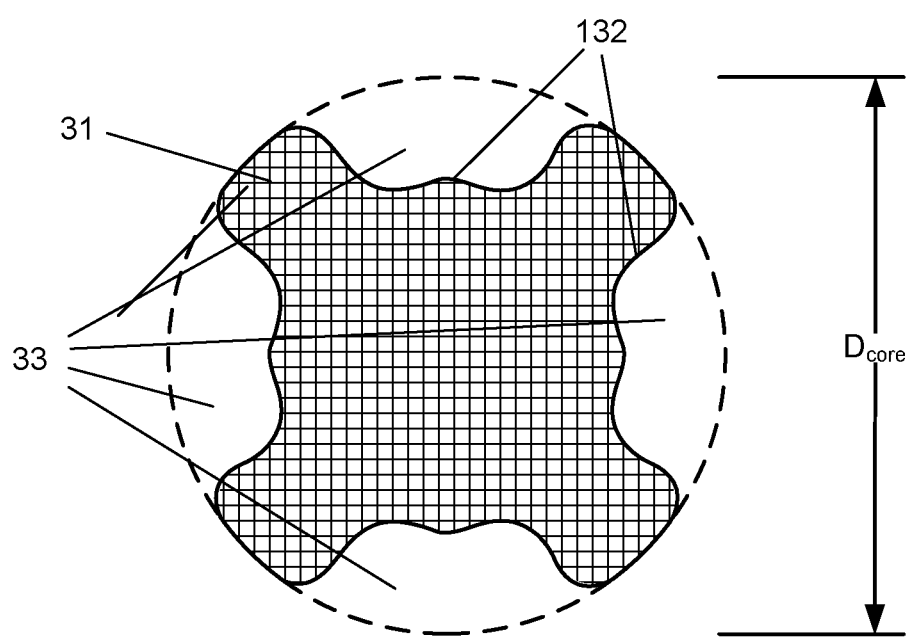

FIGS. 9A, 9B, 9C and 9D show enlarged axial cross-sectional views of the multisensor guidewire illustrated in FIG. 5A, comprising a core wire 31 of a third embodiment, taken through planes A-A, B-B, C-C and D-D respectively. The multisensor guidewire in this embodiment comprises 3 optical fibers 11, two optical pressure sensors 10a, 10b and one optical flow sensor 20. Compared with the core wire shown in FIGS. 7A, 7B, 7C and 7D, the core wire 31 shown in FIGS. 9A, 9B, 9C and 9D has a simpler cross-sectional profile comprising a channel surface 132, i.e. a groove or facet, along one side of the core wire 31 to provide a channel 33 between the core wire 31 and the outer coil 35. For example, the channel surface 132 is formed by grinding a round wire, or by wire drawing, could be described as having a generally D-shaped cross-sectional profile. That is, as shown in FIG. 9A, the core wire is generally circular, having an outer diameter that fits within the outer flexible coil. Geometrically, the cross-sectional profile of the core wire thus has the form of the major segment of a circle, wherein the channel surface 132 is defined by a chord of the circle. The resulting space or channel 33 for the fibers and enlarged portion 34 for the sensors, that is, formed between the core wire and the inner diameter of the outer flexible coil, has a cross-sectional profile defined by the minor segment of the circle.

The groove structure 32 may be substantially flat as illustrated, or may be contoured, e.g. with a convex profile or concave profile (see e.g. FIGS. 7C and 7D). In this embodiment, the groove 32 in the core wire 31 is sized to accommodate the three optical fibers 11 for the optical sensors 10a, 10b and 20, within space 33. If required, optical sensors 10a, 10b and 20 are located within enlarged groove portions at sensor locations, e.g. a cavity or recess 34 in the core wire 31, such as illustrated in FIGS. 7C and 7D.

FIGS. 10A, 10B, 10C and 10D show core wires 31 of other alternative embodiments, having other cross-sectional profiles where channel surfaces 132 defining the grooves are contoured, e.g. by wire rolling or wire drawing processes, to form channels 33 within the diameter $D_{core}$ of the core wire. Each channel 33 may accommodate one or more optical fibers and respective optical sensors. As illustrated, and as mentioned above, in this context, for a wire with a cross-section that is not entirely circular, the diameter $D_{core}$ of the core wire refers to the diameter of the circle into which the wire will fit.

As described above, core wires according to some embodiments of the invention comprise a channel surface in the form of multiple grooves, each groove accommodating a single fiber and optical sensor. In other embodiments, one or more channel surfaces defining one or more larger grooves are provided, each groove accommodating two or more fibers and optical sensors. Preferably, the optical fibers and their respective optical sensors are accommodated within the groove and within the diameter $D_{core}$ of the core wire (see FIGS. 4B, 8 and 9A for example). To facilitate fabrication, this enables the optical fibers carrying the optical sensors to be fixed to the core wire, e.g. by adhesively bonding the fibers to the channel surface(s) of the core wire, to form an assembly of the core wire and the plurality of optical fibers and optical sensors, with the optical sensors appropriately spaced apart and positioned at the required sensor locations. Then, the assembly of the core wire, fibers and optical sensors can be inserted into the outer flexible coil.

Optical Micro-Coupler

Figure 19:
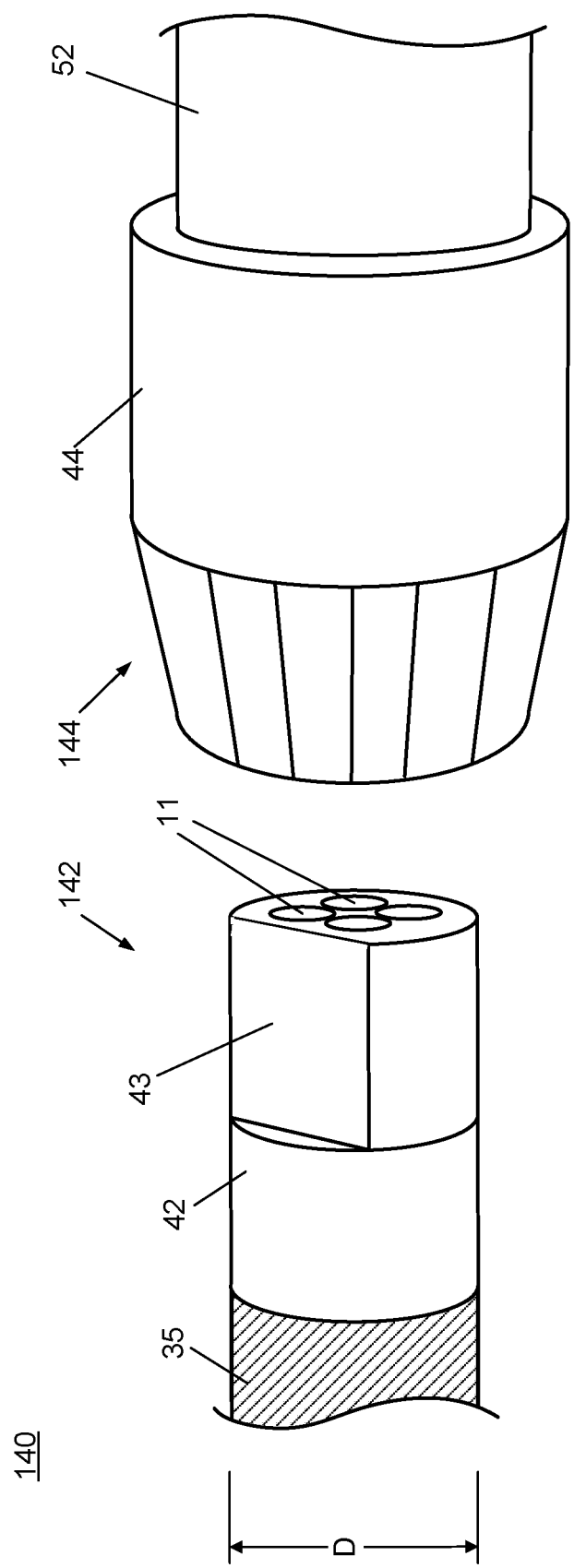
FIG. 19 illustrates schematically a view of the male and female connectors of the micro-optical coupler for optically coupling the distal and proximal parts of the multisensor guidewire.

As illustrated in FIG. 19, the micro-coupler 140 comprises male and female parts, 142 and 144 respectively, to provide for optical coupling of each optical pressure sensor 10a, 10b, 10c and optical flow sensor 20 via their respective individual optical fibers 11 of the distal part 102 to respective individual fibers 13 of the proximal part 101. Notably, the male portion 142 of the micro-optical coupler has the same outside diameter D as the coil 35 of the guidewire to enable components for TVT to be mounted on or over the guidewire. The female portion 144 of the micro-optical coupler is of larger diameter and may be formed to act as a hub 44 that can be grasped facilitate handling and torque steering of the guidewire, and as well as to facilitate engaging and disengaging distal part 102. An alignment means, such as facet 43 of the male part 142, which aligns to a corresponding facet (not visible) in the female part 144 ensures that individual fibers 11 are indexed, aligned and correctly optically coupled to respective corresponding individual fibers 13 for optical data communication. The connector 140 may also include a suitable fastening means for securely attaching and locking/unlocking the two parts 142 and 144 of optical coupler 140.

For example, the sensor guidewire may be unlocked from the proximal part, to remove the attachment of the guidewire to the control console (control unit 151). Then a catheter, or other component, can be inserted over the multisensor guidewire 102. Then the sensor guidewire is recoupled to the control console to perform pressure and flow measurements. This provides ease of use for insertion of catheters, balloons, valve delivery catheters, or other required components.

Figure 20:
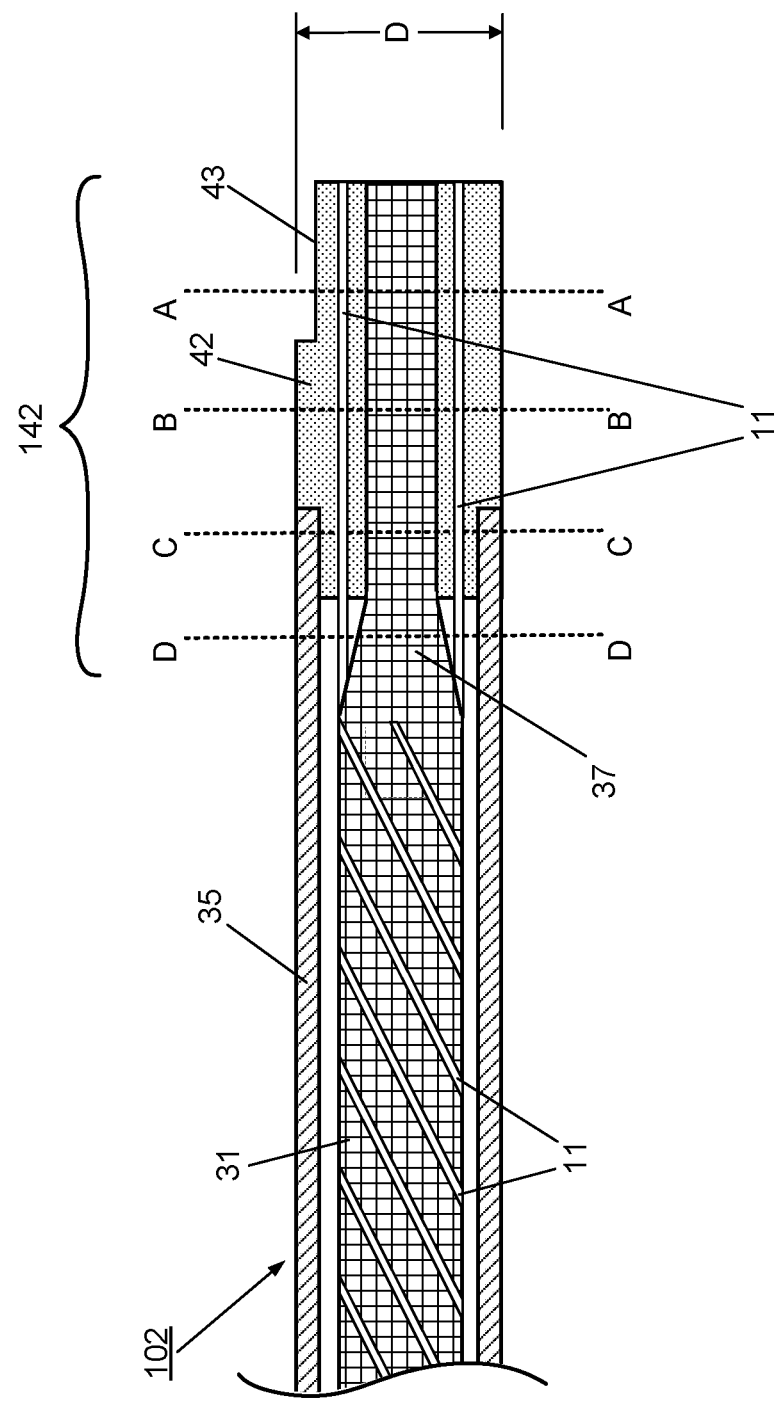
FIG. 20 illustrates schematically an enlarged longitudinal cross-sectional view of the male part of the multisensor guidewire optical connector illustrated in FIG. 19.
Figure 21A:
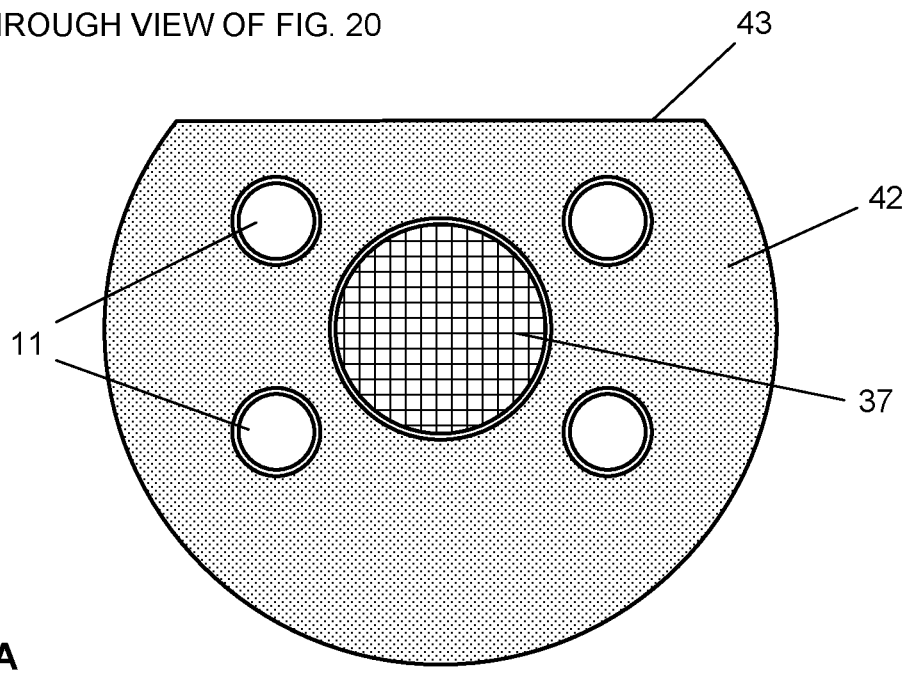
FIGS. 21A, 21B, 21C and 21D show enlarged axial cross-sectional views of the multisensor guidewire optical connector illustrated in FIG. 20 taken, respectively, through planes A-A, B-B, C-C and D-D indicated in FIG. 20.
Figure 21B:
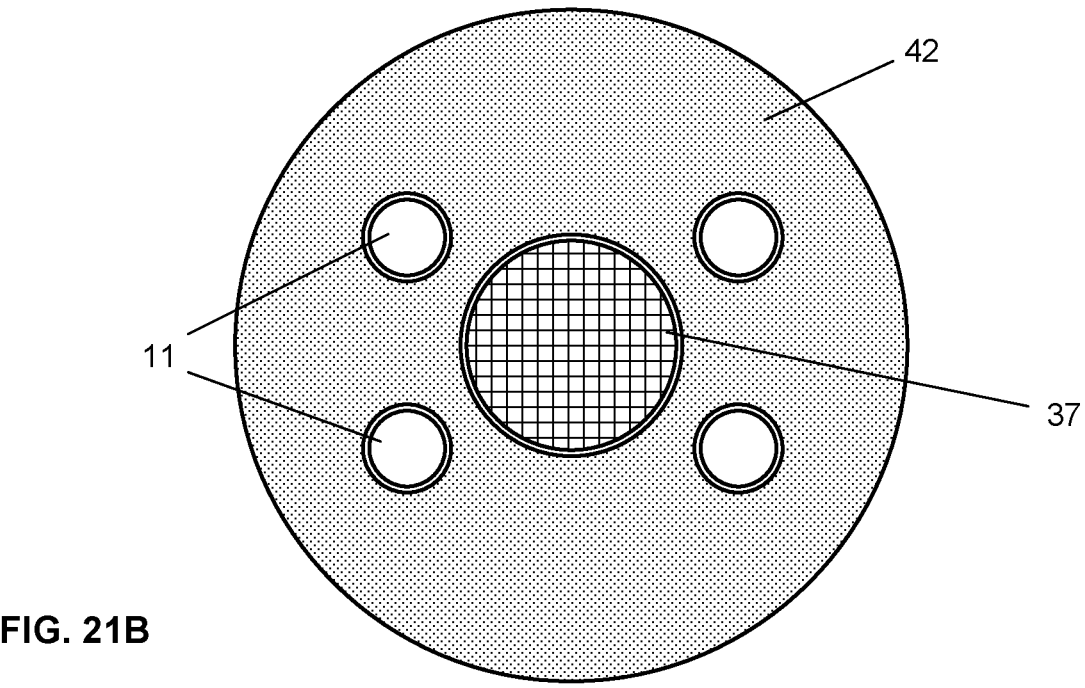
Figure 21C:
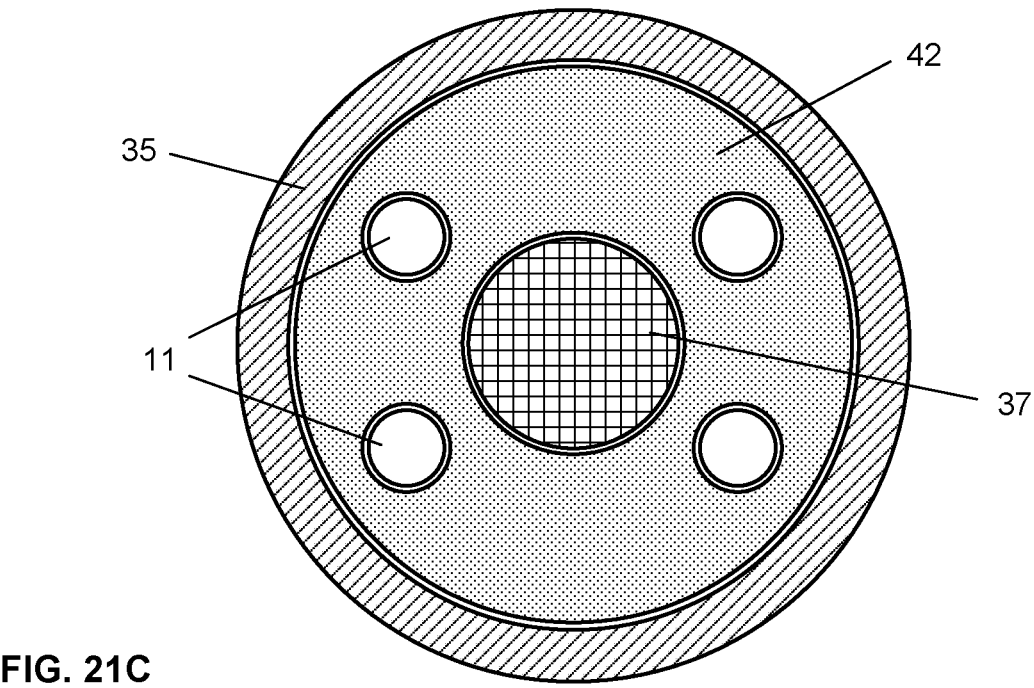
Figure 21D:
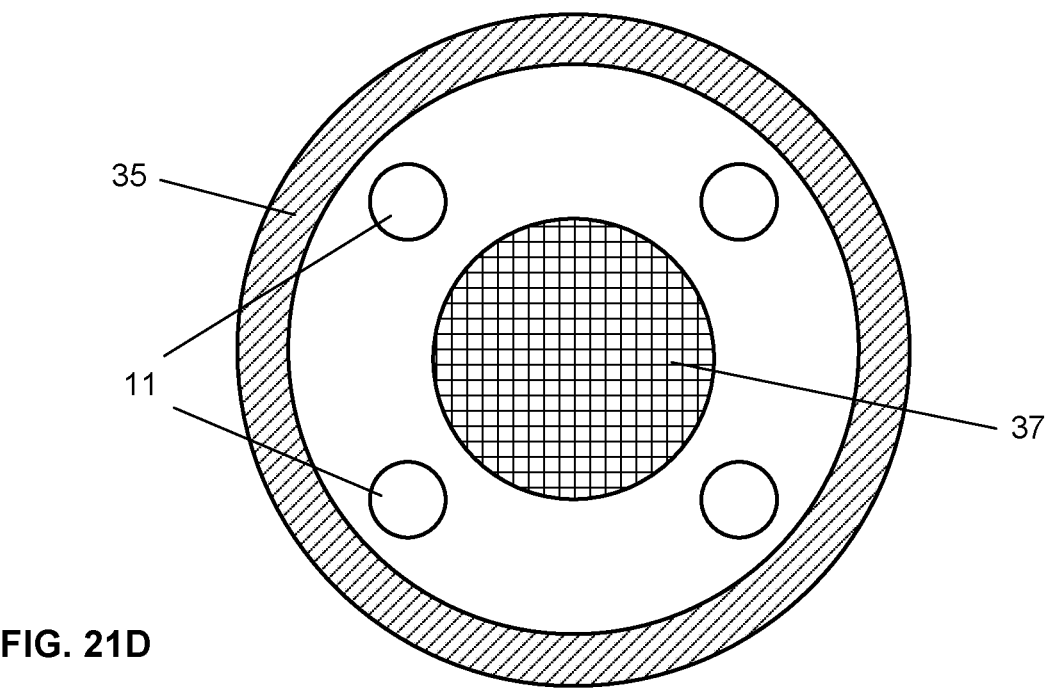

FIG. 20 shows a cross-sectional view of the proximal end of distal part/guidewire 102 showing the internal structure of the male part 142 of connector 140. As illustrated schematically, the core wire 31 is tapered to form a core 37 at its end that inserts into the ferrule 42 of connector part 142 so that the individual optical fibers 11 are guided from the grooves 32 in the core wire 31 into and through the ferrule 42 of the connector part 142. The internal structure of the male connector part 142 is shown through cross-section through A-A, B-B, C-C and D-D in subsequent FIGS. 21A, 21B, 21C and 21D

Notably, the micro-coupler 140 provides for disengagement of the distal part 102 from the proximal part 101 of the guidewire. Moreover, the male part 142 has the same outside diameter D as the coil 35 of the multisensor guidewire. Thus, the distal part 102 functions as a conventional support guidewire, in that, components such as a replacement valve and delivery system, or other components, can be mounted on/over the guidewire for guiding and delivery into the heart.

The female part 144 of the micro-connector 140 may have an outer hub 44 of larger diameter to facilitate handling, alignment and connection of the micro-coupler 140.

Although a single optical connector 112 is shown for the input/output for each of the optical fibers 13, in other embodiments, an alternative connector or coupling arrangement may be provided. The multisensor wire connector 112 and the control unit port 153 may comprise several individual optic fiber connectors, instead of a single multi-fiber connector. The connector 112 may optionally include circuitry allowing wireless communication of control and data signals between the multisensor wire 100 and the control unit 151. Optionally one or more electric connectors for peripheral devices, or for additional or alternative electrical sensors, may be provided.

Figure 11A:
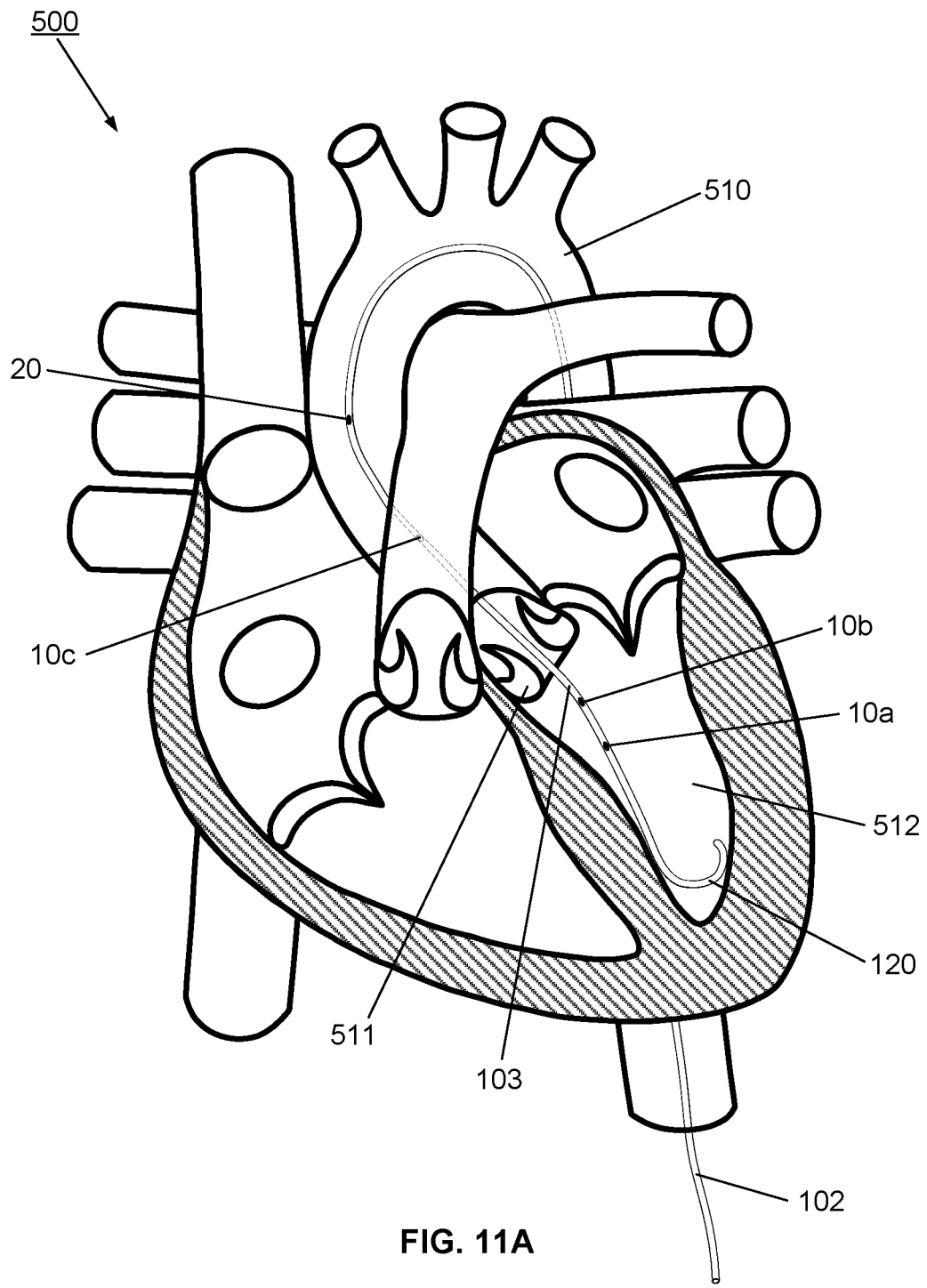
FIG. 11A shows a schematic diagram of a human heart to illustrate placement within the left ventricle of a multisensor guidewire, similar to that shown in FIG. 2, for use as: a) a guidewire during a TAVI procedure; and b) for directly measuring a blood pressure gradient across the aortic heart valve before and after the TAVI procedure.

Referring to FIG. 11A, this shows schematically the placement of the distal end portion 103 of the guidewire 102 within the left ventricle 512 in the human heart 500. For TVT procedures, the distal tip 120 is preferably of a suitable structure, such as a flexible and specially curved tip or J-tip, to assist in firmly anchoring the distal end of the guidewire in position in the ventricle, without causing trauma to the ventricular wall, the valve, or other tissues within the heart. Anchoring of the guidewire, in a stable but atraumatic manner, is particularly important during TVT procedures, i.e. to ensure accurate and optimum placement of replacement valve and to hold the valve in position during valve implantation and/or during other therapeutic or diagnostic procedures before or after implantation. This also facilitates precise positioning of the sensors in the region of interest for more accurate and reliable measurements of parameters such as blood pressure, transvalvular pressure gradient, and blood flow, both before, during or and after the TVT procedures.

Figure 11B:
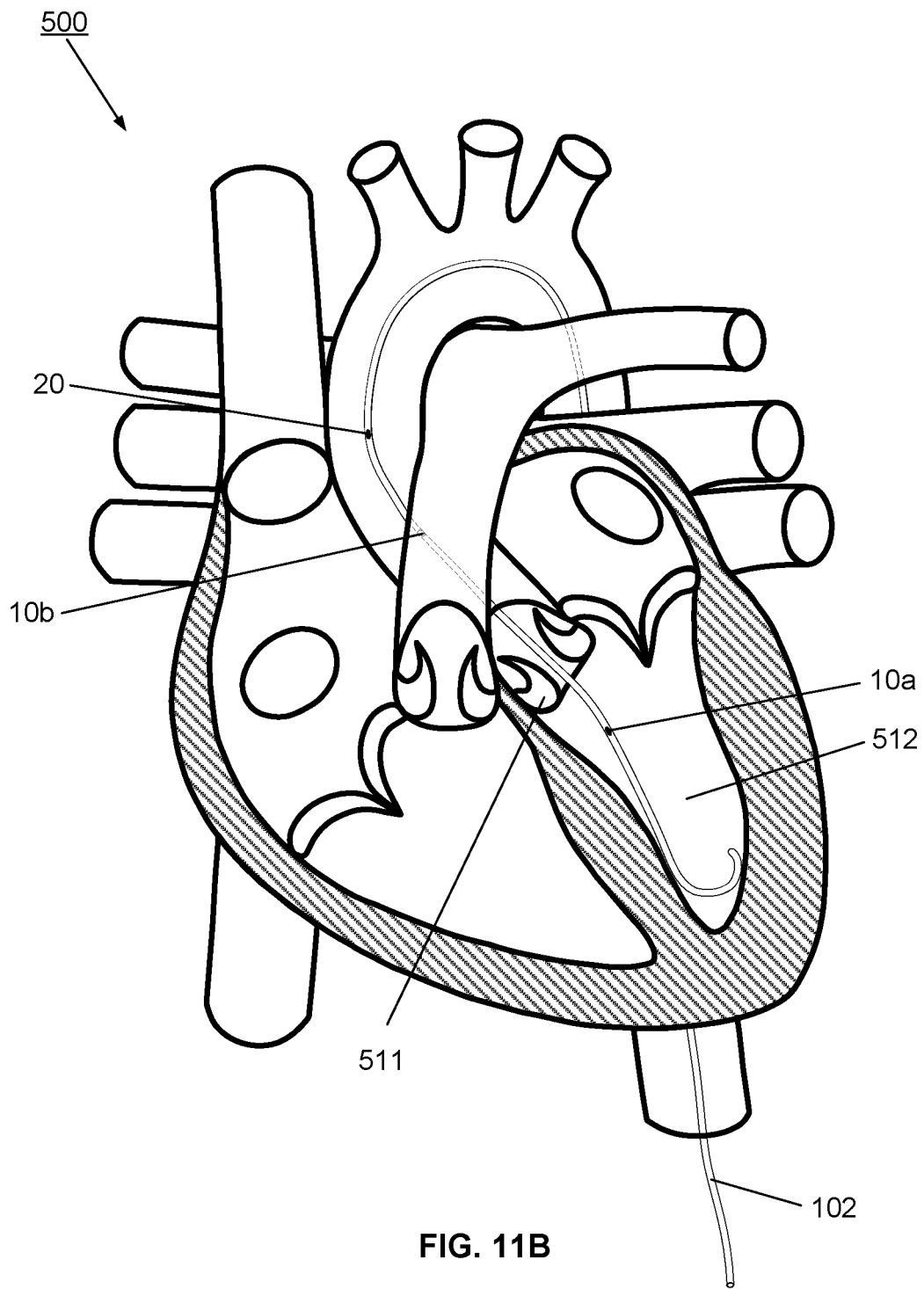
FIG. 11B shows a schematic diagram of a human heart to illustrate placement within the left ventricle of a multisensor guidewire, similar to that shown in FIG. 5, for use as: a) a guidewire during a TAVI procedure; and b) for directly measuring a blood pressure gradient across the aortic heart valve before and after the TAVI procedure, wherein a flow sensor is provided for measuring blood flow upstream of the aortic valve.

FIG. 11B shows a schematic diagram of a human heart 500 to illustrate placement within the left ventricle 512 of a multisensor guidewire 102, similar to that shown in FIG. 5, for use as both: a) a guidewire during a TAVI procedure and b) for directly measuring a blood pressure gradient across the aortic heart valve 511 before and after the TAVI procedure, wherein a flow sensor 20 is provided for measuring blood flow upstream of the aortic valve 511. The multisensor guidewire 102 comprises two optical pressure sensors 10a, 10b, which are spaced apart by a suitable distance, e.g. at least 20 mm to 50 mm apart and more preferably about 80 mm apart, so that one sensor can be located upstream and one sensor located downstream of the aortic valve 511. The flow sensor 20 is located further downstream of the aortic valve 511, in the root of the aorta, e.g. a distance $L_{FS}$ of about 20 mm from the nearest pressure sensor 10b.

For example, a sensor spacing of about 20 mm to 50 mm would be sufficient to place one sensor upstream and one downstream of a heart valve. However, blood pressure measurements may be affected by significant turbulence in the blood flow through the cardiac cycle. For this reason, a spacing of 80 mm between the two sensor locations may be preferred to enable one sensor to be located further into the ventricle and another sensor to be located further upstream of the valve in the aorta, so that both sensors are located in regions of less turbulent flow, i.e. spaced some distance each side of the valve. Based on review of CT scans to assess dimensions of the heart of a number of subjects, an 80 mm spacing of two pressure sensors may be preferred. For paediatric use, a closer spacing of the sensors may be preferred.

Figure 12A:
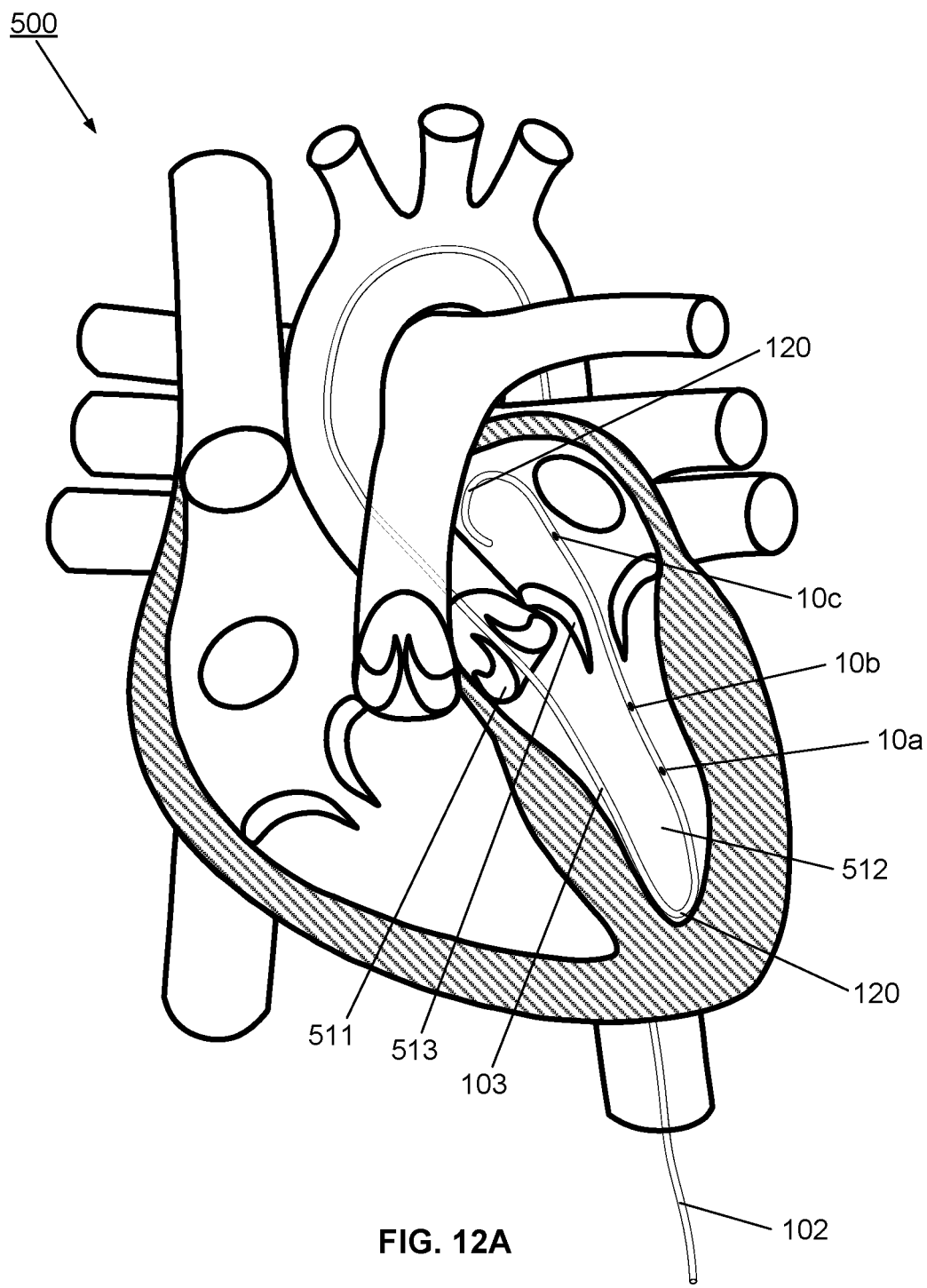
FIGS. 12A, 12B and 12C show corresponding schematics of a human heart illustrating three potential approached for placement of the multisensor guidewire of FIG. 5 through the mitral valve, for use as: a) a support guidewire during a TVT procedure; and b) as a diagnostic tool for directly measuring a blood pressure gradient across the heart valve before and after the TVT procedure.
Figure 12B:
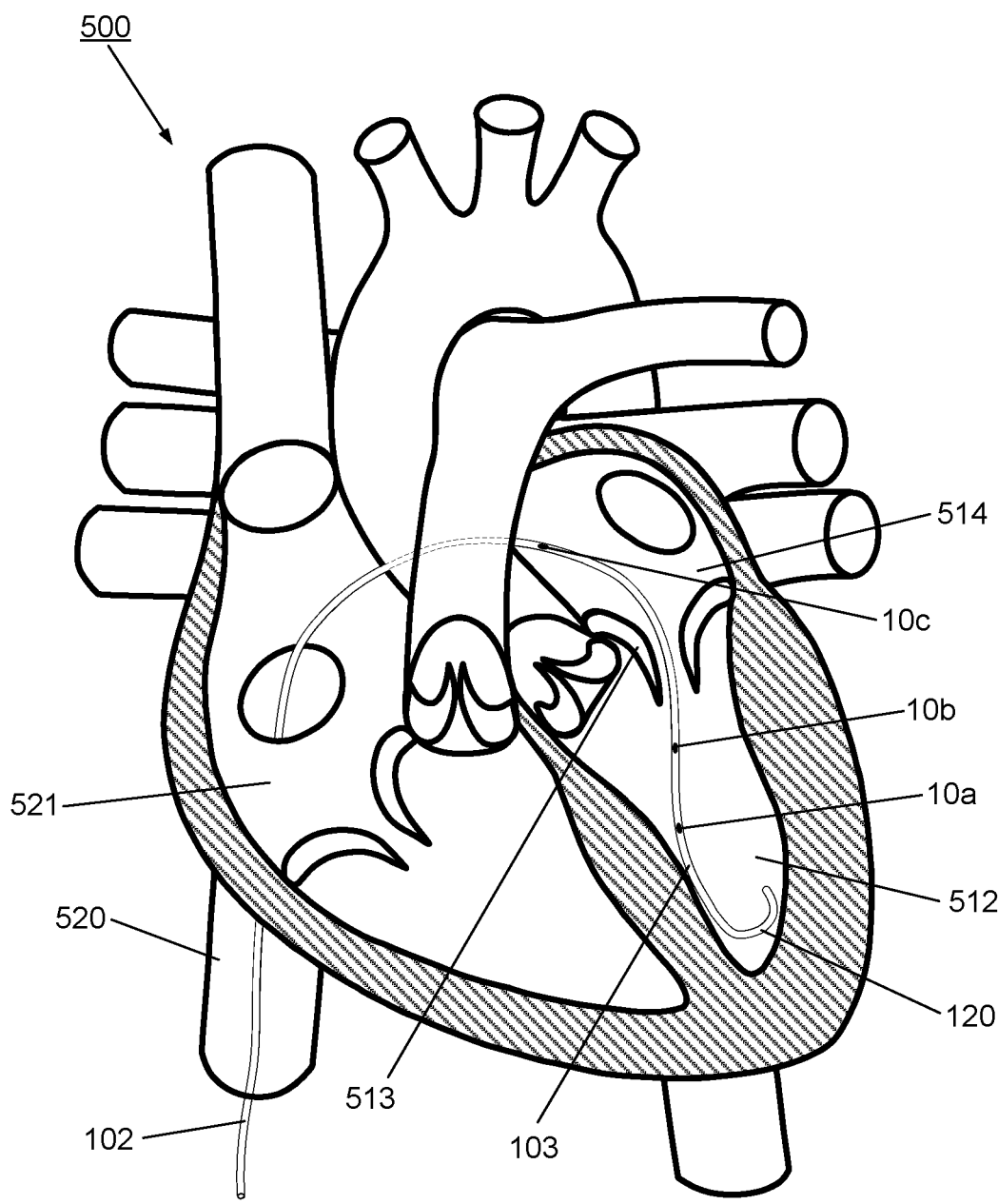
Figure 12C:
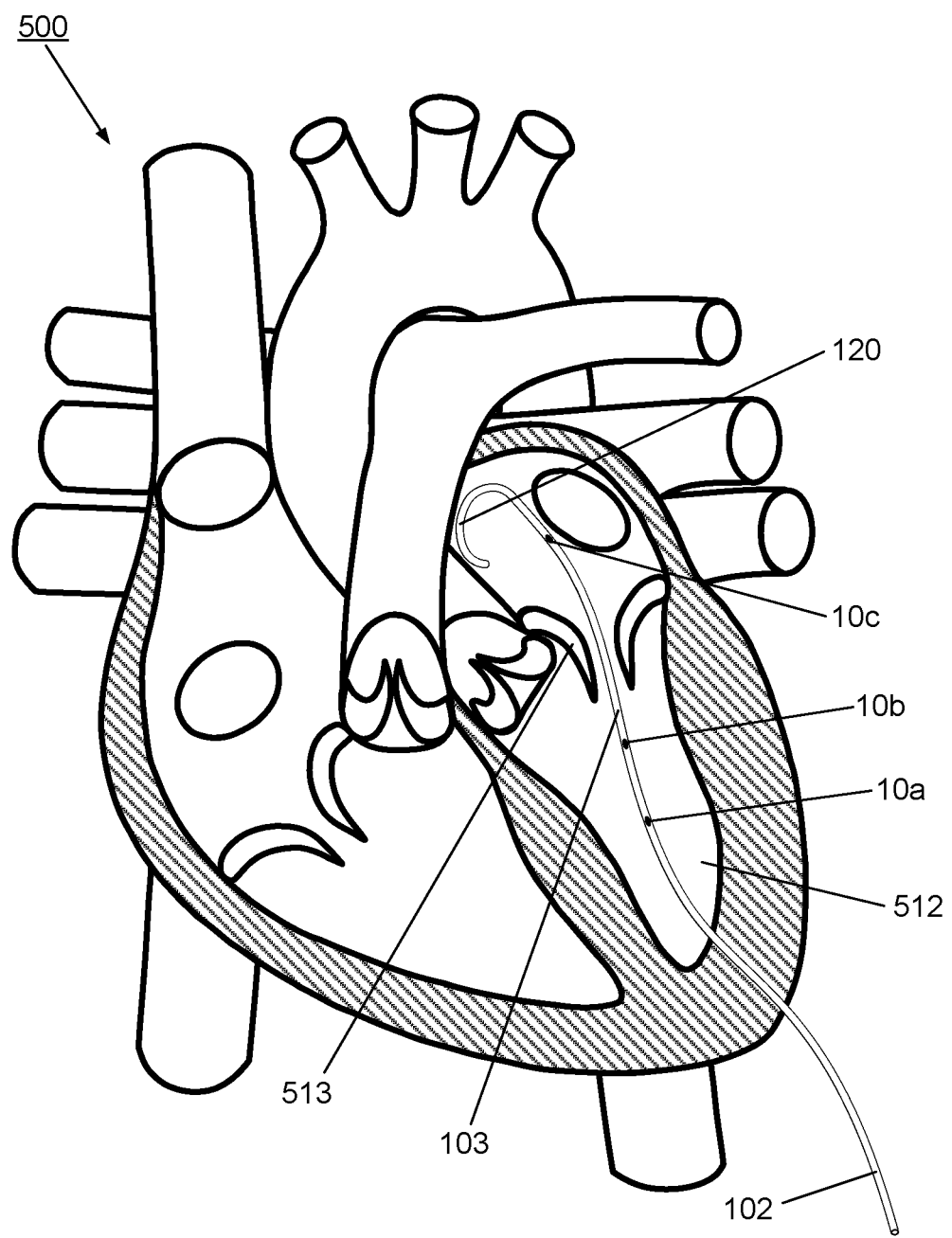
Figure 13:
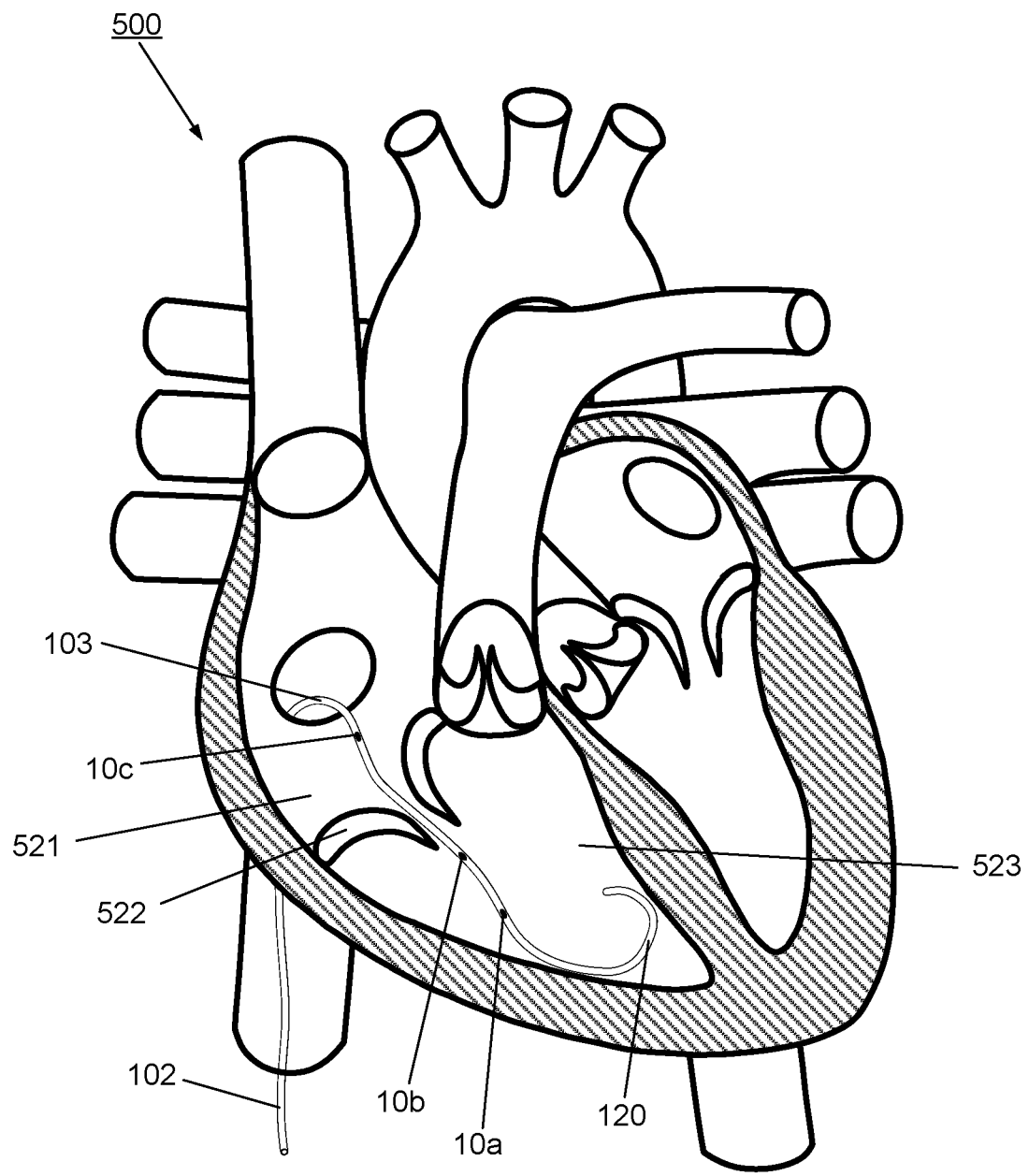
FIG. 13 shows a corresponding schematic of a human heart illustrating placement of the multisensor guidewire through the tricuspid valve, for use as: a) a guidewire during a TVT procedure; and b) for directly measuring a blood pressure gradient across the heart valve before and after the TVT procedure.
Figure 14:
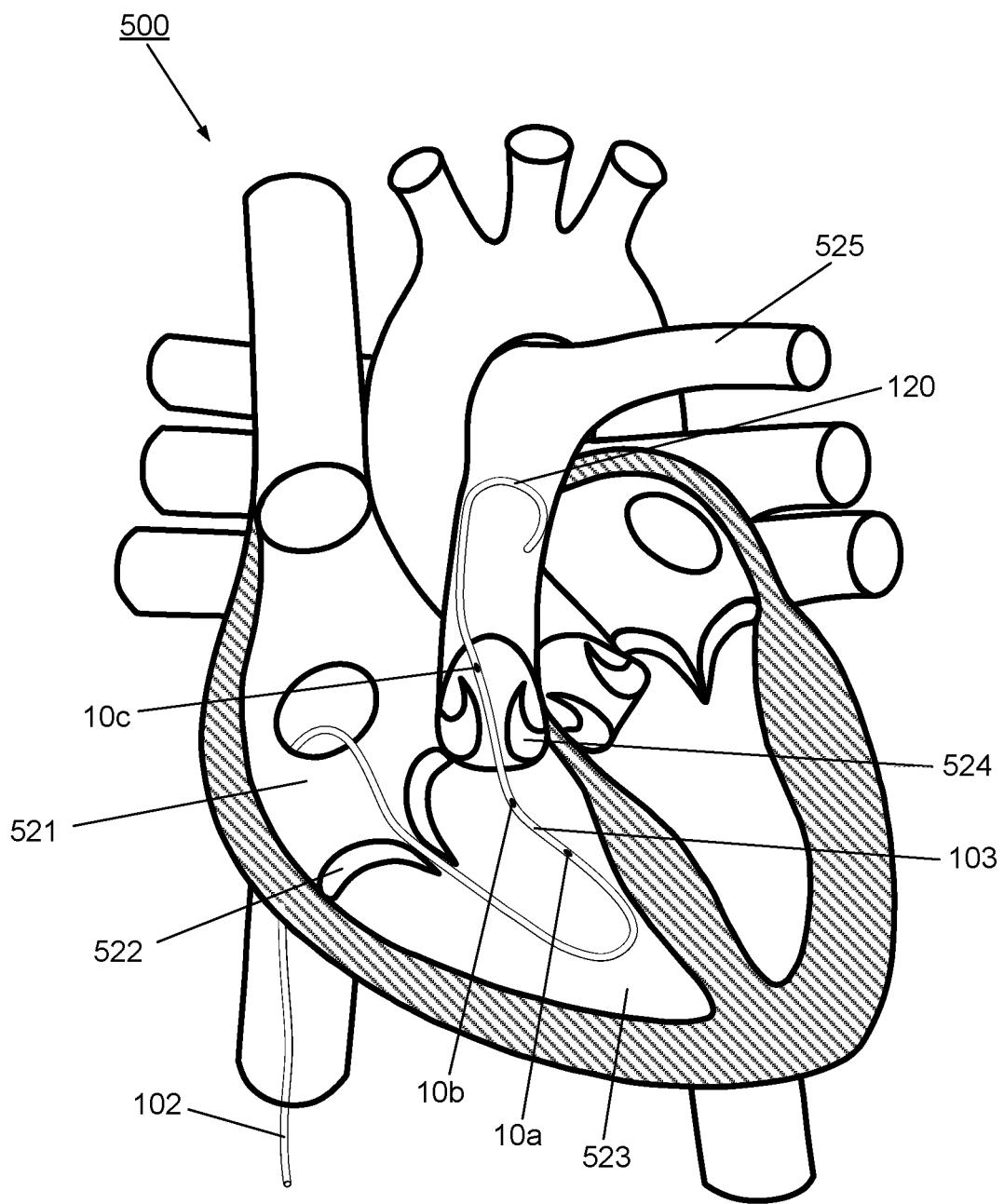
FIG. 14 shows a corresponding schematic of a human heart illustrating placement of the multisensor guidewire through the pulmonary valve, for use as: a) a guidewire during a TVT procedure; and b) for directly measuring a blood pressure gradient across the heart valve before and after the TVT procedure.

For comparison, FIGS. 12A, 12B and 12C show, schematically, three approaches for positioning of the distal end portion 103 of the guidewire 102 through the mitral valve 513. Correspondingly, FIGS. 13 and 14 show placement through the tricuspid valve 522 and through the pulmonary valve 224, respectively. Each of these Figures indicates how the three optical pressure sensors 10a, 10b, 10c would be placed for measurement of a transvalvular pressure gradient.

In practice, it is desirable that a multisensor guidewire provides a plurality of optical pressure sensors, e.g. two or three pressure sensors, and optionally a flow sensor, that are optimally spaced for measurement of transvalvular pressure gradients and flow for any one of the four heart valves. For example, while multisensor guidewires may be individually customized for different TVT procedures, or, for example, smaller sized versions may be provided for paediatric use, it is preferred to have a standard arrangement, e.g., two, three or four sensors, which is suitable for various diagnostic measurements and for use during various TVT procedures.

Transvalvular Pressure Measurements in Interventional Cardiology

By way of example only, the use of a multisensor guidewire for transvalvular pressure measurement will be described with reference to the multisensor guidewire 100 of the first embodiment, and with reference to the aortic valve. For measuring and monitoring the blood pressure gradient across the aortic valve 511, i.e. the aortic transvalvular pressure gradient in a human heart 500 (see FIG. 11A), a conventional guidewire is first inserted into a peripheral artery, such as the femoral, brachial, or radial artery, using known techniques, and advanced through the ascending aorta 510 into the left ventricle 512. A catheter is then slid over the guidewire. The operator then advances and positions the catheter into the left ventricle 512, using a known visualization modality, e.g. X ray imaging along with radio-opaque markers 14 on the distal end, or contrast agent. The operator then replaces the guidewire with the multisensor guidewire 100 in the lumen of the catheter. The operator advances the multisensor guidewire 100 through the catheter and positions the distal end portion 103 of the multisensor guidewire 100 into the left ventricle 512 using visualization devices such as the radio-opaque markers 14 on its distal end 103. Then, the operator pulls back the catheter over the guidewire. Once the multisensor guidewire 100 is properly positioned, and is coupled to the control unit 151 to activate the optical sensors, the optical pressure sensors 10a, 10b and 10c directly measure the transvalvular pressure gradient of the aortic valve 511. As illustrated schematically in FIG. 11A, two pressure sensors 10a, 10b are positioned in the left ventricle 512 and one pressure sensor 10c is positioned in the aorta 510 just downstream of the aortic valve 511, to allow simultaneous measurements of pressure at three locations, i.e. both upstream and downstream of the valve. A series of measurements may be taken during several cardiac cycles. Although not illustrated in FIG. 11A, a flow sensor 20 may also be provided for simultaneous flow measurements. Measurements results may be displayed graphically, e.g. as a chart on the touch screen display 152 of the system controller 150 (see FIG. 1) showing the pressure gradient and flow. The control system may provide for multiple measurements to be averaged over several cycles, and/or may provide for cycle-to-cycle variations to be visualized. Thus, the operator can quickly and easily obtain transvalvular pressure gradient measurements. The valve area may also be computed when blood flow measurements are also available. Measurements may be made, for example, before and after valve replacement or valve repair procedures.

FIGS. 16A, 16B and 16C and FIGS. 17A, 17B and 17C are simplified schematics of the aortic heart valve 511 and left ventricle 512, illustrating the concept of aortic transvalvular pressure gradient as measured by the multisensor guidewire 100 using the method of the first embodiment described above, for a healthy heart and for a heart with stenoses 531, 532 and 533. In this particular example, the aortic transvalvular pressure gradient is the blood pressure measured by sensors at locations P1, P2 within the left ventricle 512 and P3 within the aortic root 510.

The function of the heart is to move de-oxygenated blood from the veins to the lungs and oxygenated blood from the lungs to the body via the arteries. The right side of the heart collects de-oxygenated blood in the right atrium 521 from large peripheral veins, such as, the inferior vena cavae 520. From the right atrium 521 the blood moves through the tricuspid valve 522 into the right ventricle 523. The right ventricle 523 pumps the de-oxygenated blood into the lungs via the pulmonary artery 525. Meanwhile, the left side of the heart collects oxygenated blood from the lungs into the left atrium 514. From the left atrium 514 the blood moves through the mitral valve 513 into the left ventricle 512. The left ventricle 512 then pumps the oxygenated blood out to the body through the aorta 510.

Figure 15:
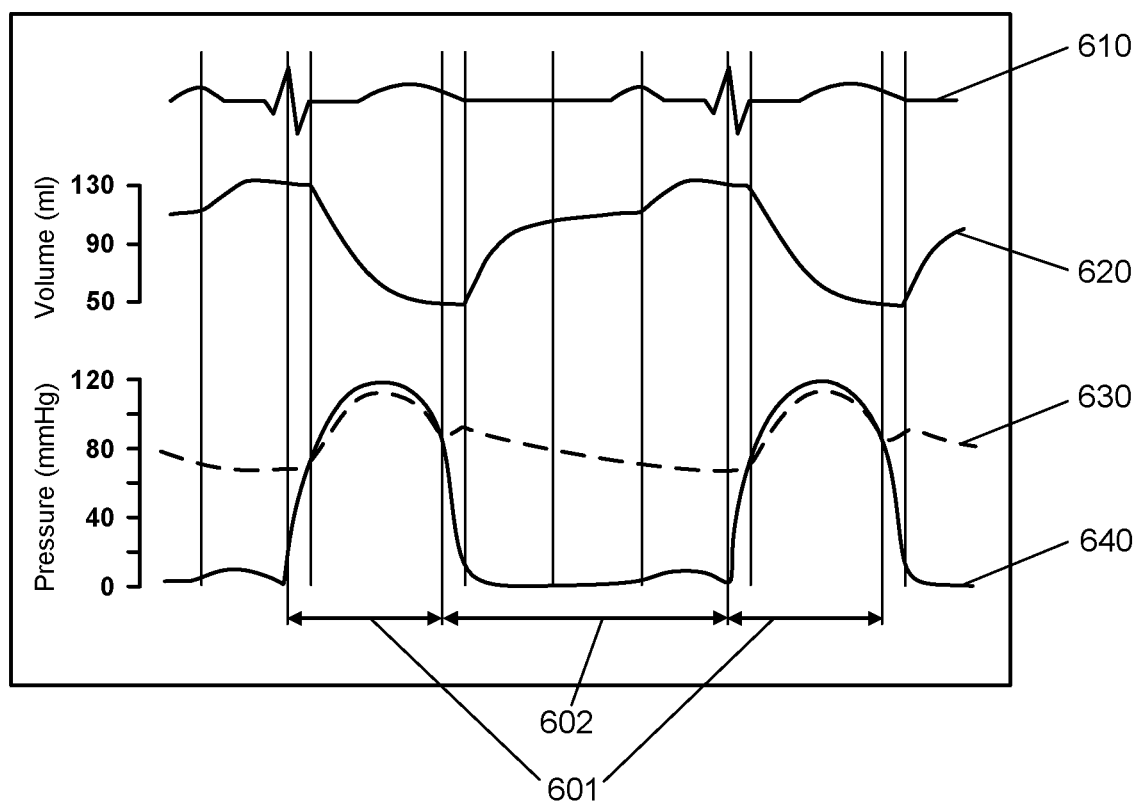
FIG. 15 shows a chart, known as a Wiggers diagram, showing typical cardiac blood flow and pressure curves during several heart cycles, for a healthy heart.

Throughout the cardiac cycle, blood pressure increases and decreases into the aortic root 510 and left ventricle 512, for example, as illustrated by the pressure curves 630 and 640, respectively, in FIG. 15, which shows curves typical of a healthy heart. The cardiac cycle is coordinated by a series of electrical impulses 610 that are produced by specialized heart cells. The ventricular systole 601 is the period of time when the heart muscles (myocardium) of the right 523 and left ventricles 512 almost simultaneously contract to send the blood through the circulatory system, abruptly decreasing the volume of blood within the ventricles 620. The ventricular diastole 602 is the period of time when the ventricles 620 relax after contraction in preparation for refilling with circulating blood. During ventricular diastole 602, the pressure in the left ventricle 640 drops to a minimum value and the volume of blood within the ventricle increases 620.

Figure 16A:
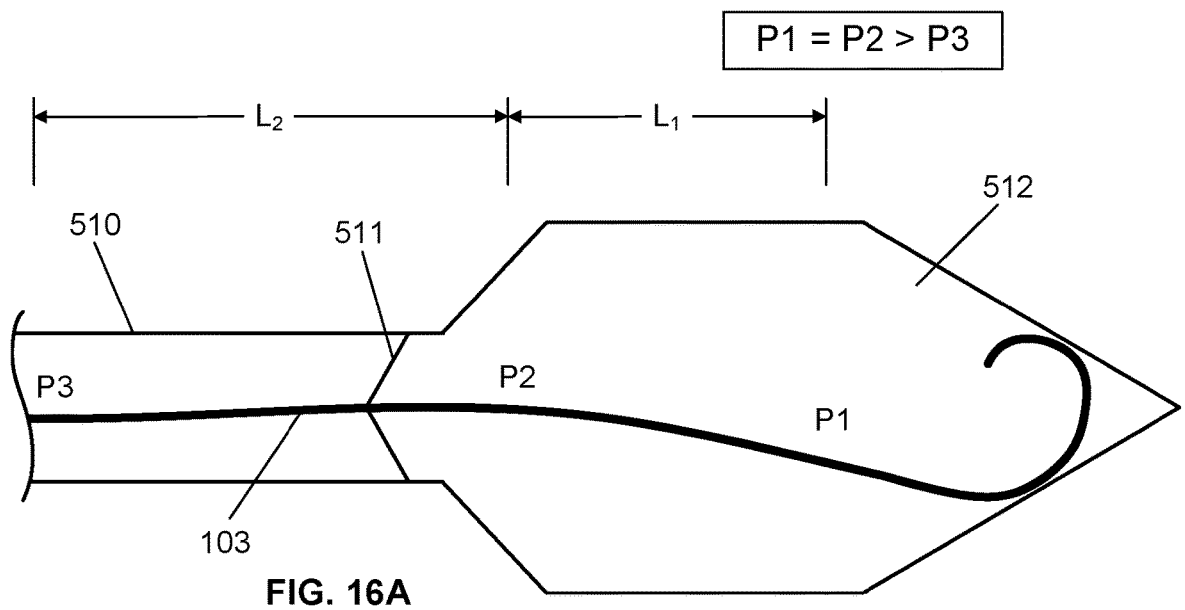
FIGS. 16A, 16B and 16C show simplified schematics representing the aortic heart valve and left ventricle in a healthy heart, with the multisensor guidewire inserted through the aortic valve with first and second optical pressure sensors P1 and P2 positioned within the ventricle and the third optical pressure sensor P3 positioned within the aorta for measurement of a transvalvular pressure gradient through the aortic valve in a healthy heart, with the heart valve in closed, semi-closed/open and open positions respectively.
Figure 16B:
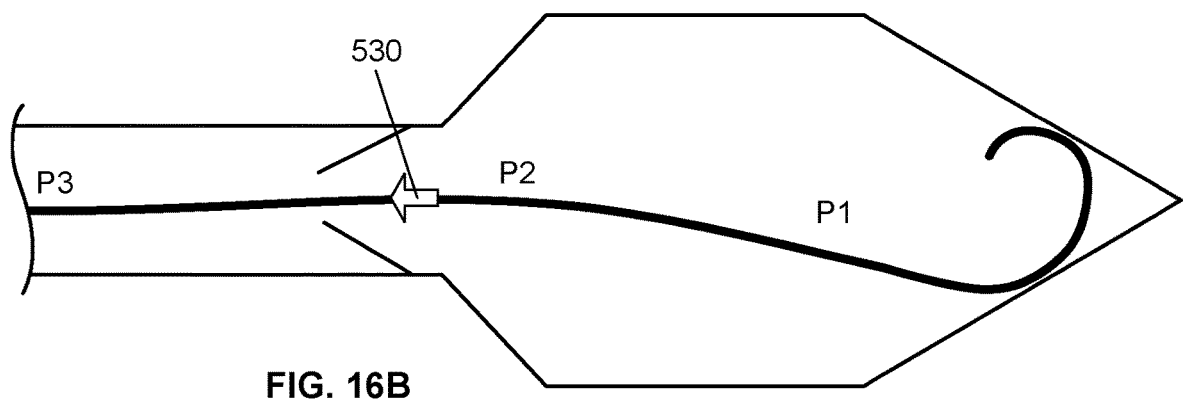
Figure 16C:
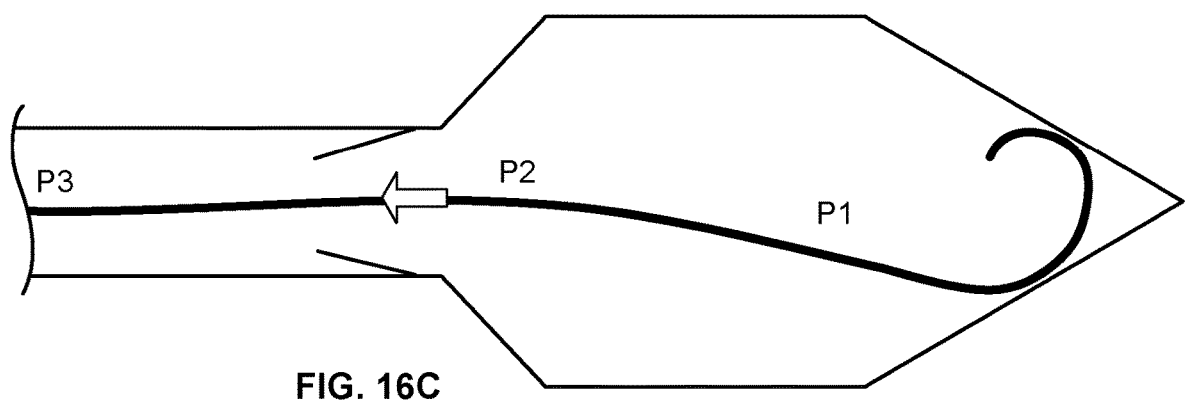

The left heart without lesions, illustrated in FIGS. 16A, 16B and 16C, would generate aortic and ventricular pressure curves similar to curves 630 and 640, respectively, in FIG. 15. However, the heart illustrated in FIGS. 17A, 17B and 17C has multiple sites of potential blood flow 530 obstructions 531, 532 and 533. In some cases, the operator of the multisensor guidewire 100 might want to measure the blood pressure at several locations, within the root of the aorta 510 in order to assess a subvalvular aortic stenosis 533 or a supravalvular aortic stenosis 531.

Figure 18:
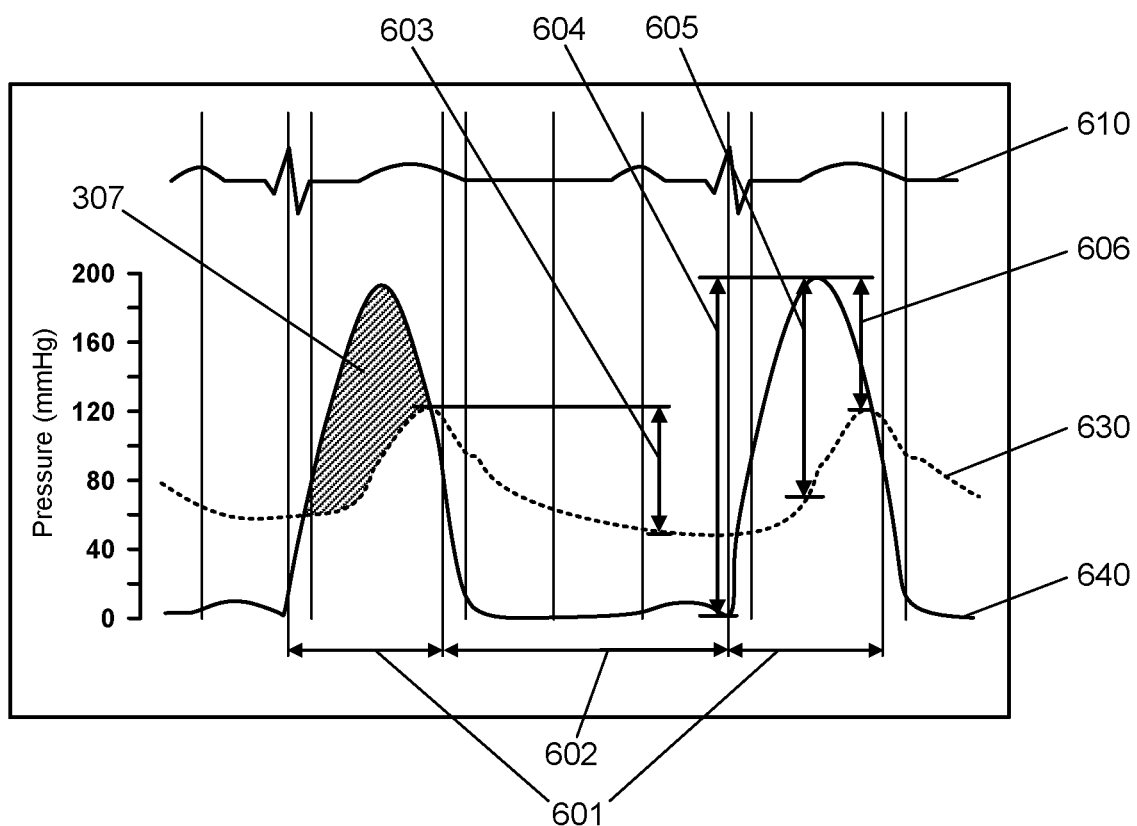
FIG. 18 shows a chart showing typical variations to the blood flow or pressure curves, during several cardiac cycles, due to cardiac stenosis.

The cardiac hemodynamic data collected from a patient's heart allow a clinician to assess the physiological significance of stenosic lesions. The aortic and ventricular pressure curves from a patient's heart are compared with expected pressure curves. FIG. 18 illustrates typical differences between the aortic 630 and ventricular 640 pressure curves due to intracardiac obstructions. Some of those variations include the maximal difference 605 and the peak-to-peak difference 606 between curves 630 and 640. The area 607 between the aortic pressure curve 630 and ventricle pressure curve 640 is also used to assess the physiological significance of stenosic lesions. The difference between the amplitude 603, 604 of the aortic 630 and ventricle 640 pressure curves is also key information for the clinician.

The medical reference literature relating to cardiac catheterization and hemodynamics provides different possible variations of the aortic 630 and ventricular 640 pressure curves along with the possible causes in order to identify the proper medical diagnosis. For example, cardiac hemodynamic curves, such as shown in FIG. 18, along with analysis of the curves, are provided on pages 647 to 653 of the reference book entitled Grossman's cardiac catheterization, angiography, and intervention by Donald S. Baim and William Grossman.

As indicated, when the valve is closed as shown in FIG. 16A, the pressures P1 and P2 measured by first and second sensors 10a and 10b placed in the left ventricle would be equal and lower than the pressure P3 measured by the third sensor in the aorta during the ventricular diastole 302. During the ventricular systole 301, when the aortic valve begins to open, FIG. 16B, the pressures P1, P2 and P3 increase and when the aortic valve is fully open, FIG. 16C, P1, P2 and P3 are similar. The specific form of the pressure traces P1, P2, P3 generated by each sensor provides the interventional cardiologist with direct, real-time data to aid in diagnosis and assessment of valve performance before and after TVT.

Figure 17A:
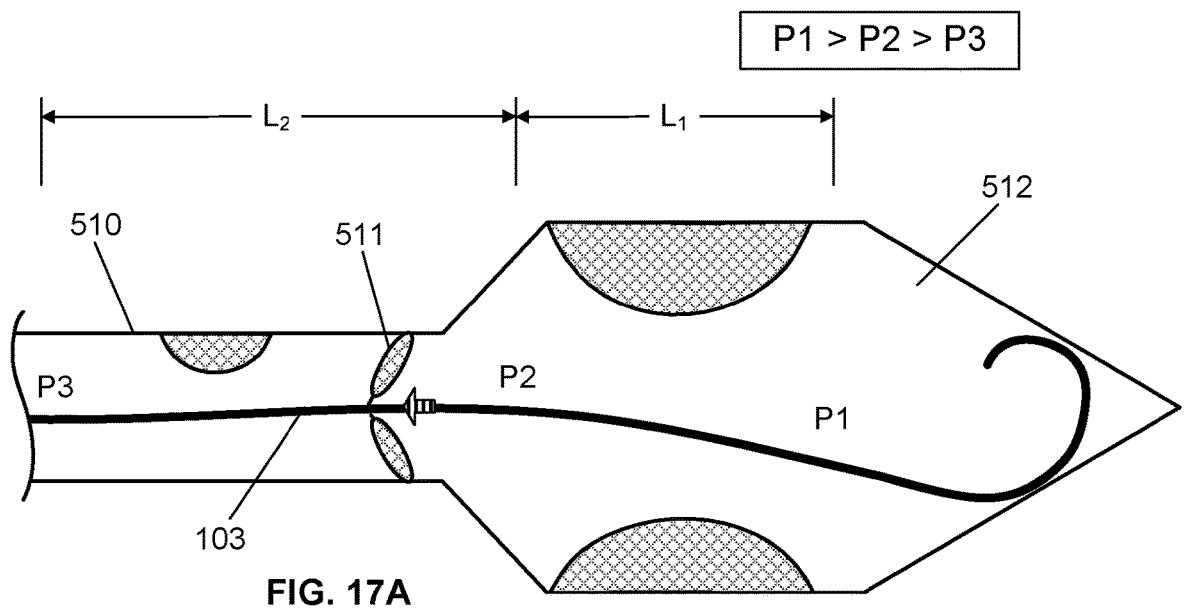
FIGS. 17A, 17B and 17C show similar simplified schematics representing the aortic heart valve and left ventricle, in which shaded areas represent stenoses, with the multisensor guidewire inserted through the aortic valve with first and second optical pressure sensors P1 and P2 positioned within the ventricle and the third optical pressure sensor P3 positioned within the aorta for measurement of a transvalvular pressure gradient through the aortic valve in a diseased heart, with the heart valve in closed, semi-closed/open and open positions respectively.
Figure 17B:
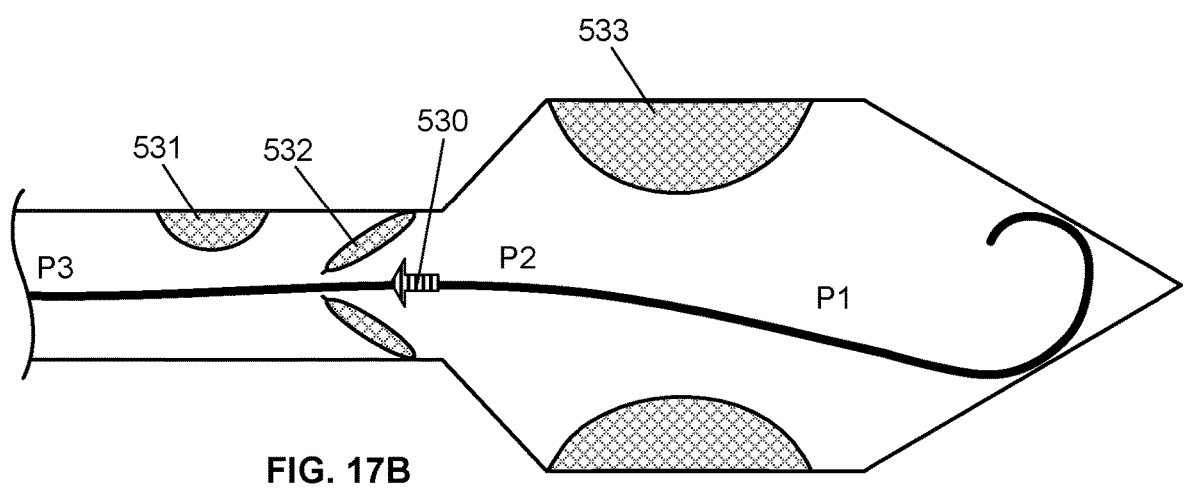
Figure 17C:
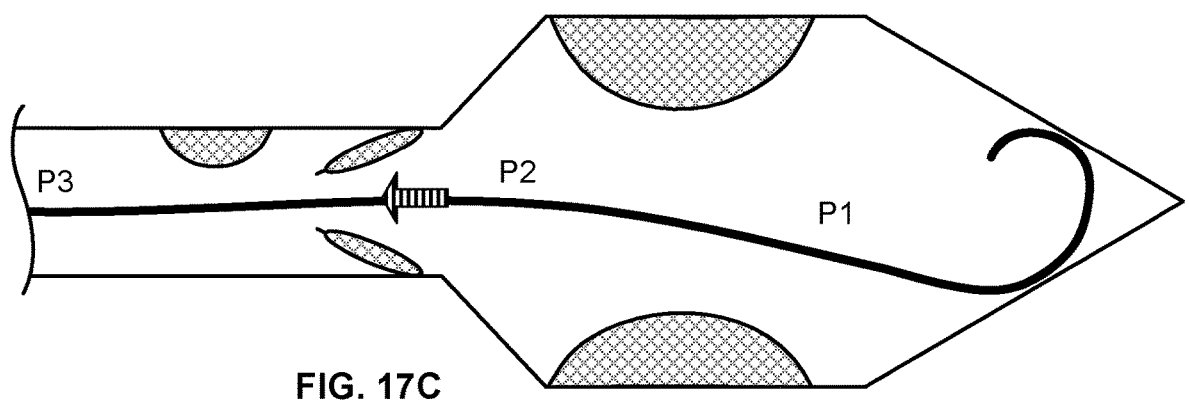

However, as illustrated schematically in FIGS. 17A, 17B and 17C, when the heart has subvalvular aortic stenosis 533, for example, the pressure traces P1, P2 and P3 will differ. To detect and assess the severity of subvalvular stenosis 533, the two distal pressure sensors at locations P1 and P2 must be located in the left ventricle on each side of stenosis 533 while the proximal pressure sensor P3 must be located within the root of the aorta 510 at a certain distance from the aortic valve 511. Therefore, as shown, the distance $L_1$ (typically about 20 mm) between sensors 10a, 10b is shorter than the distance $L_2$ (typically about 50 mm or 60 mm) between sensors 10b, 10c, which length is determined by the dimensions of the heart or vascular region to be monitored. As illustrated schematically in FIGS. 17A, 17B and 17C, when the heart has subvalvular aortic stenosis 533, for example, the pressure traces P1, P2 and P3 will differ.

Importantly, the specific positioning of the multiple sensors enables measurements that permit the determination of whether the stenosis is strictly associated with the valve or not, and whether it is associated with a subvalvular stenosis (e.g. sub-aortic hypertrophic stenosis) or supravalvular stenosis. It also enables measurements that permit the determination of the functional severity of subvalvular stenosis.

Manufacturability

During prototyping, a number of challenges have been discovered in attempting to accommodate a plurality of optical sensors and optical fibers within a multisensor guidewires having a required stiffness e.g. 60 GPa, and a sufficiently small outside diameter ≤1 mm, and typically 0.89 mm or 0.035 inch, for use in TVT. Until smaller diameter optical sensors and optical fibers are developed and characterized, a design of core wire is required to accommodate multiple fibers and sensors without unduly reducing the stiffness of the core wire. In considering manufacturing tolerances for the optical components and for the guidewire coil and core wire, it has also been discovered that there are currently significant manufacturing challenges in providing multisensor guidewires of diameter ≤1 mm comprising a grooved core wire and multiple optical fibers and optical sensors.

Core wires are conventionally circular in cross-section and manufactured by wire drawing or wire rolling processes, e.g., from suitable metals and alloys, usually medical grade stainless steel, to provide the required mechanical properties, e.g., stiffness, flexibility, tensile strength. Thus, conventionally, small diameter round core wires with sufficient stiffness for guidewires are manufactured by drawing (pulling) a wire through successively smaller dies, or rolling the wire through successively smaller dies.

Manufacturing a sub-millimeter diameter core wire with straight or helical grooves along its length to accommodate individual optical fibers of approximately 100 μm diameter, presents challenges for conventional core wire manufacturing facilities. Currently, specialized equipment is needed. Standard manufacturing equipment cannot be used to provide grooved core wires without expensive modifications to the equipment and processes. In practice, the core wire structure of the first embodiment, comprising multiple small grooves spaced circumferentially around the wire, each accommodating an individual optical fiber is therefore complex and/or expensive to manufacture using conventional wire drawing and wire rolling equipment.

Since medical guidewires are intended to be disposable, i.e. for single-use only, an alternative or lower cost manufacturing solution is desirable. However, for medical applications, it will also be appreciated that manufacturing facilities must also be capable of meeting required standards for medical devices. It also desirable to use materials, e.g., metals and alloys, such as medical grade stainless steel, which already have regulatory approval for medical use and for which extensive manufacturing experience is already available. It is envisaged that alternative materials, such as suitable polymer and composite materials could potentially be used for manufacture of core wires, e.g. if they provide appropriate stiffness and mechanical properties. However, conventional medical grade metals and alloys are preferred.

However, it has been found to be challenging to manufacture grooved stainless steel core wires of the required size and tolerances by known wire drawing processes, particularly a plurality of small grooves to accommodate individual fibers. Also, using existing wire drawing equipment used for medical guidewires, it is difficult to control rotation of grooves along the length of the wire, e.g. to form helical grooves of a pre-defined pitch. While it is expected that manufacturing challenges may be overcome in the near future, a core wire with a cross-sectional profile providing a simpler channel surface e.g. comprising a single larger groove accommodating multiple fibers, which can be manufactured by conventional grinding, wire-drawing or wire-rolling provides an alternative, more cost effective solution in the near term.

For example, the multisensor guidewire of the second embodiment having a core wire that has a cross-sectional profile which is shaped with a contoured channel surface as illustrated in FIG. 8, i.e. a scalloped channel surface which may be formed by wire-rolling or wire drawing processes. The guidewire has an outside diameter of 0.89 mm (0.035 inch) and comprising three Fabry-Pérot optical sensors, each coupled to individual optical fibers having a diameter $D_F$ of 100±0 4 μm (0.0039"±0.0002"), a core wire formed having a cross-section as shown in FIG. 8, formed by wire rolling, may have the following dimensions: $R_1$=0.0145"+/−0.00037"; $R_2$=0.009"+/−0.0015"; $R_F$=0.003"+/−0.0015"; $R_{ext}$=0.005"+/−0.0015"; and w=0.010". Thus, for example, to allow for these manufacturing tolerances, a clearance $C_L$ of 0.001" (1 mil) is required.

In other variants or modifications of these embodiments of a core wire formed by conventional wire rolling or wire drawing, other cross-sectional profiles may be provided with one or more grooves, each groove accommodating a plurality of optical fibers. For a single groove, the core wire has, for example, a generally D-shaped cross-sectional profile or a lune-shaped profile. Other more complex profiles with multiple contoured grooves are also contemplated, such as those shown in FIGS. 10A, 10B and 10C. Provided that the core wire structures of these alternative embodiments are dimensioned to be formed by known wire drawing or wire rolling processes, they offer some advantages with respect to manufacturability and cost of manufacturing relative to structures with a plurality of smaller grooves, where each groove accommodates a single fiber and sensor.

Also, it is believed that formation of a channel surface by wire rolling, rather than wire drawing, may be advantageous for some applications. For example, during rolling of a stainless steel wire, i.e. by compression of the core wire within a die, this process is expected to somewhat harden or stiffen the core wire surface region defining the channel surface. Thus, while a channel surface is created to form a space or channel between the core wire and outer coil of the guidewire to accommodate a plurality of optical fibers, a higher overall stiffness of the wire may be obtained for a wire of a particular diameter $D_{core}$.

Contact Force Sensor

Figure 22:
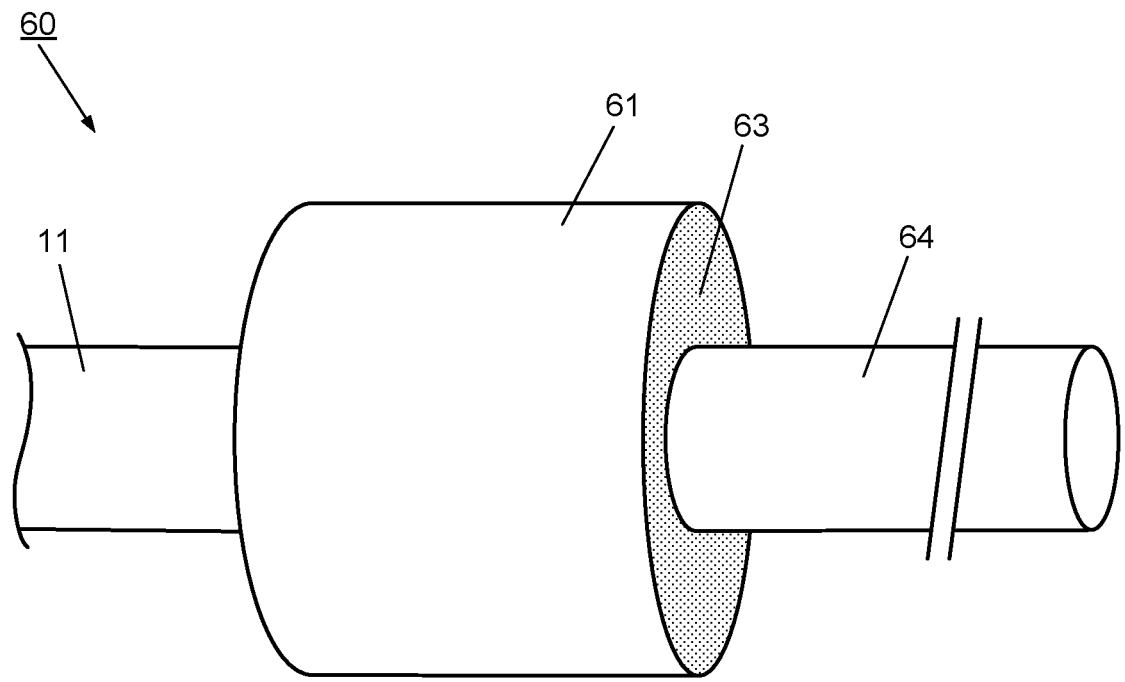
FIG. 22 illustrates schematically a side perspective view an optical contact force sensor (strain gauge) for use in a multisensor guidewire for cardiovascular use such as for TVT.
Figure 23:
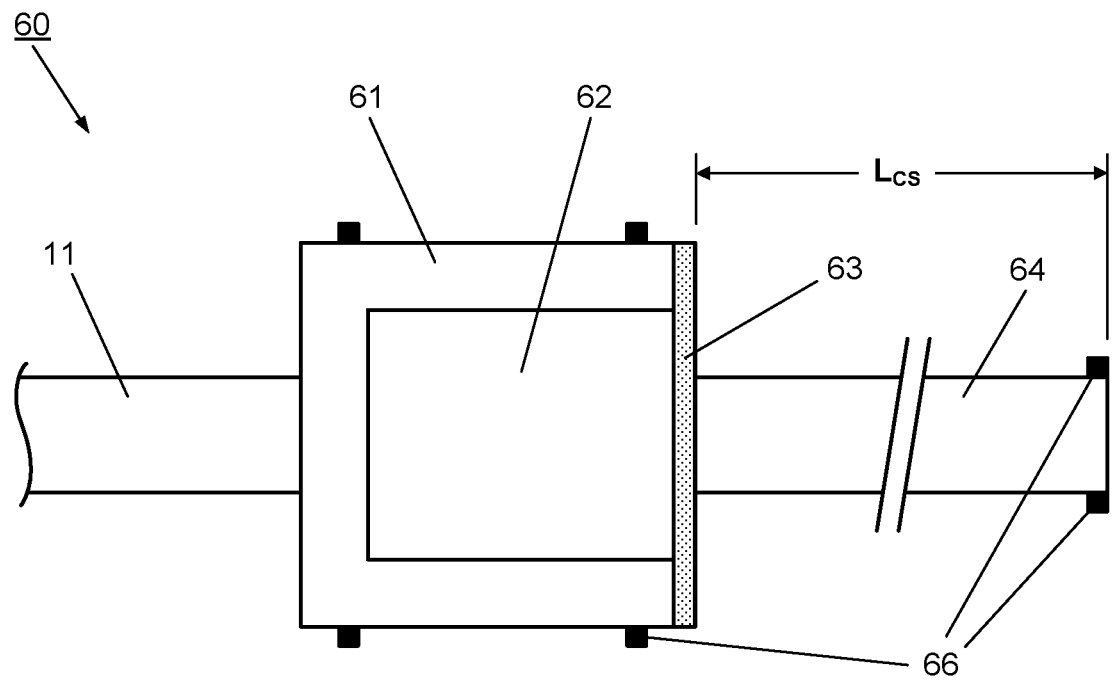
FIG. 23 illustrates a longitudinal cross sectional view of the optical contact force sensor (strain gauge) of FIG. 22.
Figure 24:
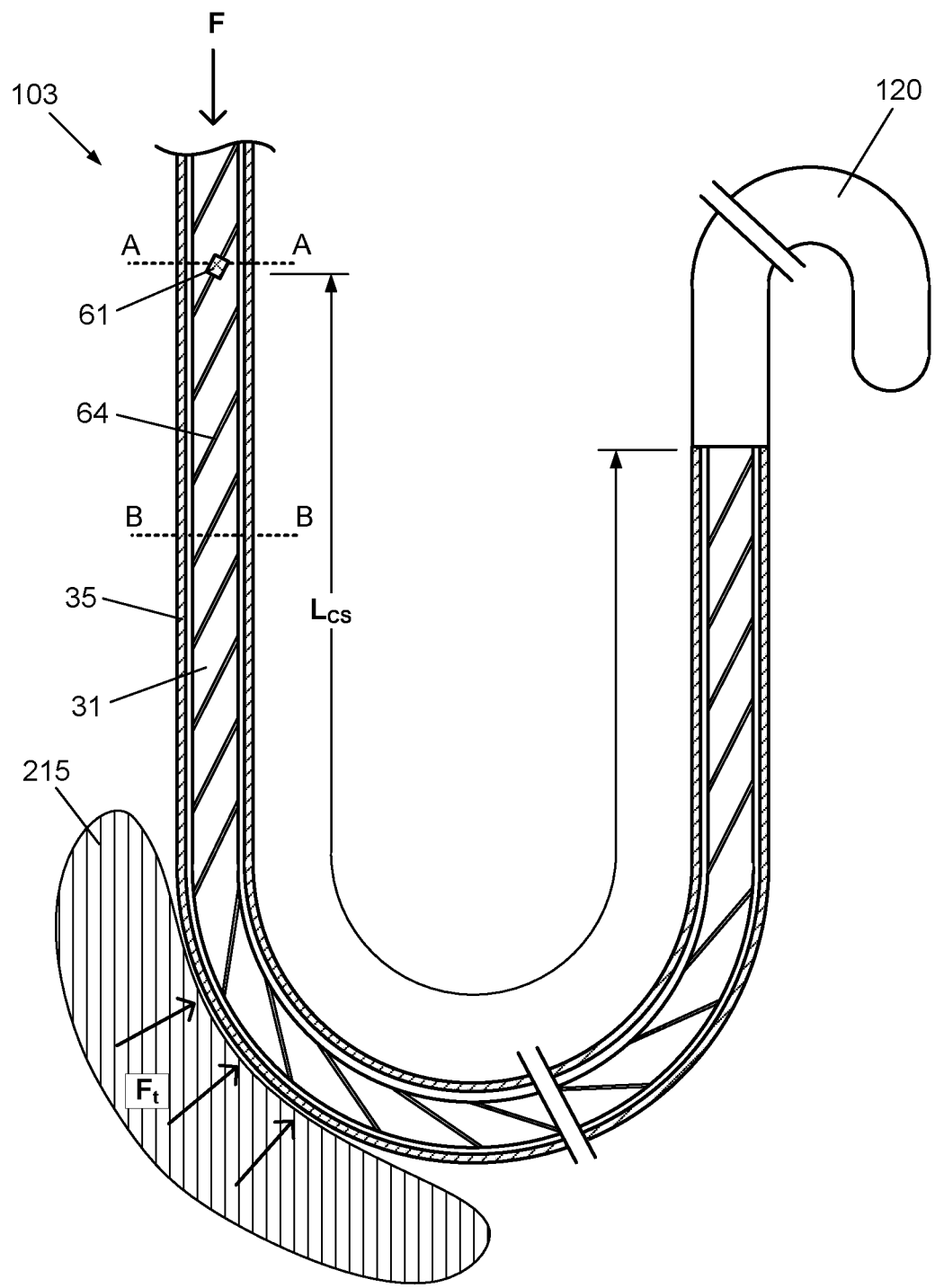
FIG. 24 illustrates schematically a longitudinal cross-sectional view showing details of the distal end portion of a multisensor guidewire of a third embodiment comprising a contact force sensor such as illustrated in FIG. 22.
Figure 25A:
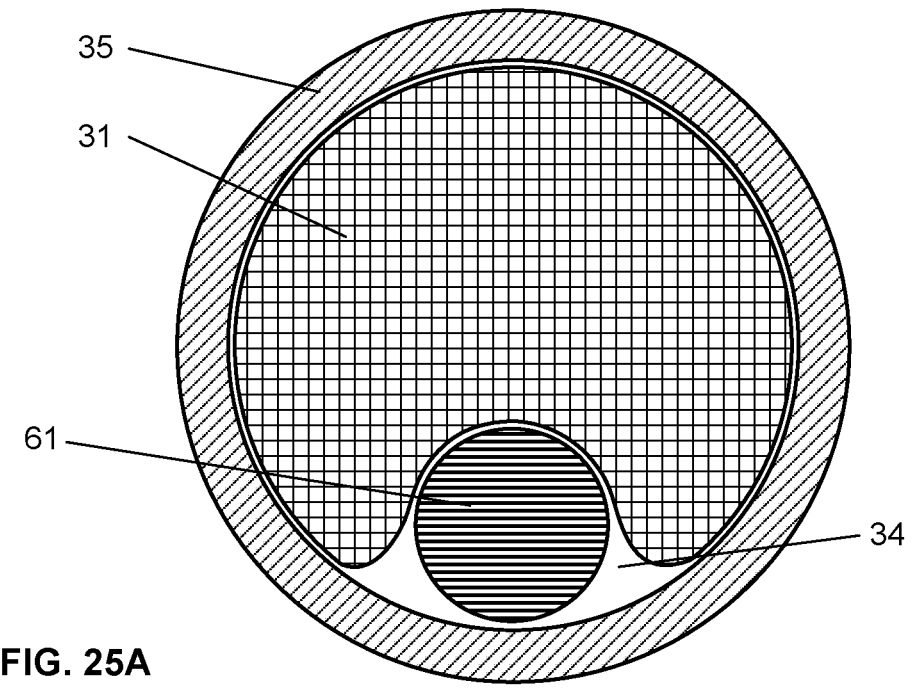
FIGS. 25A and 25B show enlarged axial cross-sectional views of the multisensor guidewire comprising a contact force sensor illustrated in FIG. 23 taken, respectively, through planes A-A and B-B indicated in FIG. 24.
Figure 25B:
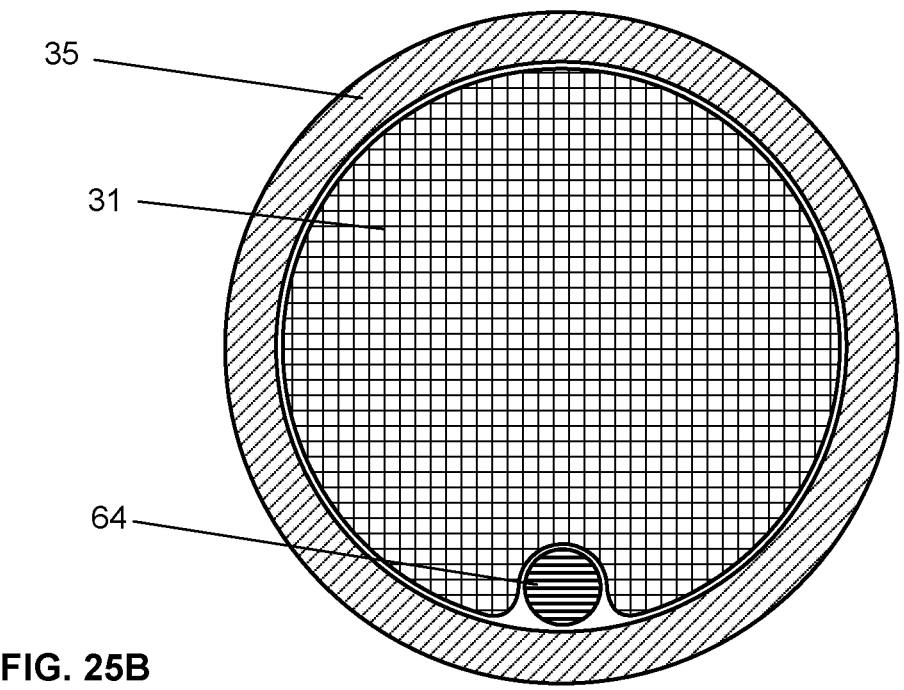

Beneficially, for use in TVT, the multisensor guidewire 100 is also capable of measuring a contact force of the guidewire against the wall of the heart, e.g. the wall of a diseased left ventricle. Thus, a guidewire according to another embodiment comprises an integral fiber-optic contact force sensor 60 as illustrated schematically in FIGS. 22, 23, 24, 25A and 25B e.g. an optical strain gauge type of sensor, located at a suitable position in or near the distal end portion 103. For example, as illustrated in FIGS. 22 and 23, the optical contact force sensor 60 comprises a Fabry-Pérot MOMS sensor 61 which is located in the distal end portion 103 and is coupled by a respective optical fiber 11 to an input output optical connector, e.g. to the micro-optical connector 140 as previously described. The cavity 62 and diaphragm 63 of the Fabry-Pérot MOMS sensor 61 is also coupled to a length $L_{CS}$ of a second optical fiber 64 which extends from the sensor 61 along the length $L_{CS}$ of the distal end of the guidewire, towards the flexible tip 120. As illustrated in FIGS. 25A and 25B, the second optical fiber 64 sits in a helical groove 32 in the core wire which is enlarged to form a recess 34 at A-A to accommodate the sensor 61. As indicated in FIG. 23, the sensor 61 and the end of fiber 64 are fixed to the core wire at points 66. This arrangement allows for the sensor 61 to detect and measure a contact force applied along a length $L_{CS}$ of the guidewire when it contacts the internal heart walls 215 of the heart as indicated schematically in FIG. 24. Such a contact force sensor 60 provides information and feedback to the cardiologist regarding the force F being applied, e.g. when a detected contact force approaches or exceeds a threshold $F_t$ that may cause tissue damage, or potentially even cause fatal injuries during TVT, an alert may be provided to the operator.

Figure 26:
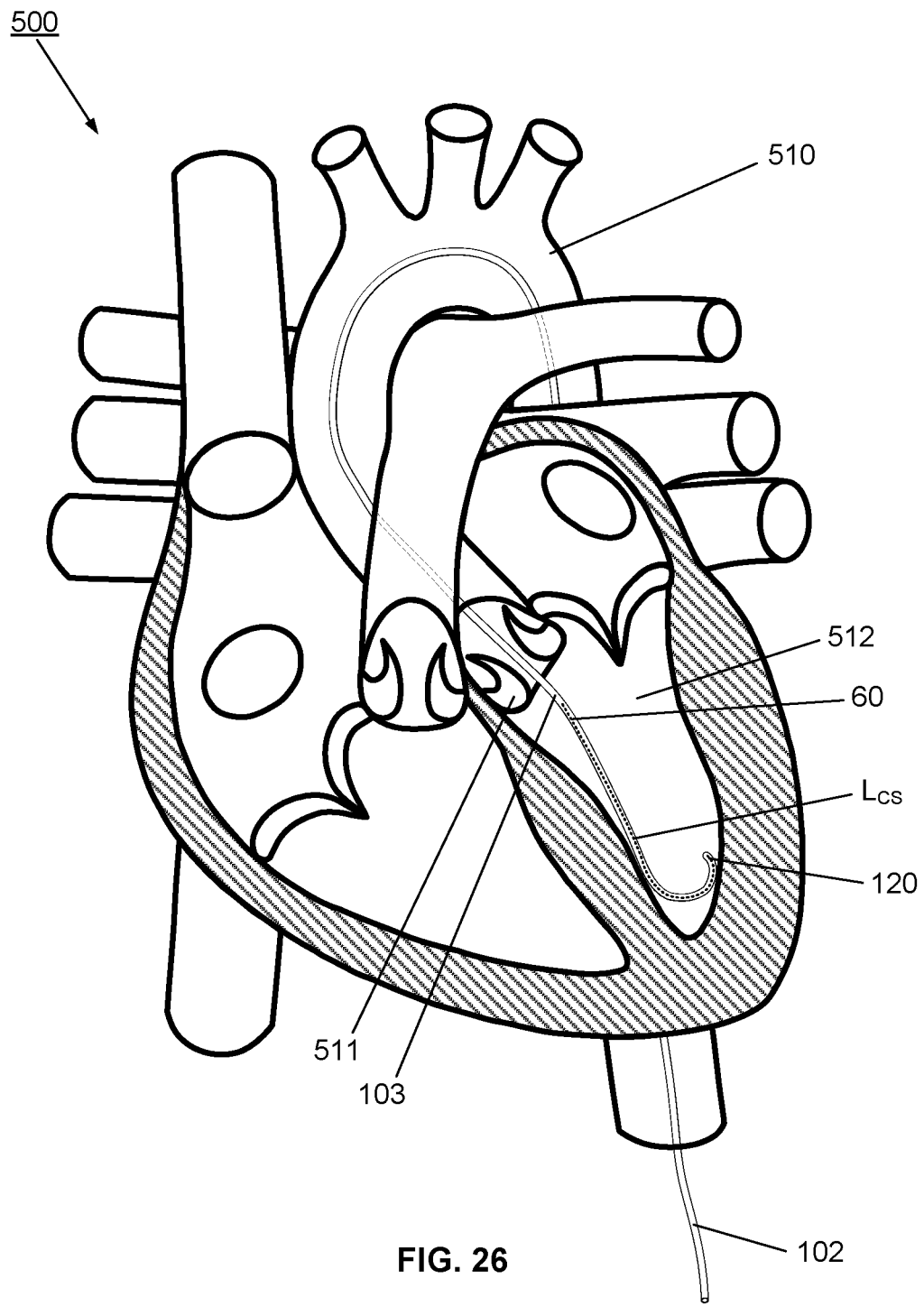
FIG. 26 shows a schematic diagram of a human heart to illustrate placement within the left ventricle of a multisensor guidewire, similar to that shown in FIG. 23, for sensing a contact force, e.g. during a TAVI procedure or during measurement of cardiovascular parameters before, during and after the TAVI procedure.

Thus for example the guidewire 100 may comprises three optical pressure sensors 10a, 10b, 10c as described above with reference to FIGS. 2 and 3, optionally a flow sensor 20 located in the distal end portion, and a contact force sensor 60 located in a region between the distal end portion 103 containing the optical pressure sensors and the flexible distal tip 120, to sense a contact force applied near the end of the guidewire, along the length $L_{ts}$ indicated by the dotted line in FIG. 26.

Flexible Preformed Three-Dimensional Curved Tip

Figure 27B:
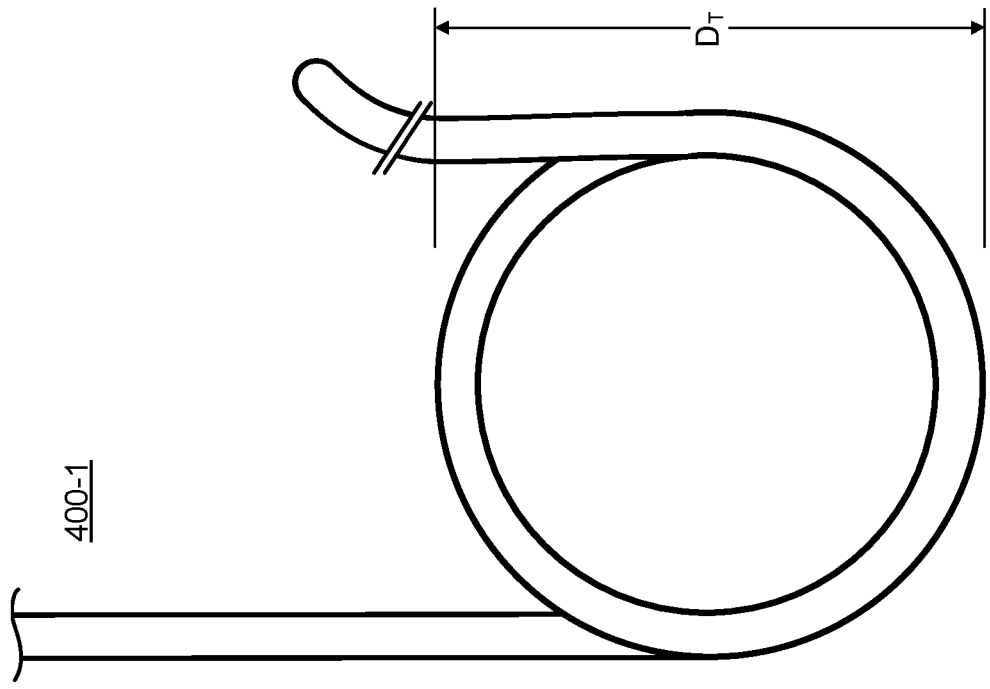
FIGS. 27A and 27B, show enlarged views of the distal end of a guidewire wherein the tip comprises pre-formed helical tip of a first embodiment.
Figure 27A:
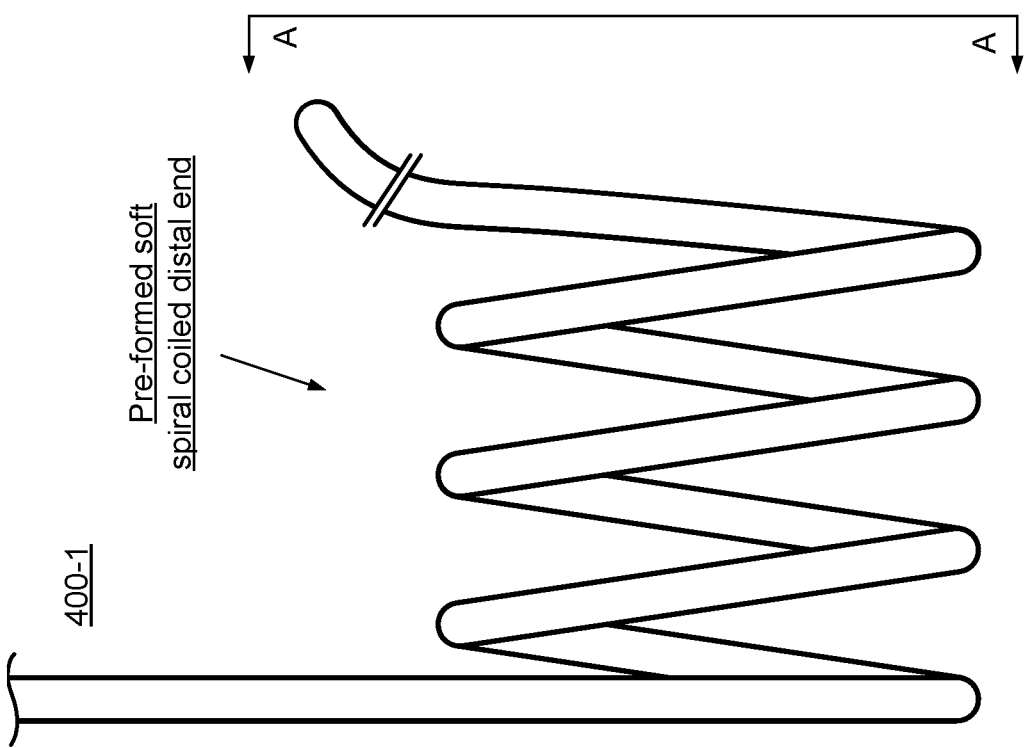
Figure 28:
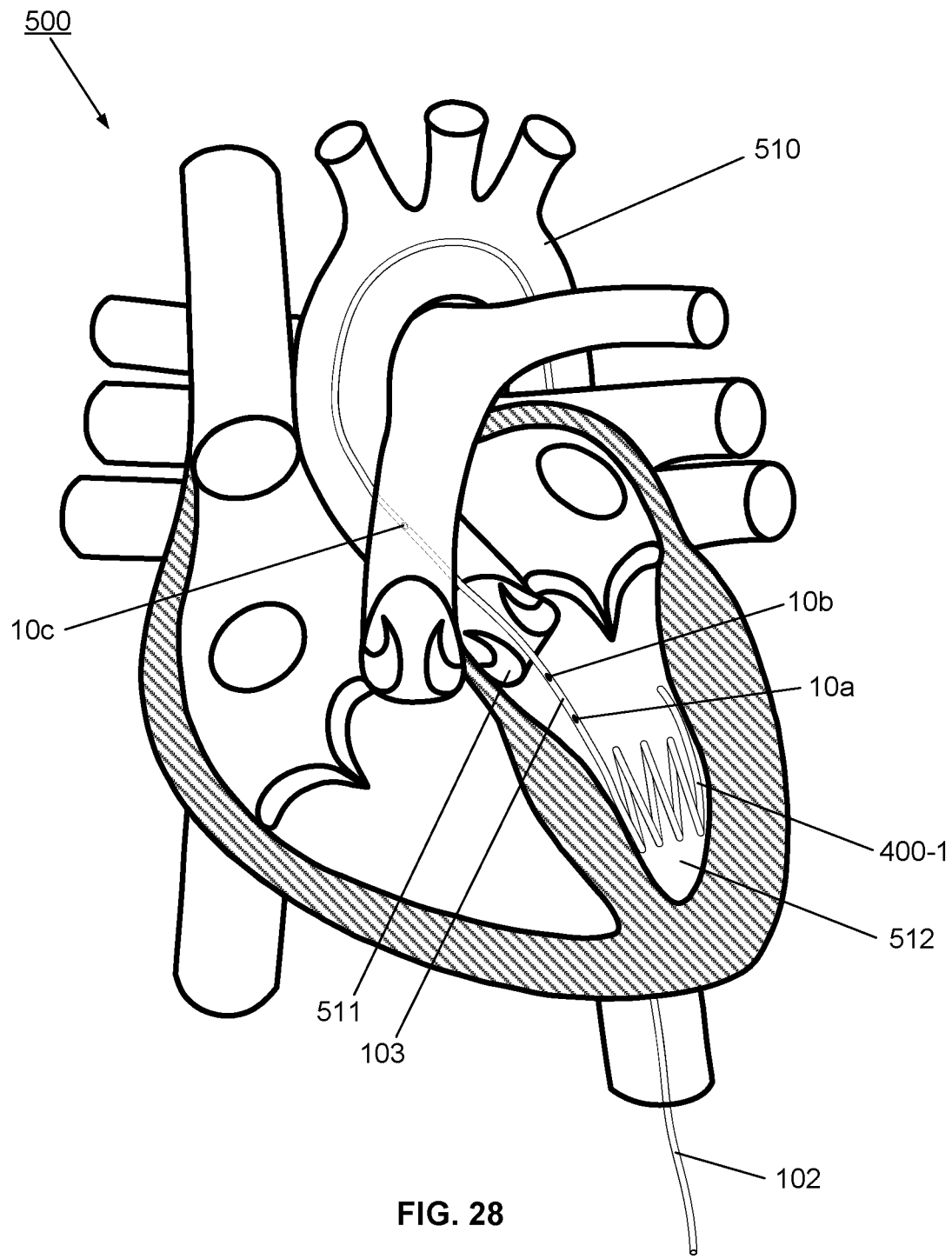
FIG. 28 shows a schematic diagram of a human heart to illustrate placement of within the left ventricle of a guidewire comprising a flexible pre-formed helical tip as shown in FIGS. 27A and 27B.
Figure 29B:
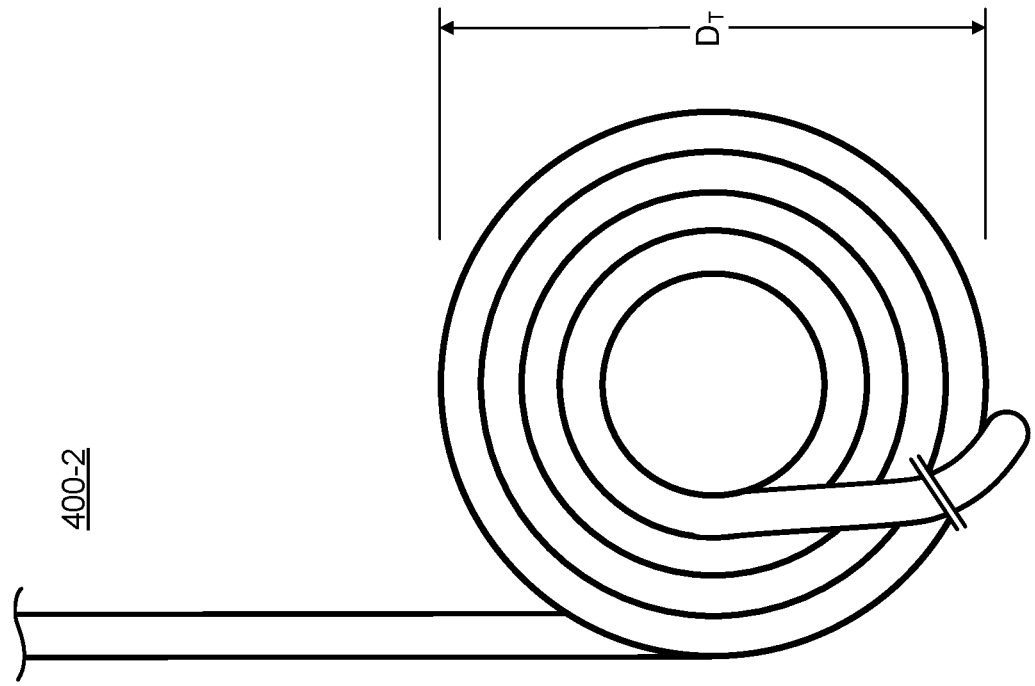
FIGS. 29A and 29B show enlarged views of views of the distal end of a guidewire wherein the tip comprises a pre-formed helical tip of another embodiment.
Figure 29A:
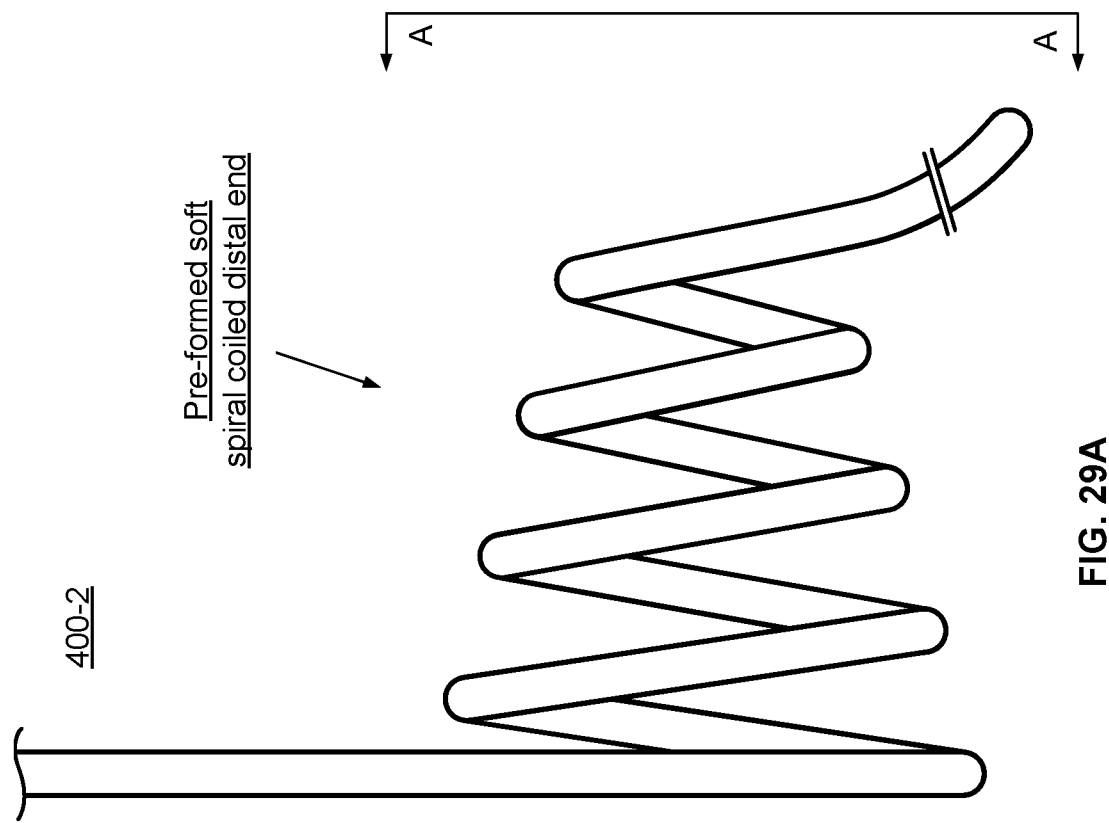
Figure 30:
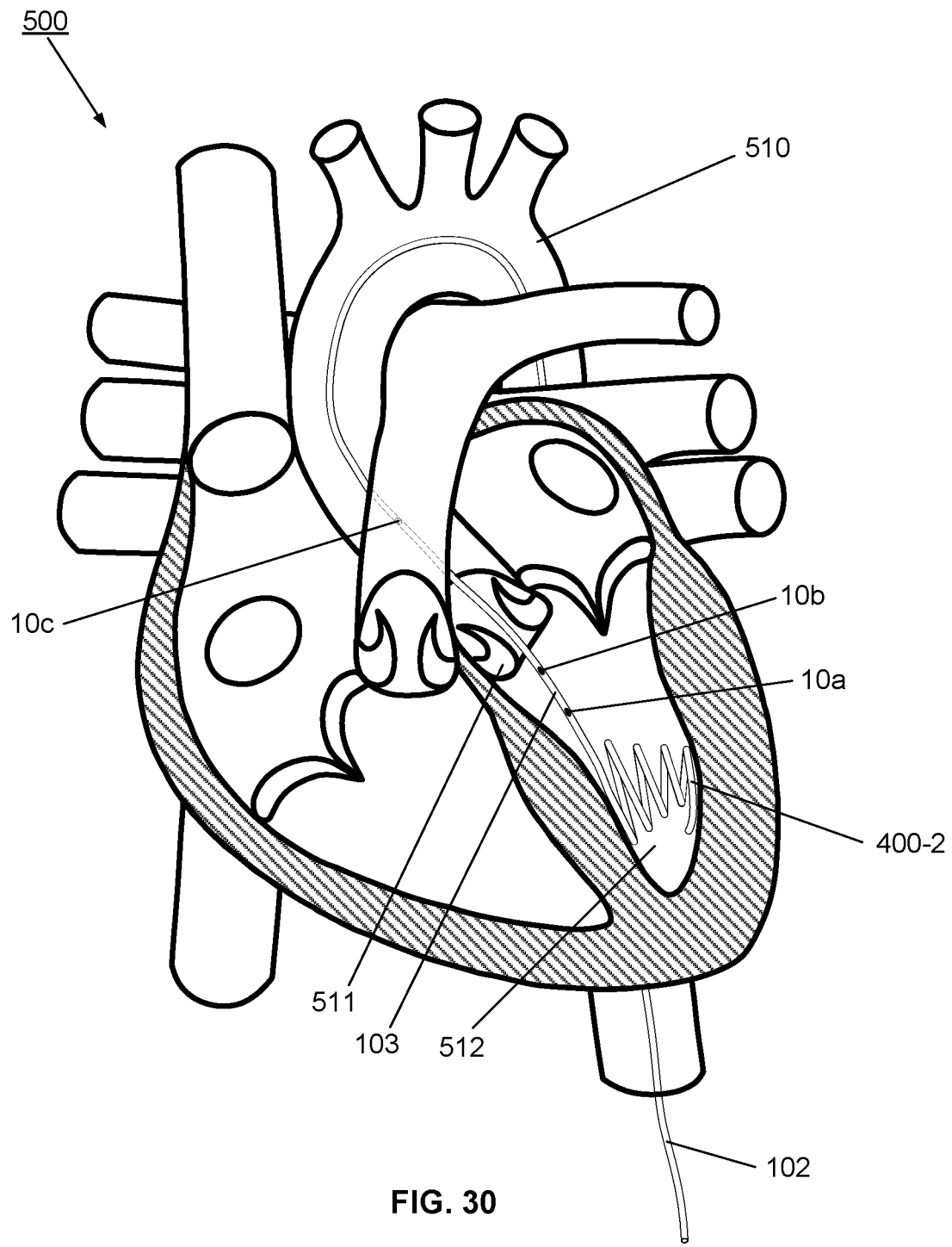
FIG. 30 shows a schematic diagram of a human heart to illustrate placement within the left ventricle of a multisensor support guidewire, comprising a pre-formed helical tip as shown in FIGS. 29A and 29B.

To assist in atraumatic insertion and anchoring of the guidewire 100 within the ventricle during TVT, it is desirable to use a flexible preformed tip such as a J tip or other curved tip. FIGS. 27A and 27B show two views of a pre-formed flexible tip 400-1 having a three-dimensional form, specifically in this embodiment, a pre-formed helical tip, of coil diameter $D_T$, e.g. 5 cm, which resembles part of a telephone cord or a pigtail. A tip 400-2 of another embodiment, as illustrated in FIGS. 29A and 29B, comprises a pre-formed helix that is tapered to resemble the form of a snail shell. FIGS. 28 and 30, respectively, represent schematically the placement of these pre-formed helical tips 400-1 and 400-2 in left ventricle 512 for TVT or for diagnostic measurements using the optical pressure sensors 100. This three-dimensional pre-formed structure is proposed for improved support of the guidewire in each of the X, Y and Z directions during TVT procedures. Such a structure can assist in providing support for the guidewire in a safer manner.

Further Embodiments

It will be appreciated that in alternative embodiments or variants of the present embodiments, one or more features disclosed herein may be combined in different combinations or with one or more features disclosed herein and in the related patent applications referenced herein.

A core wire having multiple straight or helical grooves along its length accommodates a plurality of optical sensors and optical fibers within a required diameter without significantly reducing the stiffness of the core wire or its torque characteristics. For lower cost manufacturing, the core wire may have a simpler channel surface, such as, one or more grooves formed by grinding, or a single groove with a contoured or scalloped surface structure formed by wire-rolling.

Additionally, for valve replacement, since the guidewire must be firmly anchored within the ventricle for accurate measurements and for positioning of a replacement valve, an optional preformed curved tip, such as a pre-formed "snail" tip as assists in anchoring the guidewire in the ventricle during TAVI.

Furthermore, an optional contact force sensor near the tip provides important feedback to the interventional cardiologist relating to the force being applied or transferred internally to the heart wall. Feedback to the cardiologist to indicate when a contact force exceeds a threshold level, together with a specially shaped pre-formed flexible tip, assists in reducing trauma to the tissues of the heart, and in particular reduces risk of perforation the ventricular wall. Thus, the interventional cardiologist is offered a guidewire which simplifies both diagnostic measurements and TVT procedures, including heart valve implantation, and which could potentially assist with reducing mortality and avoiding trauma or perforations.

INDUSTRIAL APPLICABILITY

Currently, patient mortality rate after TVT is significant, with some studies reporting mortality in a range of 10%-15%. As shown by a growing number of studies, interventional cardiologists need accurate data, i.e. measurements of cardiovascular parameters to assess the functional performance of a patient's heart valves before and after TVT, to obtain a better understanding of the issues and to find solutions to reduce mortality and reduce the need for re-intervention after TVT. Methods currently available to diagnose cardiac valve disease do not allow interventional cardiologists to resolve this major issue.

Systems and apparatus according to embodiments of the invention comprise multisensor support guidewires for use in TVT, such as TAVI. These "Smart Guidewires™" not only have the required mechanical characteristics to act as support guidewires for TVT, they comprise sensors for making direct (in-situ) measurements of important parameters, including measurement of a transvalvular blood pressure gradient and optionally blood flow, for evaluation of performance of the heart and the heart valves immediately before and after TVT. A single-use disposable guidewire integrating multiple optical sensors allows for quickly providing real-time accurate quantitative data related to functional performance of heart valves right before and after TVT.

Although embodiments of the invention have been described and illustrated in detail, it is to be clearly understood that the same is by way of illustration and example only and not to be taken by way of limitation, the scope of the present invention being limited only by the appended claims.

The invention claimed is:
1. A multisensor guidewire assembly for measuring blood pressure concurrently at multiple locations during transcatheter heart valve therapies (TVT),
the multisensor guidewire assembly comprising distal and proximal parts connected by a micro optical coupler that is separable to enable over the guidewire delivery of TVT components;
the distal part of the multisensor guidewire assembly comprising:

a guidewire comprising a tubular covering layer comprising a flexible coil (coil) of a first stiffness, the coil having a length extending between a proximal end and a distal end, an inner member having a second stiffness extending within the coil from the proximal end to the distal end; the distal end comprising a flexible distal tip; and the proximal end comprising a male part of the optical coupler;

a plurality of optical sensors and a plurality of optical fibers; a sensor end of each optical fiber being attached and optically coupled to an individual one of the optical sensors; the plurality of optical sensors comprising at least two optical pressure sensors;

the plurality of optical fibers and the inner member forming an assembly wherein sensor ends of each optical fiber are arranged to form a sensor arrangement wherein said plurality of optical sensors are positioned at respective sensor locations spaced apart lengthwise within a distal end portion of the guidewire;

a proximal end of each of the plurality of optical fibers being coupled to an optical input/output comprising the male part of the optical coupler;

the proximal part of the guidewire assembly comprising:

a flexible optical cable containing a plurality of optical fibers and having at its distal end a female part of the optical coupler and at its proximal end an optical input/output for connection to an optical controller;

the male and female parts of the optical coupler being configured to mutually align and optically couple the plurality of optical fibers of the distal and proximal parts of the guidewire assembly for operation of the optical pressure sensors; and the male and female parts of the optical coupler being separable and the male part of the optical coupler having an outside diameter that accepts TVT components for over the guidewire delivery.

2. The multisensor guidewire assembly of claim 1, wherein the male part of the optical coupler has an outside diameter no greater than a maximum outside diameter of the coil of the guidewire.

3. The multisensor guidewire assembly of claim 2, wherein the inner member comprises a core wire and a proximal end of the core wire comprises a tapered portion that extends to form a core of the male part and the plurality of optical fibers extend around the tapered portion, around the core, and through a surrounding body of the male part.

4. The multisensor guidewire assembly of claim 3, wherein the optical coupler further comprises at least one of:

alignment means comprising corresponding facets of the male and female parts of the optical coupler for mutually aligning the optical fibers; and fastening means for locking together the male and female parts of the optical coupler.

5. The multisensor guidewire assembly of claim 1, wherein the male part of the optical coupler comprises a ferrule carrying an array of ports for the plurality of optical fibers of the distal part of the guidewire assembly, and the female part comprises a body carrying a corresponding array of ports for the optical fibers of the proximal part of the guidewire assembly.

6. The multisensor guidewire assembly of claim 1, wherein the female part of the optical coupler is configured to act as a hub to facilitate handling and torque steering of the guidewire.

7. The multisensor guidewire assembly of claim 1, wherein the coil of the guidewire has maximum outside diameter of ≤0.89 mm or ≤0.035 inch, and the male part of the optical coupler has an outside diameter no greater than the maximum outside diameter of the coil.

8. The multisensor guidewire assembly of claim 1, wherein at least the distal end portion of the guidewire assembly containing the sensor arrangement has a flexural modulus of 60GPa or more.

9. The multisensor guidewire assembly of claim 1, wherein at least the distal end portion of the guidewire containing the sensor arrangement provides the guidewire with predetermined stiffness characteristics wherein the guidewire stiffness is defined by a standard guidewire descriptor, said guidewire descriptor being one of stiff, extra-stiff, super-stiff and ultra-stiff, said descriptors being indicative of a flexural modulus in a range from about 17 GPa to 158 GPa.

10. The multisensor guidewire assembly of claim 1, wherein the flexible distal tip comprises an atraumatic preformed curved tip.

11. The multisensor guidewire assembly of claim 10 wherein the preformed curved tip has a three-dimensional curved structure.

12. The multisensor guidewire of claim 11, wherein the three-dimensional curved structure comprises a helix or a tapered helix shape.

13. The multisensor guidewire assembly of claim 1, wherein said at least two optical pressure sensors comprise Fabry-Pérot Micro-Opto-Mechanical-System (MOMS) pressure sensors and said sensor locations are spaced apart lengthwise along said length of the distal end portion to provide for one or more of:

a) placement of at least one pressure sensor in the aorta downstream of the aortic valve and placement of at least one pressure sensor in the left ventricle, upstream of the aortic valve for measurement of a transvalvular blood pressure gradient for the aortic valve;

b) placement of at least one pressure sensor in the left atrium upstream of the mitral valve and placement of at least one pressure sensor in the left ventricle, downstream of the mitral valve for measurement of a transvalvular blood pressure gradient for the mitral valve;

c) placement of at least one pressure sensor in the right atrium upstream of the tricuspid valve and placement of at least one pressure sensor in the right ventricle, downstream of the tricuspid valve, for measurement of a transvalvular blood pressure gradient for the triscuspid valve; and d) placement of at least one pressure sensor in the right ventricle upstream of the pulmonary valve and placement of at least one pressure sensor in the pulmonary artery, downstream of the pulmonary valve for measurement of a transvalvular blood pressure gradient for the pulmonary valve.

* * * * *